US009447440B2

(12) United States Patent
Fischer et al.

(10) Patent No.: US 9,447,440 B2
(45) Date of Patent: Sep. 20, 2016

(54) MICROORGANISMS FOR C4-DICARBOXYLIC ACID PRODUCTION

(71) Applicant: Novozymes, Inc., Davis, CA (US)

(72) Inventors: Amanda Fischer, Davis, CA (US);
Stephen Brown, Davis, CA (US);
Sheryl Luttringer, Loomis, CA (US)

(73) Assignee: Novozymes, Inc., Davis, CA (US)

( * ) Notice: Subject to any disclaimer, the term of this patent is extended or adjusted under 35 U.S.C. 154(b) by 112 days.

(21) Appl. No.: 14/159,786

(22) Filed: Jan. 21, 2014

(65) Prior Publication Data

US 2014/0134688 A1    May 15, 2014

Related U.S. Application Data

(62) Division of application No. 13/407,584, filed on Feb. 28, 2012, now Pat. No. 8,722,387.

(60) Provisional application No. 61/447,286, filed on Feb. 28, 2011.

(51) Int. Cl.
| C12N 1/00 | (2006.01) |
| C12P 7/46 | (2006.01) |
| C12N 15/00 | (2006.01) |
| C07H 21/04 | (2006.01) |
| C07K 14/38 | (2006.01) |
| C12N 1/14 | (2006.01) |

(52) U.S. Cl.
CPC .................. *C12P 7/46* (2013.01); *C07K 14/38* (2013.01); *C12N 1/14* (2013.01)

(58) Field of Classification Search
None
See application file for complete search history.

(56) References Cited

U.S. PATENT DOCUMENTS

| 3,063,910 A | 11/1962 | Abe et al. |
| 5,536,661 A | 7/1996 | Boel et al. |
| 7,504,490 B1 | 3/2009 | Weinstock et al. |
| 2011/0014654 A1 | 1/2011 | Tabuchi et al. |
| 2011/0053233 A1* | 3/2011 | Brown .................. C07K 14/38 435/145 |
| 2012/0135482 A1* | 5/2012 | Jansen ..................... C12N 1/18 435/142 |

FOREIGN PATENT DOCUMENTS

| EP | 2471943 A1 | 7/2010 |
| WO | 2007061590 A1 | 5/2007 |
| WO | 2008144626 A1 | 11/2008 |
| WO | 2009011974 A1 | 1/2009 |
| WO | 2009065778 A1 | 5/2009 |
| WO | WO 2009/134339 | * 11/2009 |
| WO | 2009155382 A1 | 12/2009 |
| WO | 2010003728 A1 | 1/2010 |
| WO | 2010111344 A2 | 9/2010 |
| WO | 2011024583 A1 | 3/2011 |
| WO | 2011028643 A1 | 3/2011 |
| WO | 2011066304 A2 | 6/2011 |

OTHER PUBLICATIONS

Fedorova et al, 2007, UniProt Access No. A1C406.
Battat 1991, Biotechnol Bioeng 37, 1108-1116.
Bauer 1999, FEMS Microbiol Lett 179, 107-113.
Bercovitz 1990, Appl Environ Microbiol 56, 1594-1597.
Camarasa 2001, Appl Environ Microbiol 67(9), 4144-4151.
Fedorova 2008, PLoS Genetics 4(4), 1-13.
Grobler 1995, Yeast 11, 1485-1491.
Nierman 2005, Nature 438 (22), 1151-1156.
Peleg 1988, Appl Microbiol Biotechnol 28, 69-75.
Pines 1997, Appl Microbiol Biotechnol 48, 248-255.
Sauer 2008, Trends Biotechnol 26, 100-108.
Zelle 2008, Appl Environ Microbiol 74, 2766-2777.
Machida et al 2006, UniProt Access No. Q2UGL1.
Machida et al 2006, UniProt Access No. Q2USG3.
Birren et al, 2008, UniProt Access No. B6JXU3.
Elleuche et al, 2009, Curr Genet 55, 211-222.
Goldberg et al, 2006, J Chem Technol Biotechnol 81(10), 1601-1611.
Nevoigt, 2008, Microbiol Mol Biol Revs 72(3), 379-412.
Nielsen et al, 2008, FEMS Yeast Res 8, 122-131.
Bush et al., 2010, GENESEQ, Access No. AWP70496.
Winkler er al., 2009, GENESEQ, Access No. ATT44026.
Nierman et al, 2005, UniProt Access No. Q4WCF3.
Ludwig et al, 1998, Plant Physiol 117 (3), 1071-1081.
WO 2011-024583—Eng Equiv—EP 2 471 943.
Zelle, Rintze Meindert. Metabolic engineering of *Saccharomyces cerevisiae* for C4-dicarboxylic acid production. PhD Thesis. Delft Univerisy of Technology, Delft, 2011.
Machida et al, 2006—Uniprot Acces No. Q2UKI1.
Machida et al, 2006—Uniprot Access No. Q2UC17.
Machida et al, 2005, Nature 438(7071), 1157-1161.
Lubertozzi et al, 2008, Biotechnol Advances 27, 53-75.
Whisstock et al 2003 Qtr Rev Biophys 36(3) 307-340.
Nierman et al, 2008—Genbank, Access No. XM_001276571.

* cited by examiner

*Primary Examiner* — Iqbal H Chowdhury
(74) *Attorney, Agent, or Firm* — Eric Fechter

(57) ABSTRACT

The present invention relates to isolated polypeptides having bicarbonate transporter activity and isolated polynucleotides encoding the polypeptides. The invention also relates to nucleic acid constructs, vectors, and host cells comprising the polynucleotides as well as methods of producing and using the polypeptides, and methods of producing C4-dicarboxylic acids, such as malic acid.

30 Claims, 15 Drawing Sheets

```
         M   E   S    S   A   V    Q   E   P    T   Q   Q   R    S   L   R   D    R   I   F
   1 ATGGAATCCA GCGCTGTACA GGAGCCGACT CAACAGCGCT CTTTGCGGGA TCGCATTTTT
         N   L   F    R   T   S    S   N   D    A   P   G    L   P   A   R    L   V   T
  61 AACCTCTTTC GTACCTCTTC CTCAAATGAT GCCCCGGGTC TTCCGGCAAG ACTCGTAACC
         A   E   S    A   A   Q    N   E   G   S    A   L   I    Y   P   P   R    E   P   D
 121 GCTGAGAGCG CAGCGCAAAA CGAAGGGTCG GCGTTAATCT ATCCGCCACG GGAGCCTGAT
         A   R   T    R   L   L    S   Y   D    R   G   E    R   G   L   R    N   S   G
 181 GCAAGGACTC GTCTTCTGA ATCGTACGAT CGCGGGGAAC GTGGTCTGAG GAACTCCGGC
         V   H   G    T   F   S   S    R   P   E    Q   E   E    I   Q   K   W    D   A   S
 241 GTTCATGGGA CTTTTTCTTC ACGACCTGAA CAGGAAGAAA TCCAAAAATG GGATGCAAGC
         S   L   Q    N   A   G   N    E   E   R    S   Q   S    P   G   G    D   G   H
 301 TCTTTGCAGA ATGCTGGTAA CGAAGAAAGA TCTCAGTCCC CAGGAGGAGC AGACGGCCAT
         I   G   S    P   G   D   V    S   G   Y    P   Q   G    P   E   N    I   P   S   L
 361 ATTGGGTCTC CCGGCGACGT CTCAGGATAC CCACAGGGAC CAGAGAATAT ACCATCGCTA
         D   S   S    F   T   A   L    H   M   K    N   H   K    S   L
 421 GACTCCTCTT TCACAGCATT GCACATGAAG AATCATAAAT CTCT*GTAGGT TTATAATCAC*
 481 *GTTCGCCCTG CTTTCTAACA CAATTGTTAT CTCCATCGTG GAGACAACTA ACGTTCATCA*
         Y   I   S   Y   Y   I    P   F   F    N   W   I    T   Q   Y   R    W   S   Y
 541 *A*GGTATATAT CTTACTACAT CCCATTTTTC AATTGGATTA CTCAATACCG GTGGTCGTAC
         I   R   G    D   L   V    A   A   T   T    I   A   S    I   Y   I   P    M   A   L
 601 ATTCGAGGTG ATTTGGTTGC TGCGACAACC ATTGCGTCCA TCTATATCCC TATGGCTTTG
         S   L   S    S   N   L    A   H   A   P    P   I   N    G   L   Y   S    F   V   I
 661 TCCTTATCCT CAAATCTCGC CCACGCACCT CCTATCAATG GCCTCTACTC TTTTGTGATC
         N   P   F    I   Y   A   I    F   G   S    S   P   L    L   I   V    P   E   A
 721 AACCCTTTCA TCTATGCGAT CTTCGGAGC AGCCCGCTGT TAATAGTGGG CCCAGAAGCA
         A   G   S    L   L   T   G    T   I   V    K   T   S    V   R   P    G   P   S   G
 781 GCAGGCTCCT TGCTTACTGG CACGATTGTC AAAACTAGTG TCAGACCAGG CCCATCTGGT
         E   D   D    E   V   A   N    A   I   V    G   I   A    T   A   M    A   G   A
 841 GAGGACGACG AAGTAGCGAA TGCCATCGTG GTCGGCATAG CCACTGCAAT GGCGGGCGCC
         M   I   L    I   A   G   L    T   R   L    G   F   L    D   N   V    L   S   R   P
 901 ATGATACTGA TCGCTGGGCT TACACGGCTG GGATTTCTGG ACAATGTGCT GAGCCGGCCC
         F   L   R    G   F   I   T    A   I   G    F   V   I    F   V   D   Q    L   I   P
 961 TTTCTTAGGG GTTTCATTAC AGCGATCGGT TTTGTGATTT TTGTGGATCA ACTCATCCCC
         E   V   G    L   T   E   L    A   K   E    A   G   V    T   H   G   T    T   V   D
1021 GAAGTCGGAT TGACCGAGCT AGCAAAGGAA GCTGGTGTTA CCCATGGGAC TACAGTTGAC
         K   L   M    F   L   I   R    N   I   G    C   H   A    L   T   T    A   V   A
1081 AAGCTCATGT TCCTTATAAG AAACATAGGA GGTTGCCATG CGCTTACAAC CGCGGTGGCT
         F   G   S    F   A   I   I    M   V   F    R
1141 TTTGGGAGCT TTGCTATTAT AATGGTATTT CG*GTTAGTGT TGGTGACTCG GAAGCCTGGT*
                                                                             T   L    K   K   M    L   Q   P   R    Y   P   Q
1201 *GCTTAGACTG ATTACCATTA CAG*GACTCTC AAGAAAATGC TCCAGCCGCG GTATCCTCAG
         V   I   Y    L   P   D   R    I   L   V    V   I   L    S   A   V   L    T   W   H
1261 GTGATTTATC TTCCGGACCG AATTCTCGTA GTTATTCTTT CAGCCGTCCT GACATGGCAT
         L   G   W    D   D   K   G    L   E   I    L   G   P    L   K   Q   N    A   N   G
1321 CTTGGTTGGG ATGACAAAGG GTTGGAGATT CTTGGGCCCT TGAAACAAAA TGCCAATGCC
         L   F   A    F   K   W   P    F   Q   F    S   Q   M    K   H   V   R    A   A   M
1381 CTTTTTGCGT TCAAATGGCC TTTCCAGTTT AGCCAGATGA AGCATGTACG CGCTGCAATG
         S   T   S    F   V   I   A    L   L   G    F   F   E    S   S   V    A   K   G
1441 AGTACTTCTT TCGTCATCGC GTTACTTGGC TTTTTCGAGT CTTCTGTTGC CGCCAAGGGA
         L   S   G    E   A   R   Q    E   G   V    Q   G   M    P   V   S    A   N   R   E
1501 CTTAGTGGCG AGGCCAGACA AGAAGGTGTC CAGGGAATGC CTGTCAGTGC TAACAGAGAG
         M   V   A    L   G   L    A   N   T   V    G   G   C    F   M   A   L    P   A   F
1561 ATGGTGGCGC TGGGTCTTGC TAATACTGTG GGGGCTGTT TCATGGCGCT TCCTGCGTTT
```

Fig. 3A

```
            G  G  Y     A  R  S  K     V  N  A     S  T  G     A  R  S  P     M  S  S
1621 GGTGGCTATG CAAGAAGCAA AGTCAACGCT TCAACTGGAG CTCGGTCTCC GATGAGCAGC
        I  F  L     S  I  I  T     F  V  C     I  M  V     L  L  P  Y     L  Y  Y
1681 ATTTTCCTGA GCATTATTAC CTTTGTTTGT ATCATGGTGC TTTTGCCGTA CTTATACTAT
     L  P
1741 CTTCCGGTGA GTCTCGACCC CAAATACTTC CGAGCGAAGG CTGAGAAAAT ATGTTGCAAT
                  K  A  V  L     S  S  M  I     S  V  V     A  F  S     L  I  E  E
1801 AATTCAGAAA GCCGTTCTTT CTTCTATGAT ATCTGTCGTC GCATTCAGTC TCATTGAAGA
        C  P  H     D  V  A     F  F  I  R     L  R  G     W  T  E     L  A  L  M
1861 ATGTCCTCAC GACGTGGCTT TCTTTATCCG ACTGCGCGGA TGGACGGAGC TAGCCCTAAT
        L  L  I     F  V  S     T  I  F  Y     S  L  E     L  G  I     A  L  G  I
1921 GCTTCTCATC TTTGTCTCGA CTATTTTCTA TTCTCTAGAG CTGGGAATTG CCCTTGGTAT
        G  L  S     I  L  I     L  I  R  H     S  T  Q     P  R  I     Q  I  L  G
1981 TGGCCTTTCT ATCTTGATCC TTATTCGCCA TTCTACGCAG CCTCGGATCC AAATTCTGGG
        K  I  A     G  T  T     D  R  F  D     N  A  E     L  H  P     E  S  V  E
2041 TAAGATAGCA GGCACTACCG ACCGTTTCGA TAACGCTGAA CTCCACCCCG AGAGCGTTGA
        L  I  E     G  A  L     I  V  K  I     P  E  P     L  T  F     A  N  T  G
2101 GTTAATCGAA GGCGCGCTTA TTGTTAAGAT CCCGGAACCG CTCACCTTTG CCAATACTGG
        E  L  K     N  R  L     R  R  L  E     L  Y  G     S  S  R     A  H  P  S
2161 TGAGCTCAAG AATCGTCTTC GGCGGTTGGA ATTATATGGC AGTAGCCGAG CGCACCCTTC
        L  P  P     T  R  T     P  E  H  N     K  N  I     I  F  D     V  H  G  V
2221 TCTTCCCCCC ACGCGCACCC CCGAACATAA CAAGAATATT ATATTTGATG TTCATGGTGT
        T  S  I     D  G  S     G  T  Q  V     L  Y  E     I  V  D     G  Y  A  D
2281 TACTAGCATC GATGGTTCCG GTACGCAAGT CTTATATGAG ATTGTGGACG GATATGCAGA
        Q  G  V     S  V  F     F  C  R  V     A  T  R     N  V  F     R  M  F  E
2341 CCAGGGGGTC AGCGTCTTCT TCTGCCGCGT CGCAACTCGC AATGTTTTCC GCATGTTTGA
        R  S  G     I  V  E     R  C  G  G     I  T  H     F  V  H     G  V  D  E
2401 ACGAAGTGGA ATTGTGGAAC GATGCGGTGG GATAACGCAC TTCGTTCATG GTGTCGACGA
        A  L  R     L  A  E     S  E  D  E     I  E  I     *
2461 AGCCCTCCGC CTTGCCGAAT CGGAAGACGA GATTGAAATC TGA
```

Fig. 3B

```
       M   P   G   D   L   K   T   K   I   G   H   G   A   A   K   A   L   G   I   K
   1 ATGCCGGGCG ATCTCAAAAC CAAAATTGGT CACGGCGCGG CCAAGGCCTT GGGGATCAAG
       I   P   Y   R   D   P   L   G   V   H   A   D   P   V   T   R   G   E   S   M
  61 ATCCCCTACC GTGATCCTCT CGGAGTTCAT GCTGACCCAG TCACACGAGG CGAGTCGATG
       F   S   V   G   T   I   D   T   Y   S   Y   L   E   P   E   P   T   P   A   E
 121 TTCTCCGTCG GAACGATCGA CACATACTCC TATCTCGAGC CCGAACCCAC TCCCGCTGAA
       W   L   K   E   V   C   P   S   W   H   Q   V   G   R   Y   F   Y   N   L   F
 181 TGGCTGAAGG AAGTCTGCCC TAGCTGGCAT CAGGTGGGCC GTTATTTTTA CAACCTTTTC
       P   F   L   S   W   I   T   R   Y   N   L   Q   W   L   L   G   D   M   I   A
 241 CCTTTCCTCT CGTGGATTAC GAGGTACAAC TTGCAATGGT TGCTGGGAGA TATGATTGCC

301 GGTAAGAGCC TTTCCACTGT GTTTGATTTG ATCGACAAGT AGACAACATA CTCATTGGAA
                       G   V   T   V   G   A   V   V   V   P   Q   G   M   A   Y   A   K   L   A
 361 TGCAGGCGTC ACGGTCGGTG CTGTGGTCGT TCCGCAGGGA ATGGCCTACG CTAAACTGGC
       N   L   P   V   E   Y   G   L   Y   S   F   M   G   V   L   I   Y   W   F
 421 AAACCTACCT GTAGAGTATG GTCTCTATTC CTCGTTCATG GGTGTTCTCA TTTATTGGTT
       F   A   T   S   K   D   I   T   I   G
 481 TTTTGCCACC TCAAAGGATA TCACCATTGG TGTAAGTCAT TCTGCACCCA TGTCAGCATG
                                                            P   V   A   V   M   S   T   L   T
 541 TATCTTGCTA ATATAGTATC TTCCCTGTTC AGCCGGTGGC TGTCATGTCT ACCCTTACAG
       G   K   I   V   A   E   A   Q   T   K   L   P   D   V   E   G   H   V   I   A
 601 GTAAGATAGT TGCCGAGGCG CAAACGAAGC TCCCAGATGT CGAAGGGCAT GTAATCGCCT
       S   C   L   A   I   I   C   G   A   V   C   A   M   G   L   L   R   L   G
 661 CCTGTTTGGC TATCATTTGT GGAGCCGTGG TTTGCGCTAT GGGCCTGCTT CGGCTGGGAT
       F   I   V   D   F   I   P   L   P   A   I   S   A   F   M   T   G   S   A   I
 721 TTATCGTGGA TTTCATTCCT CTGCCGGCAA TTTCAGCTTT CATGACGGGT TCCGCCATCA
       N   I   C   S   G   Q   V   K   D   M   L   G   E   T   A   D   F   S   T   K
 781 ATATCTGCTC CGGACAGGTC AAAGACATGC TGGGAGAGAC GGCCGACTTC TCGACGAAAG
       D   S   T   Y   L   V   I   I   N   T   L   K   H   L   P   S   A   K   I   D
 841 ATTCTACCTA TCTGGTTATC ATCAACACCC TCAAGCATCT TCCCTCCGCA AAAATCGATG
       A   A   M   G   V   S   A   L   A   M   L   Y   I   I   R   S   G   C   N   Y
 901 CCGCCATGGG TGTCAGTGCT TTAGCTATGC TGTACATTAT CCGTTCGGGT TGCAATTATG
       G   A   K   K   F   P   R   H   A   K   V   W   F   F   V   S   T   L   R   T
 961 GCGCGAAGAA GTTCCCCCGT CATGCCAAGG TTTGGTTCTT CGTTTCGACT TTGCGCACAG
       V   F   V   I   L   F   Y   T   M   I   S   A   A   V   N   L   H   R   R   S
1021 TGTTCGTGAT CTTGTTCTAT ACGATGATCA GTGCCGCTGT GAACTTGCAC CGGCGGTCTA
       N   P   R   F   K   L   L   G   K   V   P   R   G   F   Q   H   A   A   V   P
1081 ACCCGCGGTT CAAGCTCCTG GGTAAAGTTC CTCGTGGTTT CCAACATGCG GCTGTCCCTC
       Q   V   N   S   R   I   I   S   A   F   A   S   E   L   P   A   S   I   I   V
1141 AGGTAAATTC GAGGATCATC AGCGCATTTG CTAGCGAACT TCCTGCTTCG ATTATTGTCC
       L   L   I   E   H   I   A   I   S   K   S   F   G   R   V   N   N   Y   T   I
1201 TGCTTATCGA ACACATCGCT ATCTCGAAAT CCTTTGGCCG TGTCAACAAC TACACAATTG
       D   P   S   Q   E   L   V   A   I   G   V   S   N   L   G   P   F   L   G
1261 ATCCCTCTCA GGAGCTGGTT GCTATTGGTG TGTCGAACTT GCTTGGACCG TTCCTTGGTG
       G   Y   P   A   T   G   S   F   S   R   T   A   I   K   S   A   G   V   R
1321 GTTACCCAGC GACTGGATCG TTCTCCCGAA CTGCAATCAA ATCGAAAGCG GGTGTCCGCA
       T   P   L   A   G   V   I   T   A   V   V   L   L   A   I   Y   A   L   P
1381 CCCCACTTGC CGGTGTTATT ACTGCGGTTG TTGTCCTCCT CGCCATTTAC GCTCTGCCCG
       A   V   F   F   Y   I   P   K   A   S   L   A   G   V   I   I   H   A   V   G
1441 CTGTCTTCTT TTACATCCCG AAAGCTTCCC TTGCTGGTGT CATCATTCAT GCAGTCGGTG
       D   L   I   T   P   P   N   T   V   Y   Q   F   W   R   V   S   P   L   D   A
1501 ACCTCATTAC CCCACCAAAC ACCGTTTACC AGTTCTGGCG CGTGTCCCCT CTGGATGCGA
       I   I   F   F   I   G   V   I   V   T   V   F   T   T   I   E   I   G   I   Y
1561 TCATTTTCTT TATCGGTGTT ATCGTGACTG TCTTCACCAC GATTGAGATC GGCATTTACT
       C   T   V   C   V   S   V   A   I   L   L   F   R   V   A   K   A   R   G   Q
1621 GTACCGTTTG TGTGTCTGTT GCCATTCTGC TGTTCCGCGT CGCCAAGGCC CGCGGTCAAT
```

Fig. 4A

```
         F  L  G  R     V  T  I     H  S  V     I  G  D  H     L  V  Q     D  D  G
1741 TCTTAGGAAG AGTCACTATC CACTCGGTGA TCGGTGACCA TCTGGTACAG GATGATGGGA
         K  Y  G  S     A  N  S     P  N  A     A  S  D  D     K  D  E     L  S  R
1801 AATATGGGTC TGCCAACTCC CCTAATGCTG CCAGCGATGA CAAAGATGAA TTGAGCCGGT
         S  I  F  L     P  I  N     H  T  D     G  S  N     D  V  E     V  Q  Q
1861 CTATCTTCTT GCCTATCAAC CACACGGACG GATCGAATCC CGATGTCGAG GTGCAGCAAC
         P  Y  P  G     I  F  I     Y  R  F     S  E  G  F     N  Y  P     N  A  N
1921 CTTATCCTGG TATCTTCATC TACCGATTCT CGGAAGGATT CAACTACCCC AATGCCAATC
         H  Y  T  D     Y  L  V     Q  T  I     F  K  H     T  R  R  T     N  P  F
1981 ACTACACCGA TTATTTGGTC CAGACTATCT TCAAGCATAC ACGTCGCACA AATCCGTTCT
         S  Y  G  K     P  G  D     R  P  W     N  N  P  G     P  R  R     G  K  S
2041 CCTACGGTAA ACCGGGTGAT CGGCCATGGA ATAATCCTGG CCCTCGCAGG GGCAAGTCTG
         E  D  D  E     S  H  L     P  L  L     Q  A  V  I     L  D  F     S  S  V
2101 AAGATGACGA GTCGCATTTG CCCTTACTGC AGGCTGTCAT TCTTGACTTC TCATCCGTCA
         N  N  V  D     V  T  S     V  Q  N     L  I  D  V     R  N  Q     L  D  L
2161 ACAATGTTGA TGTGACCTCG GTCCAGAACC TCATCGATGT CCGCAATCAA CTCGACCTCT
         Y  A  S  P     K  T  V     Q  W  H     F  A  H  I     N  N  R     W  T  K
2221 ACGCTTCGCC TAAGACTGTG CAGTGGCACT TTGCTCATAT TAACAACCGC TGGACGAAAC
         R  A  L  A     A  G     F  G  F     P  S  P  D     S  D  E     G  F  Q
2281 GAGCCCTTGC AGCAGCAGGT TTCGGCTTCC CATCTCCGGA CTCGGATGAA GGATTCCAGA
         R  W  K  P     I  F  S     V  A  E     I  E  G  S     A  S  A     A  H
2341 GATGGAAGCC AATTTTCAGC GTGGCTGAGA TCGAAGGCAG TGCCTCTGCC GCAGCTCATG
         A  E  M  V     N  N  R     H  T  Q     H  N  I  K     S  E  D     L  E  H
2401 CAGAGATGGT GAACAACAGA CACACCCAGC ATAACATCAA GAGCGAAGAC CTCGAGCATG
         G  L  K  H     D  S  E     T  T  E     R  E  T  H     G  I  E     E  S  S
2461 GCCTCAAGCA CGATTCAGAG ACCACCGAGC GTGAGACACA CGGCATCGAA GAATCCTCCG
         D  A  S  S     T  R  E     D  K  L     Q  R  D  L     K  D  S     K  A  Y
2521 ATGCCAGCAG CACCCGGGAG GACAAGTTGC AACGGGACCT GAAGGATAGC AAGGCTTACC
         R  S  R  R     R  V  A     M  V  Q     G  L  N  R     P  F  F     H  I  D
2581 GCAGTCGCCG AAGGGTCGCT ATGGTGCAGG GCCTCAACCG GCCATTCTTC CACATCGACC
         L  T  S  A     L  Q  S     A  L  A     N  A  G  E     Q  P  D     P  K  M
2641 TGACTAGTGC ACTGCAGAGT GCCTTGGCCA ACGCGGGCGA GCAGCCGGAC CCTAAAATGA
         N  V  L  D     A  *
2701 ATGTCCTTGA TGCATAG
```

Fig. 4B

```
      M   H   D   H   S   T   G   S   S   P   Y   I   S   D   V   E   T   L   N   H
   1 ATGCACGACC ACAGCACTGG ATCTAGTCCA TACATCTCGG ACGTGGAAAC CTTGAACCAC
      A   C   E   K   S   V   N   P   E   T   K   V   S   Q   P   Q   E   S   P   I
  61 GCCTGCGAGA AGTCCGTCAA CCCCGAGACC AAAGTCTCCC AGCCTCAGGA ATCTCCCATT
      I   S   N   N   E   H   Q   E   F   V   K   L   G   I   R   Q   R   L   R   H
 121 ATCAGCAATA ATGAACATCA GGAGTTTGTT AAGCTGGGCA TCCGCCAACG GCTGCGTCAT
      F   T   W   A   W   Y   T   L   T   M   S   A   G   G   L   A   L   L   R
 181 TTCACCTGGG CCTGGTATAC CCTAACCATG AGCGCAGGTG GACTGGCCCT TCTTCTCCGC
      N   Q   P   Y   Q   F   K   G   L   K   E   I   G   L   V   V   Y   I   A   N
 241 AACCAGCCGT ATCAATTCAA GGGGTTGAAG GAGATAGGCC TGGTGGTATA CATAGCCAAT
      L   V   F   F   T   I   I   G   S   L   M   I   T   R   F   V   L   Y   N   N
 301 CTCGTCTTCT TTACTATCAT CGGCTCTCTT ATGATCACCA GGTTTGTTCT TTACAACAAC
      L   M   D   S   L   R   H   D   R   E   G   F   F   F   P   T   F   W   L   S
 361 CTGATGGACT CTCTCCGCCA CGACCGAGAA GGTTTCTTCT TTCCAACCTT CTGGCTCTCC
      I   A   T   M   I   S   G   L   S   A   Y   F   S   T   E   D   T   H   R   L
 421 ATCGCCACCA TGATTAGTGG TCTATCTGCC TACTTCTCTA CTGAAGACAC GCACCGCCTC
      N   Y   A   L   E   G   L   F   W   A   Y   C   I   F   T   F   A   S   A   V
 481 AATTATGCTC TCGAGGGTCT CTTCTGGGCG TACTGTATCT TCACGTTTGC CTCAGCAGTG
      I   Q   Y   S   F   V   F   S   Y   H   F   P   L   Q   T   M   M   P   S
 541 ATCCAGTACT CCTTTGTCTT CTCCTATCAC TTCCCTC TGCAAACTAT GATGCCATCA
      W   I   L   P   A   F   P   I   M   L   S   G   T   I   A   S   A   A   S   S
 601 TGGATCTTAC CGGCATTCCC TATCATGCTG AGCGGAACCA TTGCCTCTGC CGCTTCCAGC
      Y   Q   P   A   V   S   A   T   P   M   I   V   A   G   I   T   F   Q   G   L
 661 TACCAGCCTG CGGTGTCTGC CACGCCTATG ATTGTTGCCG GCATCACGTT CCAGGGACTC
      G   F   C   I   S   F   M   M   Y   A   H   Y   I   G   R   L   M   E   T   G
 721 GGATTCTGCA TCAGCTTCAT GATGTACGCC CACTACATCG GCCGTCTGAT GGAGACGGGC
      I   P   S   S   E   H   R   P   G   M   F   I   C   V   G   P   P   A   F   T
 781 ATCCCTTCGA GCGAGCACCG TCCTGGTATG TTCATCTGTG TCGGCCCCCC TGCCTTCACG
      L   L   A   I   I   G   M   A   N   G   L   P   E   G   F   S   I   L   G   D
 841 CTGCTGGCTA TCATCGGCAT GGCCAACGGC CTTCCCGAGG GCTTCAGTAT CCTGGGCGAT
      G   G   M   D   D   R   H   I   M   R   V   L   A   V   C   A   G   M   F   L
 901 GGTGGCATGG ACGACCGTCA CATCATGCGA GTACTGGCCG TCTGCGCGGG CATGTTCCTC
      W   A   L   S   I   W   F   C   V   A   L   G   S   V   V   R   A   P   P
 961 TGGGCTCTGA GCATTTGGTT CTTCTGTGTC GCTCTGGGCT CAGTTGTGCG GGCGCCTCCC
      H   D   F   H   L   N   W   A   M   V   F   P   N   T   G   L   T   L   A
1021 CATGATTTCC ACCTCAACTG GGCGGCTATG GTCTTCCCTA ACACCGGACT CACTCTCGCC
      T   I   T   L   A   K   S   L   D   S   A   A   L   K   W   V   G   V   G   M
1081 ACCATCACCC TGGCCAAGTC ACTGGACAGT GCCGCGTTGA AATGGGTGGG CGTGGGCATG
      S   L   C   V   I   C   M   F   I   F   V   F   V   S   T   I   R   A   V   L
1141 TCCCTCTGCG TGATCTGCAT GTTCATCTTC GTCTTCGTGA GCACCATTAG GGCTGTTCTC
      L   K   R   I   M   W   P   G   R   D   E   D   V   S   E   L   F   E   *
1201 TTGAAGAGGA TCATGTGGCC AGGTCGGGAT GAGGATGTGT CCGAGTTGTT CGAATGA
```

Fig. 6

```
             M   V   K   A
   1   ATGGTCAAAG CTGGTGAGTT AGCAATCCTT AACAGATGAC ACTCTCATAG GTACTAACTC
                     A   V   L   G   A   S   G   G   I   G   Q
  61   GAAACGTTAG CGGTACTTGG AGCTTCTGGT GGCATTGGCC AGGTATGGAT ATCCCCACGC
                                                                 P   L   S
 121   CTTACAACCC TGGTCACAAT ATGACCTTGT TCGATACTGA CTATCTCCCA AGCCACTGTC
             L   L   L   K   T   C   P   L   V   E   E   L   A   L   Y   D   V   V   N   T
 181   TCTCCTGTTG AAGACCTGTC CCTTAGTTGA AGAGCTTGCT CTCTACGATG TTGTGAACAC
             P   G   V   A   A   D   L   S   H   I   S   S   I   A
 241   CCCTGGTGTT GCTGCTGATC TATCCCACAT CTCGTCTATC GCTGTACGTT ACTGCCACAA
                                                                         K
 301   TGCGAATTGC CCGATGGAAG AGGCGAAAAA TGGTATCTTG CTTACCTGGG CGATTAGAAA
             I   S   G   F   L   P   K   D   D   G   L   K   Q   A   L   T   G   A   N   I
 361   ATCTCTGGTT TTCTGCCCAA AGATGATGGG CTGAAGCAGG CCCTTACTGG TGCTAATATT
             V   V   I   P   A   G   I   P
 421   GTTGTCATCC CGGCTGGTAT TCCCCGTAAG TCCCTACCCT TTCGCATTGC TCCTCGTATG
                                                 R   K   P   G   M   T   R   D   D
 481   TTCGCTGGTG GCCAGTTTTC TGATAGTTGA TAGGCAAGCC TGGTATGACC CGTGACGACC
             L   F   K   I   N   A   G   I   V   R   D   L   V   K   G   I   A   E   F   C
 541   TCTTCAAGAT CAACGCCGGC ATAGTGCGAG ACTTGGTCAA GGGTATCGCC GAGTTCTGCC
             P   K   A   F   V   L   V   I   S   N   P   V   N   S   T   V   P   I   A   A
 601   CCAAGGCCTT TGTTCTGGTT ATCTCAAACC CCGTTAATTC TACTGTTCCT ATTGCTGCAG
             E   V   L   K   A   A   G   V   F   D   P   K   R   L   F   G   V   T   T   L
 661   AGGTGCTCAA AGCCGCTGGC GTCTTTGACC CGAAGCGCCT CTTTGGTGTC ACCACACTGG
             D   V   V   R   A   E   T   F   T   Q   E   F   S   G   Q   K   D   P   S   A
 721   ACGTCGTTCG TGCAGAGACT TTCACCCAAG AGTTCTCGGG CCAGAAGGAT CCTTCTGCTG
             V   Q   I   P   V   V   G   H   S   G   E   T   I   V   P   L   F   S   K
 781   TTCAAATCCC AGTTGTTGGT GGCCACTCTG GAGAGACCAT TGTCCCCCTC TTCAGCAAGA
             T   T   P   A   I   Q   I   P   E   E   K   Y   D   A   L   I   H
 841   CTACCCCCGC AATTCAGATA CCCGAGGAGA AGTATGACGC ACTGATCCAC CGTAGGTTGT
                                                                         R   V   Q   F
 901   CCCAAAGAAT CTCATGAATA TCTTGCTGTA AGCACTAACT ATGCTTCAGG CGTCCAATTT
             G   G   D   E   V   V   Q   A   K   D   G   A   G   S   A   T   L   S   M   A
 961   GGTGGAGATG AGGTGGTCCA AGCTAAGGAC GGTGCTGGTT CCGCCACCTT GTCTATGGCC
             Y   A   G   Y   R
1021   TATGCCGGTT ACAGGTAGGG ATGCTGCGTA CCGTGAGAGC ACTCGCGGCT AACATGCCAT
             F   A   E   S   V   I   K   A   S   K   G   Q   T   G   I   V   E   P   T
1081   AGGTTCGCTG AGAGTGTAAT CAAAGCTTCA AAGGGTCAAA CGGGTATTGT CGAGCCTACC
             F   V   Y   L   P   G   I   P   G   D   E   I   V   K   A   T   G   V   E
1141   TTCGTCTACC TGCCTGGAAT TCCCGGCGGT GATGAGATCG TTAAGGCAAC TGGCGTGGAA
             F   F   S   T   L   V   T   L   G
1201   TTCTTCTCTA CTCTTGTAAC CTTAGGAGTA AGATTCATCT CCTCACAGAA TCTTCGTTCA
                                                 T   N   G   A   E   K   A   S   N   V
1261   TATCACGCCA GGCTAACGCT ATTAAACAGA CTAATGGCGC AGAGAAGGCT AGCAACGTTC
             L   E   G   V   T   E   K   E   K   K   L   E   A   C   T   K   G   L   K
1321   TTGAGGGCGT GACCGAGAAG GAAAAGAAGC TTCTCGAGGC TTGCACGAAA GGCCTTAAGG
             G   N   I   E   K   G   I   D   F   V   K   N   P   P   P   K   *
1381   GTAATATCGA GAAAGGCATC GACTTCGTTA AGAACCCACC ACCAAAGTAA
```

Fig. 7

```
          M   A   A       P   F   R   Q       P   E   E       A   V   D       D   T   E   F       I   D   D
   1   ATGGCGGCTC CGTTTCGTCA GCCTGAGGAG GCGGTCGATG ACACCGAGTT CATCGATGAC
          H   H   E       H   L   R   D       T   V   H       H   R   L       R   A   N   S       S   I   M
  61   CACCATGAAC ACCTCCGTGA TACCGTGCAC CATCGGTTGC GCGCCAATTC CTCCATTATG
          H   F   Q       K   I   L   V       A   N   R       G   E   I       P   I   R   I       F   R   T
 121   CACTTCCAGA AGATCCTCGT CGCCAACCGT GGTGAGATCC CCATTCGTAT CTTCAGAACG
          A   H   E       L   S   L   Q       T   V   A       I   Y   S       H   E   D   R       L   S   M
 181   GCCCACGAGC TGTCCTTGCA GACGGTTGCT ATCTACTCTC ATGAGGATCG ACTGTCAATG
          H   R   Q       K   A   D   E       A   Y   M       I   G   H       R   G   Q   Y       T   P   V
 241   CACCGTCAAA AGGCCGATGA GGCCTACATG ATTGGCCACC GCGGTCAGTA CACCCCTGTC
          G   A   Y       L   A   G   D       E   I   I       K   I   A       L   E   H   G       V   Q   L
 301   GGTGCGTACC TGGCGGGCGA TGAGATCATC AAGATCGCCC TGGAGCACGG TGTCCAGCTG
          I   H   P       G   Y   G   F       L   S   E       N   A   D       F   A   R   K       V   E   N
 361   ATCCACCCGG GCTACGGTTT CTTGTCCGAG AACGCCGACT TCGCCCGCAA GGTTGAGAAC
          A   G   I       V   F   V   G       P   T   P       D   T   I       D   S   L   G       D   K   V
 421   GCCGGCATTG TCTTTGTGGG ACCCACTCCC GATACCATTG ACAGCTTGGG TGACAAGGTG
          S   A   R       R   L   A   I       K   C   E       V   P   V       V   P   G   T       E   G   P
 481   TCGGCCCGTC GGCTGGCCAT TAAGTGCGAG GTCCCTGTCG TTCCGGGTAC GGAGGGCCCC
          V   E   R       Y   E   E   V       K   A   F       T   D   T       Y   G   F   P       I   I   I
 541   GTCGAGCGCT ATGAGGAGGT CAAGGCGTTC ACAGACACCT ATGGCTTCCC CATCATCATC
          K   A   A       F   G   G   G       R   G   M       R   V   V       R   D   Q   A       E   L
 601   AAGGCTGCCT TTGGCGGTGG TGGCCGTGGT ATGCGTGTGG TCCGTGACCA GGCCGAGCTG
          R   D   S       F   E   R   A       T   S   E       A   R   S       A   F   G   N       G   T   V
 661   CGTGACTCGT TCGAGCGAGC CACCTCTGAG GCCCGCTCCG CCTTCGGCAA TGGTACCGTC
          F   V   E       R   F   L   D       K   P   K       H   I   E       V   Q   L   L       G   D   S
 721   TTCGTCGAGC GCTTCCTCGA CAAACCCAAG CACATTGAAG TCCAGCTTCT GGGTGACAGC
          H   G   N       V   V   H   L       F   E   R       D   C   S       V   Q   R   R       H   Q   K
 781   CACGGCAACG TTGTCCATCT GTTTGAGCGT GACTGCTCCG TGCAGCGTCG TCACCAGAAG
          V   V   E       A   P   A   K       D   L       P   A   D       V   R   D   R       I   L   A
 841   GTCGTTGAGG TTGCTCCGGC TAAGGACCTG CCAGCCGATG TCCGGGACCG CATCCTGGCC
          D   A   V       K   L   A   K       S   V   N       Y   R   N       A   G   T   A       E   F   L
 901   GATGCTGTGA AGCTGGCCAA GTCCGTCAAC TACCGTAACG CCGGTACAGC TGAGTTCCTG
          V   D   Q       Q   N   R   H       Y   F   I       E   I   N       P   R   I   Q       V   E   H
 961   GTGGACCAGC AGAACCGCCA CTACTTCATT GAAATCAATC CTCGTATCCA AGTCGAGCAC
          T   I   T       E   E   I   T       G   I   D       I   V   A       A   Q   I   Q       I   A   A
1021   ACCATCACCG AAGAGATTAC TGGTATCGAT ATCGTGGCTG CACAGATCCA GATTGCTGCT
          G   A   S       L   E   Q   L       G   L   T       Q   D   R       I   S   A   R       G   F   A
1081   GGTGCAAGCC TCGAGCAACT GGGCCTGACT CAGGACCGCA TCTCCGCCCG CGGATTTGCC
          I   Q   C       R   I   T   T       E   D   P       A   K   G       F   S   P   D       T   G   K
1141   ATTCAATGTC GTATCACCAC GGAAGATCCC GCCAAGGGGT TCTCTCCGGA TACTGGTAAG
          I   E   V       Y   R   S   A       G   G   N       G   V   R       L   D   G   G       N   G   F
1201   ATTGAGGTTT ATCGTTCCGC TGGTGGTAAC GGTGTCCGTC TGGATGGTGG TAACGGTTTC
          A   G   A       I   I   T   P       H   Y   D       S   M   L       V   K   C   T       C   R   G
1261   GCTGGTGCTA TCATCACCCC TCACTACGAC TCCATGCTGG TCAAGTGCAC CTGCCGTGGT
          S   T   Y       E   I   A   R       R   K   V       V   R   A       L   V   E   F       R   I   R
1321   TCGACCTATG AAATCGCTCG TCGCAAGGTT GTGCGTGCCT TGGTCGAGTT CCGTATTCGT
          G   V   K       T   N   I   P       F   L   T       S   L   L       S   H   P   T       F   V   D
1381   GGTGTGAAGA CCAACATTCC CTTCCTGACT TCGCTTCTGA GCCACCCGAC CTTCGTCGAT
          G   N   C       W   T   T   F       I   D   D       T   P   E       L   F   S   L       V   G   S
1441   GGAAACTGCT GGACCACTTT CATCGACGAC ACCCCTGAAT TGTTCTCTCT TGTCGGCAGT
          Q   N   R       A   Q   K   L       L   A   Y       L   G   D       V   A   V   N       G   S   S
1501   CAGAACCGTG CCCAGAAGCT GCTCGCATAC CTCGGCGATG TAGCTGTCAA CGGTAGTAGC
          I   K   G       Q   I   G   E       P   K   L       K   G   D       V   I   K   P       K   L   F
1561   ATCAAGGGCC AAATTGGCGA GCCCAAGCTC AAGGGTGATG TCATCAAGCC GAAGCTTTTC
          D   A   E       G   K   P   L       D   V   S       A   P   C       T   K   G   W       K   Q   I
1621   GATGCCGAGG GCAAGCCGCT TGACGTTTCC GCCCCCTGCA CCAAGGGTTG GAAGCAGATT
          L   D   R       E   G   P   A       A   F   A       K   A   V       R   A   N   K       G   C   L
1681   CTGGACCGGG AGGGTCCGGC TGCCTTTGCG AAGGCCGTGC GTGCCAACAA GGGTTGCTTG
          I   M   D       T   T   W   R       D   A   H       Q   S   L       L   A   T   R       V   R   T
1741   ATCATGGATA CTACCTGGCG TGACGCCCAC CAGTCTTTGC TGGCCACCCG TGTGCGTACC
          I   D   L       L   N   I   A       H   E   T       S   Y   A       Y   S   N   A       Y   S   L
1801   ATCGACTTGT TGAACATCGC CCATGAGACC AGCTACGCCT ACTCCAATGC GTACAGTTTG
```

Fig. 9A

```
            E   C   W       G   G   A   T       F   D   V       A   M   R       F   L   Y   E       D   P   W
     1861 GAATGCTGGG GTGGTGCTAC CTTCGATGTG GCCATGCGTT TCCTCTATGA GGACCCCTGG
            D   R   L       R   K   M   R       K   A   V       P   N   I       P   F   Q   M       L   L   R
     1921 GACCGCCTGC GCAAGATGCG TAAGGCTGTT CCTAACATCC CATTCCAGAT GTTGCTCCGT
            G   A   N       G   V   A   Y       S   S   L       P   D   N       A   I   Y   H       F   C   K
     1981 GGTGCCAACG GTGTCGCCTA CTCTTCCCTC CCAGACAACG CCATCTACCA CTTCTGTAAG
            Q   A   K       K   C   G       D   I   F       R   V   F       D   A   L   N       D   V   D
     2041 CAGGCTAAGA AGTGCGGTGT CGACATTTTC CGTGTTTTCG ACGCCCTCAA CGATGTCGAT
            Q   L   E       V   G   I   K       A   V   H       A   A   E       G   V   V   E       A   T   M
     2101 CAGCTCGAGG TCGGTATCAA GGCTGTTCAT GCTGCCGAGG GTGTTGTCGA GGCCACCATG
            C   Y   S       G   D   M   L       N   P   H       K   K   Y       N   L   E   Y       Y   M   A
     2161 TGCTACAGCG GTGACATGCT GAACCCCCAC AAGAAGTACA ACCTGGAGTA CTACATGGCC
            L   V   D       K   I   V   A       M   K   P       H   I   L       G   I   K   D       M   A   G
     2221 TTGGTGGATA AGATTGTAGC CATGAAGCCT CACATCCTTG GTATCAAGGA TATGGCCGGT
            V   L   K       P   Q   A   A       R   L   L       V   G   S       I   R   Q   R       Y   P   D
     2281 GTGCTGAAGC CCCAGGCCGC TCGCCTGTTG GTGGGCTCCA TCCGTCAGCG CTACCCTGAC
            L   P   I       H   V   H   T       H   D   S       A   G   T       G   V   A   S       M   I   A
     2341 CTTCCCATCC ACGTCCACAC CCACGACTCC GCTGGTACTG GTGTAGCTTC CATGATTGCC
            C   A   Q       A   G   A   D       A   V   D       A   A   T       D   S   M   S       G   M   T
     2401 TGTGCCCAGG CGGGTGCCGA CGCCGTGGAC GCCGCGACCG ACAGCATGTC CGGTATGACC
            S   Q   P       S   I   G   A       I   L   A       S   L   E       G   T   E   Q       D   P   G
     2461 TCCCAGCCTA GCATTGGTGC CATTCTGGCC TCTCTTGAGG GCACTGAGCA AGACCCCGGT
            L   N   L       A   H   V   R       A   I   D       S   Y   W       A   Q   L   R       L   L   Y
     2521 CTCAACCTCG CCCACGTGCG CGCTATTGAT AGCTACTGGG CACAGCTGCG CTTGCTCTAC
            S   P   F       E   A   G   L       T   G   P       D   P   E       V   Y   E   H       E   I   P
     2581 TCTCCTTTCG AGGCGGGTCT CACTGGCCCC GACCCTGAGG TCTACGAGCA CGAGATCCCT
            G   G   Q       L   T   N   L       I   F   Q       A   S   Q       L   G   L   G       Q   Q   W
     2641 GGTGGTCAGT TGACCAACCT TATCTTCCAG GCCAGTCAGC TCGGCTTGGG CCAGCAGTGG
            A   E   T       K   K   A   Y       E   A   A       N   D   L       L   G   D   I       V   K   V
     2701 GCCGAAACCA AGAAGGCCTA TGAGGCGGCT AATGATTTAC TCGGCGACAT TGTAAAGGTC
            T   P   T       S   K   V   V       G   D   L       A   Q   F       M   V   S   N       K   L   T
     2761 ACTCCCACCT CCAAGGTGGT CGGTGACTTG GCTCAGTTCA TGGTCTCGAA CAAACTGACT
            P   E   D       V   V   E   R       A   G   E       L   D   F       P   G   S   V       L   E   F
     2821 CCAGAGGATG TTGTTGAGCG TGCTGGTGAG CTGGACTTCC CTGGTTCTGT GCTCGAATTC
            L   E   G       L   M   G   Q       P   F   G       G   F   P       E   P   L   R       S   R   A
     2881 CTCGAAGGTC TCATGGGACA GCCCTTCGGT GGATTCCCCG AGCCATTGCG CTCCCGCGCC
            L   R   D       R   R   K   L       E   K   R       P   G   L       Y   L   E   P       L   D   L
     2941 CTGCGCGATC GCCGCAAGCT CGAGAAGCGT CCAGGTCTCT ACCTCGAGCC TTTGGATTTG
            A   K   I       K   S   Q   I       R   E   K       F   G   A       A   T   E   Y       D   V   A
     3001 GCTAAGATCA AGAGCCAGAT CCGTGAGAAG TTCGGTGCTG CTACTGAGTA TGACGTGGCC
            S   Y   A       M   Y   P   K       V   F   E       D   Y   K       F   V   Q   K       F   G
     3061 AGCTATGCCA TGTATCCCAA GGTCTTCGAG GACTACAAGA AGTTCGTCCA GAAGTTCGGT
            D   L   S       V   L   P   T       R   Y   F       L   A   K       P   E   I   G       E   E   F
     3121 GATCTCTCCG TCTTGCCCAC ACGGTACTTC TTGGCCAAGC CTGAGATTGG CGAGGAGTTC
            H   V   E       L   E   K   G       K   V   L       I   L   K       L   L   A   I       G   P   L
     3181 CACGTTGAGC TGGAGAAGGG TAAGGTGCTC ATCCTGAAGT TGTTGGCCAT CGGCCCTCTT
            S   E   Q       T   G   Q   R       E   V   F       Y   E   V       N   G   E   V       R   Q   V
     3241 TCAGAGCAGA CTGGTCAGCG TGAGGTCTTC TACGAAGTCA ACGGTGAGGT GCGCCAGGTC
            A   V   D       D   N   K   A       S   V   D       N   T   S       R   P   K   A       D   V   G
     3301 GCTGTTGATG ACAACAAGGC TTCCGTGGAC AACACTTCAC GCCCTAAGGC CGATGTGGGT
            D   S   S       Q   V   G   A       P   M   S       G   V   V       E   I   R       V   H   D
     3361 GACAGCAGCC AGGTCGGTGC TCCTATGAGC GGTGTGGTTG TTGAAATCCG TGTCCACGAT
            G   L   E       V   K   K   G       D   P   L       A   V   L       S   A   M   K       M
     3421 GGTCTGGAGG TTAAGAAGGG TGACCCACTT GCCGTCCTGA GTGCCATGAA GATG GTAAGT
                                                                                        E   M
     3481 TCATTCCGAA TCATTTTTCT CACTGGTCAA CTACAGATGC TAACAGCTTA TCCAG GAAAT
            V   I   S       A   P   H       S   G   K   V       S   S   L       L   V   K       E   G   D   S
     3541 GGTTATCTCT GCTCCTCACA GTGGAAAGGT CTCCAGCTTG CTGGTCAAGG AGGGCGATTC
            V   D   G       Q   D   L       V   C   K   I       V   K   A       *
     3601 TGTGGATGGC CAGGATCTCG TCTGCAAGAT CGTCAAAGCG TAA
```

Fig. 9B

SEQUENCE LISTING

<160> NUMBER OF SEQ ID NOS: 57

<210> SEQ ID NO 1
<211> LENGTH: 2503
<212> TYPE: DNA
<213> ORGANISM: Aspergillus oryzae

<400> SEQUENCE: 1

```
atggaatcca gcgctgtaca ggagccgact caacagcgct ctttgcggga tcgcattttt      60
aacctctttc gtacctcttc ctcaaatgat gccccgggtc ttccggcaag actcgtaacc     120
gctgagagcg cagcgcaaaa cgaagggtcg gcgttaatct atccgccacg ggagcctgat     180
gcaaggactc gtcttctcga atcgtacgat cgcggggaac gtggtctgag gaactccggc     240
gttcatggga cttttctc acgacctgaa caggaagaaa tccaaaaatg ggatgcaagc       300
tctttgcaga atgctggtaa cgaagaaaga tctcagtccc caggaggagc agacggccat     360
attgggtctc ccggcgacgt ctcaggatac ccacagggac cagagaatat accatcgcta     420
gactcctctt tcacagcatt gcacatgaag aatcataaat ctctgtaggt ttataatcac     480
gttcgccctg ctttctaaca caattgttat ctccatcgtg gagacaacta acgttcatca     540
aggtatatat cttactacat cccattttc aattggatta ctcaataccg gtggtcgtac      600
attcgaggtg atttggttgc tgcgacaacc attgcgtcca tctatatccc tatggctttg     660
tccttatcct caaatctcgc ccacgcacct cctatcaatg gcctctactc ttttgtgatc     720
aacccttttca tctatgcgat cttcgggagc agcccgctgt taatagtggg cccagaagca     780
gcaggctcct tgcttactgg cacgattgtc aaaactagtg tcagaccagg cccatctggt     840
gaggacgacg aagtagcgaa tgccatcgtg gtcggcatag ccactgcaat ggcgggcgcc     900
atgatactga tcgctgggct tacacggctg ggatttctgg acaatgtgct gagccggccc     960
tttcttaggg gtttcattac agcgatcggt tttgtgattt tgtggatca actcatcccc     1020
gaagtcggat tgaccgagct agcaaaggaa gctggtgtta cccatgggac tacagttgac    1080
aagctcatgt tccttataag aaacatagga ggttgccatg cgcttacaac cgcggtggct    1140
tttgggagct ttgctattat aatggtattt cggttagtgt tggtgactcg gaagcctggt    1200
gcttagactg attaccatta caggactctc aagaaaatgc tccagccgcg gtatcctcag    1260
gtgatttatc ttccggaccg aattctcgta gttattcttt cagccgtcct gacatggcat    1320
cttggttggg atgacaaagg gttggagatt cttgggccct tgaaacaaaa tgccaatggc    1380
cttttttgcgt tcaaatggcc tttccagttt agccagatga agcatgtacg cgctgcaatg    1440
agtacttctt tcgtcatcgc gttacttggc tttttcgagt cttctgttgc cgccaaggga    1500
cttagtggcg aggccagaca agaaggtgtc cagggaatgc ctgtcagtgc taacagagag    1560
atggtggcgc tgggtcttgc taatactgtg gggggctgtt tcatggcgct tcctgcgttt    1620
ggtggctatg caagaagcaa agtcaacgct tcaactggag ctcggtctcc gatgagcagc    1680
attttcctga gcattattac ctttgtttgt atcatggtgc ttttgccgta cttatactat    1740
cttccggtga gtctcgaccc caaatacttc cgagcgaagg ctgagaaaat atgttgcaat    1800
aattcagaaa gccgttcttt cttctatgat atctgtcgtc gcattcagtc tcattgaaga    1860
atgtcctcac gacgtggctt tctttatccg actgcgcgga tggacggagc tagccctaat    1920
```

```
gcttctcatc tttgtctcga ctatttctta ttctctagag ctgggaattg cccttggtat   1980
tggcctttct atcttgatcc ttattcgcca ttctacgcag cctcggatcc aaattctggg   2040
taagatagca ggcactaccg accgtttcga taacgctgaa ctccaccccg agagcgttga   2100
gttaatcgaa ggcgcgctta ttgttaagat cccggaaccg ctcacctttg ccaatactgg   2160
tgagctcaag aatcgtcttc ggcggttgga attatatggc agtagccgag cgcacccttc   2220
tcttcccccc acgcgcaccc ccgaacataa caagaatatt atatttgatg ttcatggtgt   2280
tactagcatc gatggttccg gtacgcaagt cttatatgag attgtggacg atatgcaga   2340 ccaggggtc agcgtcttct tctgccgcgt cgcaactcgc aatgttttcc gcatgtttga   2400
acgaagtgga attgtggaac gatgcggtgg gataacgcac ttcgttcatg gtgtcgacga   2460
agccctccgc cttgccgaat cggaagacga gattgaaatc tga                    2503
```

<210> SEQ ID NO 2
<211> LENGTH: 770
<212> TYPE: PRT
<213> ORGANISM: Aspergillus oryzae

<400> SEQUENCE: 2

```
Met Glu Ser Ser Ala Val Gln Glu Pro Thr Gln Gln Arg Ser Leu Arg
1               5                   10                  15

Asp Arg Ile Phe Asn Leu Phe Arg Thr Ser Ser Ser Asn Asp Ala Pro
            20                  25                  30

Gly Leu Pro Ala Arg Leu Val Thr Ala Glu Ser Ala Ala Gln Asn Glu
        35                  40                  45

Gly Ser Ala Leu Ile Tyr Pro Pro Arg Glu Pro Asp Ala Arg Thr Arg
    50                  55                  60

Leu Leu Glu Ser Tyr Asp Arg Gly Glu Arg Gly Leu Arg Asn Ser Gly
65                  70                  75                  80

Val His Gly Thr Phe Ser Ser Arg Pro Glu Gln Glu Glu Ile Gln Lys
                85                  90                  95

Trp Asp Ala Ser Ser Leu Gln Asn Ala Gly Asn Glu Glu Arg Ser Gln
            100                 105                 110

Ser Pro Gly Gly Ala Asp Gly His Ile Gly Ser Pro Gly Asp Val Ser
        115                 120                 125

Gly Tyr Pro Gln Gly Pro Glu Asn Ile Pro Ser Leu Asp Ser Ser Phe
    130                 135                 140

Thr Ala Leu His Met Lys Asn His Lys Ser Leu Tyr Ile Ser Tyr Tyr
145                 150                 155                 160

Ile Pro Phe Phe Asn Trp Ile Thr Gln Tyr Arg Trp Ser Tyr Ile Arg
                165                 170                 175

Gly Asp Leu Val Ala Ala Thr Thr Ile Ala Ser Ile Tyr Ile Pro Met
            180                 185                 190

Ala Leu Ser Leu Ser Ser Asn Leu Ala His Ala Pro Ile Asn Gly
        195                 200                 205

Leu Tyr Ser Phe Val Ile Asn Pro Phe Ile Tyr Ala Ile Phe Gly Ser
    210                 215                 220

Ser Pro Leu Leu Ile Val Gly Pro Glu Ala Ala Gly Ser Leu Leu Thr
225                 230                 235                 240

Gly Thr Ile Val Lys Thr Ser Val Arg Pro Gly Pro Ser Gly Glu Asp
                245                 250                 255

Asp Glu Val Ala Asn Ala Ile Val Val Gly Ile Ala Thr Ala Met Ala
            260                 265                 270
```

```
Gly Ala Met Ile Leu Ile Ala Gly Leu Thr Arg Leu Gly Phe Leu Asp
            275                 280                 285

Asn Val Leu Ser Arg Pro Phe Leu Arg Gly Phe Ile Thr Ala Ile Gly
    290                 295                 300

Phe Val Ile Phe Val Asp Gln Leu Ile Pro Glu Val Gly Leu Thr Glu
305                 310                 315                 320

Leu Ala Lys Glu Ala Gly Val Thr His Gly Thr Thr Val Asp Lys Leu
                325                 330                 335

Met Phe Leu Ile Arg Asn Ile Gly Gly Cys His Ala Leu Thr Thr Ala
                340                 345                 350

Val Ala Phe Gly Ser Phe Ala Ile Ile Met Val Phe Arg Thr Leu Lys
            355                 360                 365

Lys Met Leu Gln Pro Arg Tyr Pro Gln Val Ile Tyr Leu Pro Asp Arg
    370                 375                 380

Ile Leu Val Val Ile Leu Ser Ala Val Leu Thr Trp His Leu Gly Trp
385                 390                 395                 400

Asp Asp Lys Gly Leu Glu Ile Leu Gly Pro Leu Lys Gln Asn Ala Asn
                405                 410                 415

Gly Leu Phe Ala Phe Lys Trp Pro Phe Gln Phe Ser Met Lys His
                420                 425                 430

Val Arg Ala Ala Met Ser Thr Ser Phe Val Ile Ala Leu Leu Gly Phe
            435                 440                 445

Phe Glu Ser Ser Val Ala Ala Lys Gly Leu Ser Gly Glu Ala Arg Gln
    450                 455                 460

Glu Gly Val Gln Gly Met Pro Val Ser Ala Asn Arg Glu Met Val Ala
465                 470                 475                 480

Leu Gly Leu Ala Asn Thr Val Gly Gly Cys Phe Met Ala Leu Pro Ala
                485                 490                 495

Phe Gly Tyr Ala Arg Ser Lys Val Asn Ala Ser Thr Gly Ala Arg
                500                 505                 510

Ser Pro Met Ser Ser Ile Phe Leu Ser Ile Ile Thr Phe Val Cys Ile
            515                 520                 525

Met Val Leu Leu Pro Tyr Leu Tyr Tyr Leu Pro Lys Ala Val Leu Ser
    530                 535                 540

Ser Met Ile Ser Val Val Ala Phe Ser Leu Ile Glu Glu Cys Pro His
545                 550                 555                 560

Asp Val Ala Phe Phe Ile Arg Leu Arg Gly Trp Thr Glu Leu Ala Leu
                565                 570                 575

Met Leu Leu Ile Phe Val Ser Thr Ile Phe Tyr Ser Leu Glu Leu Gly
                580                 585                 590

Ile Ala Leu Gly Ile Gly Leu Ser Ile Leu Ile Leu Ile Arg His Ser
            595                 600                 605

Thr Gln Pro Arg Ile Gln Ile Leu Gly Lys Ile Ala Gly Thr Thr Asp
    610                 615                 620

Arg Phe Asp Asn Ala Glu Leu His Pro Glu Ser Val Glu Leu Ile Glu
625                 630                 635                 640

Gly Ala Leu Ile Val Lys Ile Pro Glu Pro Leu Thr Phe Ala Asn Thr
                645                 650                 655

Gly Glu Leu Lys Asn Arg Leu Arg Arg Leu Glu Leu Tyr Gly Ser Ser
                660                 665                 670

Arg Ala His Pro Ser Leu Pro Pro Thr Arg Thr Pro Glu His Asn Lys
            675                 680                 685
```

```
Asn Ile Ile Phe Asp Val His Gly Val Thr Ser Ile Asp Gly Ser Gly
    690                 695                 700
Thr Gln Val Leu Tyr Glu Ile Val Asp Gly Tyr Ala Asp Gln Gly Val
705                 710                 715                 720
Ser Val Phe Phe Cys Arg Val Ala Thr Arg Asn Val Phe Arg Met Phe
                725                 730                 735
Glu Arg Ser Gly Ile Val Glu Arg Cys Gly Gly Ile Thr His Phe Val
            740                 745                 750
His Gly Val Asp Glu Ala Leu Arg Leu Ala Glu Ser Glu Asp Glu Ile
        755                 760                 765
Glu Ile
    770

<210> SEQ ID NO 3
<211> LENGTH: 2657
<212> TYPE: DNA
<213> ORGANISM: Aspergillus oryzae

<400> SEQUENCE: 3
```

| | | | | |
|---|---|---|---|---|
| atgccgggcg atctcaaaac caaaattggt cacggcgcgg ccaaggcctt ggggatcaag | 60 |
| atcccctacc gtgatcctct cggagttcat gctgacccag tcacacgagg cgagtcgatg | 120 |
| ttctccgtcg aacgatcga cacatactcc tatctcgagc ccgaacccac tcccgctgaa | 180 |
| tggctgaagg aagtctgccc tagctggcat caggtgggcc gttattttta caaccttttc | 240 |
| cctttcctct cgtggattac gaggtacaac ttgcaatggt tgctgggaga tatgattgcc | 300 |
| ggtaagagcc tttccactgt gtttgatttg atcgacaagt agacaacata ctcattggaa | 360 |
| tgcaggcgtc acggtcggtg ctgtggtcgt tccgcaggga atggcctacg ctaaactggc | 420 |
| aaacctacct gtagagtatg gtctctattc ctcgttcatg ggtgttctca tttattggtt | 480 |
| ttttgccacc tcaaaggata tcaccattgg tgtaagtcat tctgcaccca tgtcagcatg | 540 |
| tatcttgcta atatagtatc ttccctgttc agccggtggc tgtcatgtct acccttacag | 600 |
| gtaagatagt tgccgaggcg caaacgaagc tcccagatgt cgaagggcat gtaatcgcct | 660 |
| cctgtttggc tatcatttgt ggagccgtgg tttgcgctat gggcctgctt cggctgggat | 720 |
| ttatcgtgga tttcattcct ctgccggcaa tttcagcttt catgacgggt ccgccatca | 780 |
| atatctgctc cggacaggtc aaagacatgc tgggagagac ggccgacttc tcgacgaaag | 840 |
| attctaccta tctggttatc atcaacaccc tcaagcatct tccctccgca aaaatcgatg | 900 |
| ccgccatggg tgtcagtgct ttagctatgc tgtacattat ccgttcgggt tgcaattatg | 960 |
| gcgcgaagaa gttcccccgt catgccaagg tttggttctt cgtttcgact tgcgcacag | 1020 |
| tgttcgtgat cttgttctat acgatgatca gtgccgctgt gaacttgcac cggcggtcta | 1080 |
| acccgcggtt caagctcctg ggtaaagttc ctcgtggttt ccaacatgcg gctgtccctc | 1140 |
| aggtaaattc gaggatcatc agcgcatttg ctagcgaact tcctgcttcg attattgtcc | 1200 |
| tgcttatcga acacatcgct atctcgaaat cctttggccg tgtcaacaac tacacaattg | 1260 |
| atccctctca ggagctggtt gctattggtg tgtcgaactt gcttggaccg ttccttggtg | 1320 |
| gttaccagc gactggatcg ttctcccgaa ctgcaatcaa atcgaaagcg ggtgtccgca | 1380 |
| ccccacttgc cggtgttatt actgcggttg ttgtcctcct cgccatttac gctctgcccg | 1440 |
| ctgtcttctt ttacatcccg aaagcttccc ttgctggtgt catcattcat gcagtcggtg | 1500 |
| acctcattac cccaccaaac accgtttacc agttctggcg cgtgtcccct ctggatgcga | 1560 |
| tcattttctt tatcggtgtt atcgtgactg tcttcaccac gattgagatc ggcatttact | 1620 |

```
gtaccgtttg tgtgtctgtt gccattctgc tgttccgcgt cgccaaggcc cgcggtcaat   1680
tcttaggaag agtcactatc cactcggtga tcggtgacca tctggtacag gatgatggga   1740
aatatgggtc tgccaactcc cctaatgctg ccagcgatga caaagatgaa ttgagccggt   1800
ctatcttctt gcctatcaac cacacggacg gatcgaatcc cgatgtcgag gtgcagcaac   1860
cttatcctgg tatcttcatc taccgattct cggaaggatt caactacccc aatgccaatc   1920
actacaccga ttatttggtc cagactatct tcaagcatac acgtcgcaca aatccgttct   1980
cctacggtaa accgggtgat cggccatgga ataatcctgg ccctcgcagg ggcaagtctg   2040
aagatgacga gtcgcatttg cccttactgc aggctgtcat tcttgacttc tcatccgtca   2100
acaatgttga tgtgaccctcg gtccagaacc tcatcgatgt ccgcaatcaa ctcgacctct   2160
acgcttcgcc taagactgtg cagtggcact tgctcatat taacaaccgc tggacgaaac   2220
gagcccttgc agcagcaggt ttcggcttcc catctccgga ctcggatgaa ggattccaga   2280
gatggaagcc aattttcagc gtggctgaga tcgaaggcag tgcctctgcc gcagctcatg   2340
cagagatggt gaacaacaga cacacccagc ataacatcaa gagcgaagac ctcgagcatg   2400
gcctcaagca cgattcagag accaccgagc gtgagacaca cggcatcgaa gaatcctccg   2460
atgccagcag caccccggagg acaagttgc aacgggacct gaaggatagc aaggcttacc   2520
gcagtcgccg aagggtcgct atggtgcagg gcctcaaccg gccattcttc cacatcgacc   2580
tgactagtgc actgcagagt gccttggcca acgcgggcga gcagccggac cctaaaatga   2640
atgtccttga tgcatag                                                 2657

<210> SEQ ID NO 4
<211> LENGTH: 843
<212> TYPE: PRT
<213> ORGANISM: Aspergillus oryzae

<400> SEQUENCE: 4

Met Pro Gly Asp Leu Lys Thr Lys Ile Gly His Gly Ala Ala Lys Ala
1               5                   10                  15

Leu Gly Ile Lys Ile Pro Tyr Arg Asp Pro Leu Gly Val His Ala Asp
            20                  25                  30

Pro Val Thr Arg Gly Glu Ser Met Phe Ser Val Gly Thr Ile Asp Thr
        35                  40                  45

Tyr Ser Tyr Leu Glu Pro Glu Pro Thr Pro Ala Glu Trp Leu Lys Glu
    50                  55                  60

Val Cys Pro Ser Trp His Gln Val Gly Arg Tyr Phe Tyr Asn Leu Phe
65                  70                  75                  80

Pro Phe Leu Ser Trp Ile Thr Arg Tyr Asn Leu Gln Trp Leu Leu Gly
                85                  90                  95

Asp Met Ile Ala Gly Val Thr Val Gly Ala Val Val Pro Gln Gly
            100                 105                 110

Met Ala Tyr Ala Lys Leu Ala Asn Leu Pro Val Glu Tyr Gly Leu Tyr
        115                 120                 125

Ser Ser Phe Met Gly Val Leu Ile Tyr Trp Phe Phe Ala Thr Ser Lys
    130                 135                 140

Asp Ile Thr Ile Gly Pro Val Ala Val Met Ser Thr Leu Thr Gly Lys
145                 150                 155                 160

Ile Val Ala Glu Ala Gln Thr Lys Leu Pro Asp Val Glu Gly His Val
                165                 170                 175

Ile Ala Ser Cys Leu Ala Ile Ile Cys Gly Ala Val Val Cys Ala Met
```

```
            180                 185                 190
Gly Leu Leu Arg Leu Gly Phe Ile Val Asp Phe Ile Pro Leu Pro Ala
            195                 200                 205
Ile Ser Ala Phe Met Thr Gly Ser Ala Ile Asn Ile Cys Ser Gly Gln
            210                 215                 220
Val Lys Asp Met Leu Gly Glu Thr Ala Asp Phe Ser Thr Lys Asp Ser
225                 230                 235                 240
Thr Tyr Leu Val Ile Ile Asn Thr Leu Lys His Leu Pro Ser Ala Lys
            245                 250                 255
Ile Asp Ala Ala Met Gly Val Ser Ala Leu Ala Met Leu Tyr Ile Ile
            260                 265                 270
Arg Ser Gly Cys Asn Tyr Gly Ala Lys Lys Phe Pro Arg His Ala Lys
            275                 280                 285
Val Trp Phe Phe Val Ser Thr Leu Arg Thr Val Phe Val Ile Leu Phe
            290                 295                 300
Tyr Thr Met Ile Ser Ala Ala Val Asn Leu His Arg Arg Ser Asn Pro
305                 310                 315                 320
Arg Phe Lys Leu Leu Gly Lys Val Pro Arg Gly Phe Gln His Ala Ala
            325                 330                 335
Val Pro Gln Val Asn Ser Arg Ile Ile Ser Ala Phe Ala Ser Glu Leu
            340                 345                 350
Pro Ala Ser Ile Ile Val Leu Leu Ile Glu His Ile Ala Ile Ser Lys
            355                 360                 365
Ser Phe Gly Arg Val Asn Asn Tyr Thr Ile Asp Pro Ser Gln Glu Leu
            370                 375                 380
Val Ala Ile Gly Val Ser Asn Leu Leu Gly Pro Phe Leu Gly Gly Tyr
385                 390                 395                 400
Pro Ala Thr Gly Ser Phe Ser Arg Thr Ala Ile Lys Ser Lys Ala Gly
            405                 410                 415
Val Arg Thr Pro Leu Ala Gly Val Ile Thr Ala Val Val Leu Leu
            420                 425                 430
Ala Ile Tyr Ala Leu Pro Ala Val Phe Phe Tyr Ile Pro Lys Ala Ser
            435                 440                 445
Leu Ala Gly Val Ile Ile His Ala Val Gly Asp Leu Ile Thr Pro Pro
            450                 455                 460
Asn Thr Val Tyr Gln Phe Trp Arg Val Ser Pro Leu Asp Ala Ile Ile
465                 470                 475                 480
Phe Phe Ile Gly Val Ile Val Thr Val Phe Thr Thr Ile Glu Ile Gly
            485                 490                 495
Ile Tyr Cys Thr Val Cys Val Ser Val Ala Ile Leu Leu Phe Arg Val
            500                 505                 510
Ala Lys Ala Arg Gly Gln Phe Leu Gly Arg Val Thr Ile His Ser Val
            515                 520                 525
Ile Gly Asp His Leu Val Gln Asp Asp Gly Lys Tyr Gly Ser Ala Asn
            530                 535                 540
Ser Pro Asn Ala Ala Ser Asp Asp Lys Asp Glu Leu Ser Arg Ser Ile
545                 550                 555                 560
Phe Leu Pro Ile Asn His Thr Asp Gly Ser Asn Pro Asp Val Glu Val
            565                 570                 575
Gln Gln Pro Tyr Pro Gly Ile Phe Ile Tyr Arg Phe Ser Glu Gly Phe
            580                 585                 590
Asn Tyr Pro Asn Ala Asn His Tyr Thr Asp Tyr Leu Val Gln Thr Ile
            595                 600                 605
```

```
Phe Lys His Thr Arg Arg Thr Asn Pro Phe Ser Tyr Gly Lys Pro Gly
    610                 615                 620

Asp Arg Pro Trp Asn Asn Pro Gly Pro Arg Arg Gly Lys Ser Glu Asp
625                 630                 635                 640

Asp Glu Ser His Leu Pro Leu Leu Gln Ala Val Ile Leu Asp Phe Ser
                645                 650                 655

Ser Val Asn Asn Val Asp Val Thr Ser Val Gln Asn Leu Ile Asp Val
            660                 665                 670

Arg Asn Gln Leu Asp Leu Tyr Ala Ser Pro Lys Thr Val Gln Trp His
        675                 680                 685

Phe Ala His Ile Asn Asn Arg Trp Thr Lys Arg Ala Leu Ala Ala Ala
    690                 695                 700

Gly Phe Gly Phe Pro Ser Pro Asp Ser Asp Glu Gly Phe Gln Arg Trp
705                 710                 715                 720

Lys Pro Ile Phe Ser Val Ala Glu Ile Glu Gly Ser Ala Ser Ala Ala
                725                 730                 735

Ala His Ala Glu Met Val Asn Asn Arg His Thr Gln His Asn Ile Lys
            740                 745                 750

Ser Glu Asp Leu Glu His Gly Leu Lys His Asp Ser Glu Thr Thr Glu
        755                 760                 765

Arg Glu Thr His Gly Ile Glu Glu Ser Asp Ala Ser Ser Thr Arg
    770                 775                 780

Glu Asp Lys Leu Gln Arg Asp Leu Lys Asp Ser Lys Ala Tyr Arg Ser
785                 790                 795                 800

Arg Arg Arg Val Ala Met Val Gln Gly Leu Asn Arg Pro Phe Phe His
                805                 810                 815

Ile Asp Leu Thr Ser Ala Leu Gln Ser Ala Leu Ala Asn Ala Gly Glu
            820                 825                 830

Gln Pro Asp Pro Lys Met Asn Val Leu Asp Ala
        835                 840

<210> SEQ ID NO 5
<211> LENGTH: 1257
<212> TYPE: DNA
<213> ORGANISM: Aspergillus aculeatus

<400> SEQUENCE: 5
atgcacgacc acagcactgg atctagtcca tacatctcgg acgtggaaac cttgaaccac      60
gcctgcgaga gtccgtcaa ccccgagacc aaagtctccc agcctcagga atctcccatt     120
atcagcaata tgaacatca ggagtttgtt aagctgggca tccgccaacg gctgcgtcat      180
ttcacctggg cctggtatac cctaaccatg agcgcaggtg gactggccct tcttctccgc    240
aaccagccgt atcaattcaa ggggttgaag gagataggcc tggtggtata catagccaat    300
ctcgtcttct ttactatcat cggctctctt atgatcacca ggtttgttct ttacaacaac    360
ctgatggact ctctccgcca cgaccgagaa ggtttcttct ttccaacctt ctggctctcc    420
atcgccacca tgattagtgg tctatctgcc tacttctcta ctgaagacac gcaccgcctc    480
aattatgctc tcgagggtct cttctgggcg tactgtatct tcacgtttgc ctcagcagtg    540
atccagtact cctttgtctt ctcctatcac acgttccctc tgcaaactat gatgccatca    600
tggatcttac cggcattccc tatcatgctg agcggaacca ttgcctctgc cgcttccagc    660
taccagcctg cggtgtctgc cacgccatg attgttgccg gcatcacgtt ccagggactc    720
ggattctgca tcagcttcat gatgtacgcc cactacatcg ggcgtctgat ggagacgggc    780
```

-continued

```
atcccttcga gcgagcaccg tcctggtatg ttcatctgtg tcggcccccc tgccttcacg    840
ctgctggcta tcatcggcat ggccaacggc cttcccgagg gcttcagtat cctgggcgat    900
ggtggcatgg acgaccgtca catcatgcga gtactggccg tctgcgcggg catgttcctc    960
tgggctctga gcatttggtt cttctgtgtc gctctgggct cagttgtgcg ggcgcctccc   1020
catgatttcc acctcaactg gtgggctatg gtcttcccta acaccggact cactctcgcc   1080
accatcaccc tggccaagtc actggacagt gccgcgttga aatgggtggg cgtgggcatg   1140
tccctctgcg tgatctgcat gttcatcttc gtcttcgtga gcaccattag gctgttctc    1200 ttgaagagga tcatgtggcc aggtcgggat gaggatgtgt ccgagttgtt cgaatga      1257
```

<210> SEQ ID NO 6
<211> LENGTH: 418
<212> TYPE: PRT
<213> ORGANISM: Aspergillus aculeatus

<400> SEQUENCE: 6

```
Met His Asp His Ser Thr Gly Ser Ser Pro Tyr Ile Ser Asp Val Glu
1               5                   10                  15

Thr Leu Asn His Ala Cys Glu Lys Ser Val Asn Pro Glu Ala Lys Val
            20                  25                  30

Ser Gln Pro Gln Glu Ser Pro Ile Ile Ser Asn Asn Glu His Gln Glu
        35                  40                  45

Phe Val Lys Leu Gly Ile Arg Gln Arg Leu Arg His Phe Thr Trp Ala
    50                  55                  60

Trp Tyr Thr Leu Thr Met Ser Ala Gly Gly Leu Ala Leu Leu Leu Arg
65                  70                  75                  80

Asn Gln Pro Tyr Gln Phe Lys Gly Leu Lys Glu Ile Gly Leu Val Val
                85                  90                  95

Tyr Ile Ala Asn Leu Val Phe Phe Thr Ile Gly Ser Leu Met Ile
            100                 105                 110

Thr Arg Phe Val Leu Tyr Asn Asn Leu Met Asp Ser Leu Arg His Asp
        115                 120                 125

Arg Glu Gly Phe Phe Pro Thr Phe Trp Leu Ser Ile Ala Thr Met
    130                 135                 140

Ile Ser Gly Leu Ser Ala Tyr Phe Ser Thr Glu Asp Thr His Arg Leu
145                 150                 155                 160

Asn Tyr Ala Leu Glu Gly Leu Phe Trp Ala Tyr Cys Ile Phe Thr Phe
                165                 170                 175

Ala Ser Ala Val Ile Gln Tyr Ser Phe Val Phe Ser Tyr His Thr Phe
            180                 185                 190

Pro Leu Gln Thr Met Met Pro Ser Trp Ile Leu Pro Ala Phe Pro Ile
        195                 200                 205

Met Leu Ser Gly Thr Ile Ala Ser Ala Ser Ser Tyr Gln Pro Ala
    210                 215                 220

Val Ser Ala Thr Pro Met Ile Val Ala Gly Ile Thr Phe Gln Gly Leu
225                 230                 235                 240

Gly Phe Cys Ile Ser Phe Met Tyr Ala His Tyr Ile Gly Arg Leu
                245                 250                 255

Met Glu Thr Gly Ile Pro Ser Ser Glu His Arg Pro Gly Met Phe Ile
            260                 265                 270

Cys Val Gly Pro Pro Ala Phe Thr Leu Leu Ala Ile Ile Gly Met Ala
        275                 280                 285
```

Asn Gly Leu Pro Glu Gly Phe Ser Ile Leu Gly Asp Gly Gly Met Asp
    290                 295                 300

Asp Arg His Ile Met Arg Val Leu Ala Val Cys Ala Gly Met Phe Leu
305                 310                 315                 320

Trp Ala Leu Ser Ile Trp Phe Phe Cys Val Ala Leu Gly Ser Val Val
                325                 330                 335

Arg Ala Pro Pro His Asp Phe His Leu Asn Trp Trp Ala Met Val Phe
            340                 345                 350

Pro Asn Thr Gly Leu Thr Leu Ala Thr Ile Thr Leu Ala Lys Ser Leu
        355                 360                 365

Asp Ser Ala Ala Leu Lys Trp Val Gly Val Gly Met Ser Leu Cys Val
370                 375                 380

Ile Cys Met Phe Ile Phe Val Phe Val Ser Thr Val Arg Ala Val Leu
385                 390                 395                 400

Leu Lys Arg Ile Met Trp Pro Gly Arg Asp Glu Asp Val Ser Glu Leu
                405                 410                 415

Phe Glu

<210> SEQ ID NO 7
<211> LENGTH: 1430
<212> TYPE: DNA
<213> ORGANISM: Aspergillus oryzae

<400> SEQUENCE: 7

```
atggtcaaag ctggtgagtt agcaatcctt aacagatgac actctcatag gtactaactc      60
gaaacgttag cggtacttgg agcttctggt ggcattggcc aggtatggat atccccacgc     120
cttacaaccc tggtcacaat atgaccttgt cgatactga ctatctccca agccactgtc     180
tctcctgttg aagacctgtc ccttagttga agagcttgct ctctacgatg ttgtgaacac     240
ccctggtgtt gctgctgatc tatcccacat ctcgtctatc gctgtacgtt actgccacaa     300
tgcgaattgc ccgatggaag aggcgaaaaa tggtatcttg cttacctggg cgattagaaa     360
atctctggtt ttctgcccaa agatgatggg ctgaagcagg cccttactgg tgctaatatt     420
gttgtcatcc cggctggtat tccccgtaag tccctaccct ttcgcattgc tcctcgtatg     480
ttcgctggtg ccagttttc tgatagttga taggcaagcc tggtatgacc cgtgacgacc     540
tcttcaagat caacgccggc atagtgcgag acttggtcaa gggtatcgcc gagttctgcc     600
ccaaggcctt tgttctggtt atctcaaacc ccgttaattc tactgttcct attgctgcag     660
aggtgctcaa agccgctggc gtctttgacc gaagcgcct ctttggtgtc accacactgg     720
acgtcgttcg tgcagagact ttcacccaag agttctcggg ccagaaggat ccttctgctg     780
ttcaaatccc agttgttggt ggccactctg gagagaccat tgtcccctc ttcagcaaga     840
ctaccccgc aattcagata cccgaggaga gtatgacgc actgatccac cgtaggttgt     900
cccaaagaat ctcatgaata tcttgctgta agcactaact atgcttcagg cgtccaattt     960
ggtggagatg aggtggtcca agctaaggac ggtgctggtt ccgccacctt gtctatggcc    1020
tatgccggtt acaggtaggg atgctgcgta ccgtgagagc actcgcggct aacatgccat    1080
aggttcgctg agagtgtaat caaagcttca aagggtcaaa cggtattgt cgagcctacc    1140
ttcgtctacc tgcctggaat tcccggcggt gatgagatcg ttaaggcaac tggcgtggaa    1200
ttcttctcta ctcttgtaac cttaggagta agattcatct cctcacagaa tcttcgttca    1260
tatcacgcca ggctaacgct attaaacaga ctaatgcgc agagaaggct agcaacgttc    1320
ttgagggcgt gaccgagaag gaaaagaagc ttctcgaggc ttgcacgaaa ggccttaagg    1380
```
gtaatatcga gaaaggcatc gacttcgtta agaacccacc accaaagtaa                  1430

<210> SEQ ID NO 8
<211> LENGTH: 330
<212> TYPE: PRT
<213> ORGANISM: Aspergillus oryzae

<400> SEQUENCE: 8

Met Val Lys Ala Ala Val Leu Gly Ala Ser Gly Gly Ile Gly Gln Pro
1               5                   10                  15

Leu Ser Leu Leu Leu Lys Thr Cys Pro Leu Val Glu Glu Leu Ala Leu
            20                  25                  30

Tyr Asp Val Val Asn Thr Pro Gly Val Ala Ala Asp Leu Ser His Ile
        35                  40                  45

Ser Ser Ile Ala Lys Ile Ser Gly Phe Leu Pro Lys Asp Asp Gly Leu
    50                  55                  60

Lys Gln Ala Leu Thr Gly Ala Asn Ile Val Ile Pro Ala Gly Ile
65                  70                  75                  80

Pro Arg Lys Pro Gly Met Thr Arg Asp Asp Leu Phe Lys Ile Asn Ala
                85                  90                  95

Gly Ile Val Arg Asp Leu Val Lys Gly Ile Ala Glu Phe Cys Pro Lys
            100                 105                 110

Ala Phe Val Leu Val Ile Ser Asn Pro Val Asn Ser Thr Val Pro Ile
        115                 120                 125

Ala Ala Glu Val Leu Lys Ala Ala Gly Val Phe Asp Pro Lys Arg Leu
    130                 135                 140

Phe Gly Val Thr Thr Leu Asp Val Val Arg Ala Glu Thr Phe Thr Gln
145                 150                 155                 160

Glu Phe Ser Gly Gln Lys Asp Pro Ser Ala Val Gln Ile Pro Val Val
                165                 170                 175

Gly Gly His Ser Gly Glu Thr Ile Val Pro Leu Phe Ser Lys Thr Thr
            180                 185                 190

Pro Ala Ile Gln Ile Pro Glu Glu Lys Tyr Asp Ala Leu Ile His Arg
        195                 200                 205

Val Gln Phe Gly Gly Asp Glu Val Val Gln Ala Lys Asp Gly Ala Gly
    210                 215                 220

Ser Ala Thr Leu Ser Met Ala Tyr Ala Gly Tyr Arg Phe Ala Glu Ser
225                 230                 235                 240

Val Ile Lys Ala Ser Lys Gly Gln Thr Gly Ile Val Glu Pro Thr Phe
                245                 250                 255

Val Tyr Leu Pro Gly Ile Pro Gly Gly Asp Glu Ile Val Lys Ala Thr
            260                 265                 270

Gly Val Glu Phe Phe Ser Thr Leu Val Thr Leu Gly Thr Asn Gly Ala
        275                 280                 285

Glu Lys Ala Ser Asn Val Leu Glu Gly Val Thr Glu Lys Glu Lys
    290                 295                 300

Leu Leu Glu Ala Cys Thr Lys Gly Leu Lys Gly Asn Ile Glu Lys Gly
305                 310                 315                 320

Ile Asp Phe Val Lys Asn Pro Pro Lys
                325                 330

<210> SEQ ID NO 9
<211> LENGTH: 3643
<212> TYPE: DNA
<213> ORGANISM: Aspergillus oryzae

<400> SEQUENCE: 9

```
atggcggctc cgtttcgtca gcctgaggag gcggtcgatg acaccgagtt catcgatgac      60
caccatgaac acctccgtga taccgtgcac catcggttgc gcgccaattc ctccattatg     120
cacttccaga agatcctcgt cgccaaccgt ggtgagatcc ccattcgtat cttcagaacg     180
gcccacgagc tgtcattgca gacggttgct atctactctc atgaggatcg actgtcaatg     240
caccgtcaaa aggccgatga ggcctacatg attggccacc gcggtcagta caccctgtc      300
ggtgcgtacc tggcgggcga tgagatcatc aagatcgccc tggagcacgg tgtccagctg     360
atccaccgg gctacggttt cttgtccgag aacgccgact cgcccgcaa ggttgagaac       420
gccggcattg tctttgtggg acccactccc gataccattg acagcttggg tgacaaggtg     480
tcggcccgtc ggctggccat taagtgcgag gtccctgtcg ttccgggtac ggagggcccc     540
gtcgagcgct atgaggaggt caaggcgttc acagacacct atggcttccc catcatcatc    600
aaggctgcct ttggcggtgg tggccgtggt atgcgtgtgg tccgtgacca ggccgagctg     660
cgtgactcgt tcgagcgagc cacctctgag gcccgctccg ccttcggcaa tggtaccgtc     720
ttcgtcgagc gcttcctcga caaacccaag cacattgaag tccagcttct gggtgacagc     780
cacggcaacg ttgtccatct gttttgagcgt gactgctccg tgcagcgtcg tcaccagaag    840
gtcgttgagg ttgctccggc taaggacctg ccagccgatg tccgggaccg catcctggcc    900
gatgctgtga agctggccaa gtccgtcaac taccgtaacg ccggtacagc tgagttcctg    960
gtggaccagc agaaccgcca ctacttcatt gaaatcaatc tcgtatcca agtcgagcac     1020
accatcaccg aagagattac tggtatcgat atcgtggctg cacagatcca gattgctgct    1080
ggtgcaagcc tcgagcaact gggcctgact caggaccgca tctccgcccg cggatttgcc    1140
attcaatgtc gtatcaccac ggaagatccc gccaaggggt tctctccgga tactggtaag   1200
attgaggttt atcgttccgc tggtggtaac ggtgtccgtc tggatggtgg taacggtttc   1260
gctggtgcta tcatcacccc tcactacgac tccatgctgg tcaagtgtac ctgccgtggt   1320
tcgacctatg aaatcgctcg tcgcaaggtt gtgcgtgcct tggtcgagtt ccgtattcgt   1380
ggtgtgaaga ccaacattcc cttcctgact tcgcttctga gccacccgac cttcgtcgat   1440
ggaaactgct ggaccacttt catcgacgac acccctgaat tgttctctct tgtcggcagt   1500
cagaaccgtg cccagaagct gctcgcatac ctcggcgatg tagctgtcaa cggtagtagc   1560
atcaagggcc aaattggcga gcccaagctc aagggtgatg tcatcaagcc gaagcttttc   1620
gatgccgagg gcaagccgct tgacgttccc gcccctgca ccaagggttg gaagcagatt    1680
ctggaccggg agggcccggc tgcctttgcg aaggccgtgc gtgccaacaa gggttgcttg   1740
atcatggata ctacctggcg tgacgcccac cagtctttgc tggccacccg tgtgcgtacc   1800
atcgacttgt tgaacatcgc ccatgagacc agctacgcct actccaatgc gtacagtttg   1860
gaatgctggg gtggtgctac cttcgatgtg gccatgcgtt tcctctatga ggaccctgg    1920
gaccgcctgc gcaagatgcg taaggctgtt cctaacatcc cattccagat gttgctccgt   1980
ggtgccaacg tgtcgcccta ctcttccctc ccagacaacg ccatctacca cttctgtaag   2040
caggctaaga agtgcggtgt cgacattttc cgtgttttcg acgccctcaa cgatgtcgat   2100
cagctcgagg tcggtatcaa ggctgttcat gctgccgagg gtgttgtcga ggccaccatg   2160
tgctacagcg gtgacatgct gaaccccac aagaagtaca acctggagta ctacatggcc    2220
ttggtggata agattgtagc catgaagcct cacatccttg gtatcaagga tatggccggt   2280
```

```
gtgctgaagc cccaggccgc tcgcctgttg gtgggctcca tccgtcagcg ctaccctgac    2340
cttcccatcc acgtcacac ccacgactcc gctggtactg gtgtagcttc catgattgcc     2400
tgtgcccagg cgggtgccga cgccgtggac gccgcgaccg acagcatgtc cggtatgacc    2460
tcccagccta gcattggtgc cattctggcc tctcttgagg cactgagca agaccccggt     2520 ctcaacctcg cccacgtgcg cgctattgat agctactggg cacagctgcg cttgctctac    2580
tctcctttcg aggcgggtct cactggcccc gaccctgagg tctacgagca cgagatccct    2640
ggtggtcagt tgaccaacct tatcttccag gccagtcagc tcggcttggg ccagcagtgg    2700
gccgaaacca agaaggccta tgaggcggct aatgatttac tcggcgacat tgtaaaggtc    2760
actcccacct ccaaggtggt cggtgacttg gctcagttca tggtctcgaa caaactgact    2820
ccggaggatg ttgttgagcg tgctggtgag ctggacttcc ctggttctgt gctcgaattc    2880
ctcgaaggtc tcatgggaca gcccttcggt ggattccccg agccattgcg ctcccgcgcc    2940
ctgcgcgatc gccgcaagct cgagaagcgt ccaggtctct acctcgagcc tttggatttg    3000
gctaagatca agagccagat ccgtgagaag ttcggtgctg ctactgagta tgacgtggcc    3060
agctatgcca tgtatcccaa ggtcttcgag gactacaaga agttcgtcca gaagttcggt    3120
gatctctccg tcttgcccac acggtacttc ttggccaagc tgagattgg cgaggagttc     3180 cacgttgagc tggagaaggg taaggtgctc atcctgaagt tgttggccat cggccctctt    3240
tcagagcaga ctggtcagcg tgaggtcttc tacgaagtca acggtgaggt gcgccaggtc    3300
gctgttgatg acaacaaggc ttccgtggac aacacttcac gccctaaggc cgatgtgggt    3360
gacagcagcc aggtcggtgc tcctatgagc ggtgtggttg ttgaaatccg tgtccacgat    3420
ggtctggagg ttaagaaggg tgacccactt gccgtcctga gtgccatgaa gatggtaagt    3480
tcattccgaa tcatttttct cactggtcaa ctacagatgc taacagctta tccaggaaat    3540
ggttatctct gctcctcaca gtggaaaggt ctccagcttg ctggtcaagg agggcgattc    3600 tgtgatggc caggatctcg tctgcaagat cgtcaaagcg taa                        3643
```

<210> SEQ ID NO 10
<211> LENGTH: 1193
<212> TYPE: PRT
<213> ORGANISM: Aspergillus oryzae

<400> SEQUENCE: 10

Met Ala Ala Pro Phe Arg Gln Pro Glu Glu Ala Val Asp Asp Thr Glu
1               5                   10                  15

Phe Ile Asp Asp His His Glu His Leu Arg Asp Thr Val His Arg
            20                  25                  30

Leu Arg Ala Asn Ser Ser Ile Met His Phe Gln Lys Ile Leu Val Ala
        35                  40                  45

Asn Arg Gly Glu Ile Pro Ile Arg Ile Phe Arg Thr Ala His Glu Leu
    50                  55                  60

Ser Leu Gln Thr Val Ala Ile Tyr Ser His Glu Asp Arg Leu Ser Met
65                  70                  75                  80

His Arg Gln Lys Ala Asp Glu Ala Tyr Met Ile Gly His Arg Gly Gln
                85                  90                  95

Tyr Thr Pro Val Gly Ala Tyr Leu Ala Gly Asp Glu Ile Ile Lys Ile
            100                 105                 110

Ala Leu Glu His Gly Val Gln Leu Ile His Pro Gly Tyr Gly Phe Leu
        115                 120                 125

Ser Glu Asn Ala Asp Phe Ala Arg Lys Val Glu Asn Ala Gly Ile Val

```
            130                 135                 140
Phe Val Gly Pro Thr Pro Asp Thr Ile Asp Ser Leu Gly Asp Lys Val
145                 150                 155                 160

Ser Ala Arg Arg Leu Ala Ile Lys Cys Glu Val Pro Val Val Pro Gly
                165                 170                 175

Thr Glu Gly Pro Val Glu Arg Tyr Glu Val Lys Ala Phe Thr Asp
                180                 185                 190

Thr Tyr Gly Phe Pro Ile Ile Ile Lys Ala Ala Phe Gly Gly Gly Gly
                195                 200                 205

Arg Gly Met Arg Val Val Arg Asp Gln Ala Glu Leu Arg Asp Ser Phe
210                 215                 220

Glu Arg Ala Thr Ser Glu Ala Arg Ser Ala Phe Gly Asn Gly Thr Val
225                 230                 235                 240

Phe Val Glu Arg Phe Leu Asp Lys Pro Lys His Ile Glu Val Gln Leu
                245                 250                 255

Leu Gly Asp Ser His Gly Asn Val Val His Leu Phe Glu Arg Asp Cys
                260                 265                 270

Ser Val Gln Arg Arg His Gln Lys Val Val Glu Val Ala Pro Ala Lys
                275                 280                 285

Asp Leu Pro Ala Asp Val Arg Asp Arg Ile Leu Ala Asp Ala Val Lys
290                 295                 300

Leu Ala Lys Ser Val Asn Tyr Arg Asn Ala Gly Thr Ala Glu Phe Leu
305                 310                 315                 320

Val Asp Gln Gln Asn Arg His Tyr Phe Ile Glu Ile Asn Pro Arg Ile
                325                 330                 335

Gln Val Glu His Thr Ile Thr Glu Glu Ile Thr Gly Ile Asp Ile Val
                340                 345                 350

Ala Ala Gln Ile Gln Ile Ala Ala Gly Ala Ser Leu Glu Gln Leu Gly
                355                 360                 365

Leu Thr Gln Asp Arg Ile Ser Ala Arg Gly Phe Ala Ile Gln Cys Arg
                370                 375                 380

Ile Thr Thr Glu Asp Pro Ala Lys Gly Phe Ser Pro Asp Thr Gly Lys
385                 390                 395                 400

Ile Glu Val Tyr Arg Ser Ala Gly Gly Asn Gly Val Arg Leu Asp Gly
                405                 410                 415

Gly Asn Gly Phe Ala Gly Ala Ile Ile Thr Pro His Tyr Asp Ser Met
                420                 425                 430

Leu Val Lys Cys Thr Cys Arg Gly Ser Thr Tyr Glu Ile Ala Arg Arg
                435                 440                 445

Lys Val Val Arg Ala Leu Val Glu Phe Arg Ile Arg Gly Val Lys Thr
                450                 455                 460

Asn Ile Pro Phe Leu Thr Ser Leu Leu Ser His Pro Thr Phe Val Asp
465                 470                 475                 480

Gly Asn Cys Trp Thr Thr Phe Ile Asp Asp Thr Pro Glu Leu Phe Ser
                485                 490                 495

Leu Val Gly Ser Gln Asn Arg Ala Gln Lys Leu Leu Ala Tyr Leu Gly
                500                 505                 510

Asp Val Ala Val Asn Gly Ser Ser Ile Lys Gly Gln Ile Gly Glu Pro
                515                 520                 525

Lys Leu Lys Gly Asp Val Ile Lys Pro Lys Leu Phe Asp Ala Glu Gly
530                 535                 540

Lys Pro Leu Asp Val Ser Ala Pro Cys Thr Lys Gly Trp Lys Gln Ile
545                 550                 555                 560
```

```
Leu Asp Arg Glu Gly Pro Ala Ala Phe Ala Lys Ala Val Arg Ala Asn
            565                 570                 575

Lys Gly Cys Leu Ile Met Asp Thr Thr Trp Arg Asp Ala His Gln Ser
            580                 585                 590

Leu Leu Ala Thr Arg Val Arg Thr Ile Asp Leu Leu Asn Ile Ala His
            595                 600                 605

Glu Thr Ser Tyr Ala Tyr Ser Asn Ala Tyr Ser Leu Glu Cys Trp Gly
            610                 615                 620

Gly Ala Thr Phe Asp Val Ala Met Arg Phe Leu Tyr Glu Asp Pro Trp
625                 630                 635                 640

Asp Arg Leu Arg Lys Met Arg Lys Ala Val Pro Asn Ile Pro Phe Gln
            645                 650                 655

Met Leu Leu Arg Gly Ala Asn Gly Val Ala Tyr Ser Ser Leu Pro Asp
            660                 665                 670

Asn Ala Ile Tyr His Phe Cys Lys Gln Ala Lys Lys Cys Gly Val Asp
            675                 680                 685

Ile Phe Arg Val Phe Asp Ala Leu Asn Asp Val Asp Gln Leu Glu Val
            690                 695                 700

Gly Ile Lys Ala Val His Ala Ala Glu Gly Val Val Glu Ala Thr Met
705                 710                 715                 720

Cys Tyr Ser Gly Asp Met Leu Asn Pro His Lys Lys Tyr Asn Leu Glu
            725                 730                 735

Tyr Tyr Met Ala Leu Val Asp Lys Ile Val Ala Met Lys Pro His Ile
            740                 745                 750

Leu Gly Ile Lys Asp Met Ala Gly Val Leu Lys Pro Gln Ala Ala Arg
            755                 760                 765

Leu Leu Val Gly Ser Ile Arg Gln Arg Tyr Pro Asp Leu Pro Ile His
            770                 775                 780

Val His Thr His Asp Ser Ala Gly Thr Gly Val Ala Ser Met Ile Ala
785                 790                 795                 800

Cys Ala Gln Ala Gly Ala Asp Ala Val Asp Ala Ala Thr Asp Ser Met
            805                 810                 815

Ser Gly Met Thr Ser Gln Pro Ser Ile Gly Ala Ile Leu Ala Ser Leu
            820                 825                 830

Glu Gly Thr Glu Gln Asp Pro Gly Leu Asn Leu Ala His Val Arg Ala
            835                 840                 845

Ile Asp Ser Tyr Trp Ala Gln Leu Arg Leu Leu Tyr Ser Pro Phe Glu
            850                 855                 860

Ala Gly Leu Thr Gly Pro Asp Pro Glu Val Tyr Glu His Glu Ile Pro
865                 870                 875                 880

Gly Gly Gln Leu Thr Asn Leu Ile Phe Gln Ala Ser Gln Leu Gly Leu
            885                 890                 895

Gly Gln Gln Trp Ala Glu Thr Lys Lys Ala Tyr Glu Ala Ala Asn Asp
            900                 905                 910

Leu Leu Gly Asp Ile Val Lys Val Thr Pro Thr Ser Lys Val Val Gly
            915                 920                 925

Asp Leu Ala Gln Phe Met Val Ser Asn Lys Leu Thr Pro Glu Asp Val
            930                 935                 940

Val Glu Arg Ala Gly Glu Leu Asp Phe Pro Gly Ser Val Leu Glu Phe
945                 950                 955                 960

Leu Glu Gly Leu Met Gly Gln Pro Phe Gly Gly Phe Pro Glu Pro Leu
            965                 970                 975
```

Arg Ser Arg Ala Leu Arg Asp Arg Lys Leu Glu Lys Arg Pro Gly
            980                 985                 990

Leu Tyr Leu Glu Pro Leu Asp Leu Ala Lys Ile Lys Ser Gln Ile Arg
        995                 1000                1005

Glu Lys Phe Gly Ala Ala Thr Glu Tyr Asp Val Ala Ser Tyr Ala
    1010                1015                1020

Met Tyr Pro Lys Val Phe Glu Asp Tyr Lys Lys Phe Val Gln Lys
    1025                1030                1035

Phe Gly Asp Leu Ser Val Leu Pro Thr Arg Tyr Phe Leu Ala Lys
    1040                1045                1050

Pro Glu Ile Gly Glu Glu Phe His Val Glu Leu Glu Lys Gly Lys
    1055                1060                1065

Val Leu Ile Leu Lys Leu Leu Ala Ile Gly Pro Leu Ser Glu Gln
    1070                1075                1080

Thr Gly Gln Arg Glu Val Phe Tyr Glu Val Asn Gly Glu Val Arg
    1085                1090                1095

Gln Val Ala Val Asp Asp Asn Lys Ala Ser Val Asp Asn Thr Ser
    1100                1105                1110

Arg Pro Lys Ala Asp Val Gly Asp Ser Ser Gln Val Gly Ala Pro
    1115                1120                1125

Met Ser Gly Val Val Val Glu Ile Arg Val His Asp Gly Leu Glu
    1130                1135                1140

Val Lys Lys Gly Asp Pro Leu Ala Val Leu Ser Ala Met Lys Met
    1145                1150                1155

Glu Met Val Ile Ser Ala Pro His Ser Gly Lys Val Ser Ser Leu
    1160                1165                1170

Leu Val Lys Glu Gly Asp Ser Val Asp Gly Gln Asp Leu Val Cys
    1175                1180                1185

Lys Ile Val Lys Ala
    1190

<210> SEQ ID NO 11
<211> LENGTH: 40
<212> TYPE: DNA
<213> ORGANISM: Aspergillus oryzae

<400> SEQUENCE: 11
gtgatagaac atcgtccata atggaatcca gcgctgtaca                            40

<210> SEQ ID NO 12
<211> LENGTH: 40
<212> TYPE: DNA
<213> ORGANISM: Aspergillus oryzae

<400> SEQUENCE: 12
gtgtcagtca cctctagtta tcagatttca atctcgtctt                            40

<210> SEQ ID NO 13
<211> LENGTH: 20
<212> TYPE: DNA
<213> ORGANISM: Aspergillus oryzae

<400> SEQUENCE: 13
gaacaggaag aaatccaaaa                                                  20

<210> SEQ ID NO 14
<211> LENGTH: 20
<212> TYPE: DNA

<213> ORGANISM: Aspergillus oryzae

<400> SEQUENCE: 14
gtcggcatag ccactgcaat                                        20

<210> SEQ ID NO 15
<211> LENGTH: 20
<212> TYPE: DNA
<213> ORGANISM: Aspergillus oryzae

<400> SEQUENCE: 15
tgttgccgcc aagggactta                                        20

<210> SEQ ID NO 16
<211> LENGTH: 20
<212> TYPE: DNA
<213> ORGANISM: Aspergillus oryzae

<400> SEQUENCE: 16
ccgagagcgt tgagttaatc                                        20

<210> SEQ ID NO 17
<211> LENGTH: 20
<212> TYPE: DNA
<213> ORGANISM: Aspergillus oryzae

<400> SEQUENCE: 17
agcattaggg ctagctccgt                                        20

<210> SEQ ID NO 18
<211> LENGTH: 20
<212> TYPE: DNA
<213> ORGANISM: Aspergillus oryzae

<400> SEQUENCE: 18
ccaagatgcc atgtcaggac                                        20

<210> SEQ ID NO 19
<211> LENGTH: 20
<212> TYPE: DNA
<213> ORGANISM: Aspergillus oryzae

<400> SEQUENCE: 19
tcacaaaaga gtagaggcca                                        20

<210> SEQ ID NO 20
<211> LENGTH: 36
<212> TYPE: DNA
<213> ORGANISM: Aspergillus oryzae

<400> SEQUENCE: 20
tgtgatagaa catcgtccat aatgcacgac cacagc                      36

<210> SEQ ID NO 21
<211> LENGTH: 40
<212> TYPE: DNA
<213> ORGANISM: Aspergillus oryzae

<400> SEQUENCE: 21
gtgtcagtca cctctagtta tcattcgaac aactcggaca                  40

<210> SEQ ID NO 22
<211> LENGTH: 36

```
<212> TYPE: DNA
<213> ORGANISM: Aspergillus oryzae

<400> SEQUENCE: 22
agaacatcgt ccataatggt caaagctggt gagtta                                 36

<210> SEQ ID NO 23
<211> LENGTH: 40
<212> TYPE: DNA
<213> ORGANISM: Aspergillus oryzae

<400> SEQUENCE: 23
gtgtcagtca cctctagtta ttactttggt ggtgggttct                             40

<210> SEQ ID NO 24
<211> LENGTH: 36
<212> TYPE: DNA
<213> ORGANISM: Aspergillus oryzae

<400> SEQUENCE: 24
tagaacatcg tccataatgg cggctccgtt tcgtca                                 36

<210> SEQ ID NO 25
<211> LENGTH: 40
<212> TYPE: DNA
<213> ORGANISM: Aspergillus oryzae

<400> SEQUENCE: 25
gtgtcagtca cctctagtta ttattacgct ttgacgatct                             40

<210> SEQ ID NO 26
<211> LENGTH: 1143
<212> TYPE: DNA
<213> ORGANISM: Aspergillus oryzae

<400> SEQUENCE: 26
atgctgacac ctcccaagtt tgaggatgag aagcagctgg gccccgtggg tatccgggag       60
aggcttcgcc atttcacttg ggcctggtac acattaacga tgagtggagg agggctggcc      120
gtcctcatca tcagccagcc cttttgggtt cgcggattga gagagatcgg catcgctgtc      180
tatatcctca acctgatcct cttcgccctt gtctgctcta ccatggctat aaggttcatc      240
ctgcacggca accttctgga gtccctccgt catgaccgcg agggtctctt cttcccgacc      300
ttctggctct ccgtcgcaac catcatctgc ggcttgtctc gctacttcgg tgaagaatcg      360
aatgagtcct ccaactagc cctcgaagcc ctcttctgga tctactgcgt ctgcacctta       420
ctcgtcgcaa tcatccaata ctcgttcgtc ttctcatccc acaagtacgg ccttcaaacc      480
atgatgcctt catggatcct tccagccttc cccatcatgc tcagcggcac catcgcctcc      540
gtcatcggtg aacaacaacc cgctcgcgca gccctcccca tcatcggcgc cggcgtcacc      600
ttccagggcc tcggcttctc catcagcttc atgatgtacg cccactacat cggccgactg      660
atggagtccg gcctccccca cagcgaccac agaccaggca tgttcatctg cgtcggaccc      720
cccgccttca cagccctcgc cctcgtcggc atgagcaaag gcctccccga agacttcaag      780
ctgctccacg acgccacgc cctggaagat ggccgcatca tcgagctgct ggccatctcc       840
gccggcgtct tcctctgggc cctgagtctc tggttcttct gcatcgccat tgtcgccgtc      900
atccgctcgc ccccgaggc cttccacctc aactggtggg ccatggtctt ccccaacacc      960
ggcttcaccc tggccaccat caccctgggc aaggctctca acagtaacgg cgtgaagggc     1020
```

```
gtcggctccg ccatgtctat ctgcatcgtg tgcatgtaca tcttcgtctt tgtcaacaat   1080
gtccgcgccg ttatccggaa ggatatcatg tacccgggta agatgagga tgtatctgat   1140 tag                                                                 1143
```

<210> SEQ ID NO 27
<211> LENGTH: 380
<212> TYPE: PRT
<213> ORGANISM: Aspergillus oryzae

<400> SEQUENCE: 27

```
Met Leu Thr Pro Pro Lys Phe Glu Asp Glu Lys Gln Leu Gly Pro Val
1               5                   10                  15

Gly Ile Arg Glu Arg Leu Arg His Phe Thr Trp Ala Trp Tyr Thr Leu
            20                  25                  30

Thr Met Ser Gly Gly Leu Ala Val Leu Ile Ser Gln Pro Phe
        35                  40                  45

Gly Phe Arg Gly Leu Arg Glu Ile Gly Ile Ala Val Tyr Ile Leu Asn
    50                  55                  60

Leu Ile Leu Phe Ala Leu Val Cys Ser Thr Met Ala Ile Arg Phe Ile
65                  70                  75                  80

Leu His Gly Asn Leu Leu Glu Ser Leu Arg His Asp Arg Glu Gly Leu
                85                  90                  95

Phe Phe Pro Thr Phe Trp Leu Ser Val Ala Thr Ile Ile Cys Gly Leu
            100                 105                 110

Ser Arg Tyr Phe Gly Glu Glu Ser Asn Glu Ser Phe Gln Leu Ala Leu
        115                 120                 125

Glu Ala Leu Phe Trp Ile Tyr Cys Val Cys Thr Leu Leu Val Ala Ile
    130                 135                 140

Ile Gln Tyr Ser Phe Val Phe Ser Ser His Lys Tyr Gly Leu Gln Thr
145                 150                 155                 160

Met Met Pro Ser Trp Ile Leu Pro Ala Phe Pro Ile Met Leu Ser Gly
                165                 170                 175

Thr Ile Ala Ser Val Ile Gly Glu Gln Gln Pro Ala Arg Ala Ala Leu
            180                 185                 190

Pro Ile Ile Gly Ala Gly Val Thr Phe Gln Gly Leu Gly Phe Ser Ile
        195                 200                 205

Ser Phe Met Met Tyr Ala His Tyr Ile Gly Arg Leu Met Glu Ser Gly
    210                 215                 220

Leu Pro His Ser Asp His Arg Pro Gly Met Phe Ile Cys Val Gly Pro
225                 230                 235                 240

Pro Ala Phe Thr Ala Leu Ala Leu Val Gly Met Ser Lys Gly Leu Pro
                245                 250                 255

Glu Asp Phe Lys Leu Leu His Asp Ala His Ala Leu Glu Asp Gly Arg
            260                 265                 270

Ile Ile Glu Leu Leu Ala Ile Ser Ala Gly Val Phe Leu Trp Ala Leu
        275                 280                 285

Ser Leu Trp Phe Phe Cys Ile Ala Ile Val Ala Val Ile Arg Ser Pro
    290                 295                 300

Pro Glu Ala Phe His Leu Asn Trp Trp Ala Met Val Phe Pro Asn Thr
305                 310                 315                 320

Gly Phe Thr Leu Ala Thr Ile Thr Leu Gly Lys Ala Leu Asn Ser Asn
                325                 330                 335

Gly Val Lys Gly Val Gly Ser Ala Met Ser Ile Cys Ile Val Cys Met
            340                 345                 350
```

Tyr Ile Phe Val Phe Val Asn Asn Val Arg Ala Val Ile Arg Lys Asp
            355                 360                 365

Ile Met Tyr Pro Gly Lys Asp Glu Asp Val Ser Asp
    370                 375                 380

<210> SEQ ID NO 28
<211> LENGTH: 1182
<212> TYPE: DNA
<213> ORGANISM: Aspergillus terreus

<400> SEQUENCE: 28

| | | | | | |
|---|---|---|---|---|---|
| atgtttgaga | acactgcccc | tccagggagc | tcccgctccg | actctggcat | cctggaccat | 60 |
| gaattcgaga | agcagccggg | ttccgtgggc | atgcgtgaac | gcatccgcca | ttttacctgg | 120 |
| gcctggtata | ctctcacaat | gagtgctggt | ggcttggccc | tcctccttgg | gagccagcca | 180 |
| aacaccttca | ccggcctgag | ggagattgga | ctcgccgtgt | acctgctcaa | cctgctcttc | 240 |
| tttgccctgg | tctgctcgac | catggccggc | cggttcatcc | tgcacggagg | gctggtcgac | 300 |
| tctctccggc | acgaacgcga | gggcatcttc | ttcccaacct | tctggctctc | gatcgccacc | 360 |
| atcatcacag | gcctgtaccg | ctacttcggc | gaagacgccg | gacgcccctt | cgtgctcgcc | 420 |
| ctcgaagccc | tcttctggat | ctactgcgct | tgcaccctcc | tcgtcgccgt | catccaatac | 480 |
| tcctggctct | ctccggccc | caaataccgc | tccaaaccg | ccatgcccgg | ctggatcctc | 540 |
| cccgccttcc | ctgtcatgct | ctctggcacc | atcgcctccg | tcatcgccga | gcagcagccg | 600 |
| gcccgcgccg | ccatccccat | catcgtcgcc | ggcaccacct | tccagggcct | gggcttctcc | 660 |
| atcagcatga | tcatgtacgc | ccactacgtc | ggccgcctca | tggagtccgg | cctgccgtgc | 720 |
| cgcgagcacc | gccgggcat | gttcatcgcc | gtcggcccgc | cggctttcac | ggcgctggcc | 780 |
| ctcgtcggca | tgaccaaggg | gctcccgcac | gacttccagc | tcatcggcga | tgacttcgcc | 840 |
| ttcgaggatg | cccgcatcct | gcagctgctg | gcgatcgccg | tcggcgtgtt | ctctgggcg | 900 |
| ctgagtctgt | ggttcttttg | cattgcggcc | attgccgtcg | tgcgctcccc | gccaacggcc | 960 |
| ttccacctga | gctggtgggc | catggtcttc | cccaacacgg | gcttcacccT | cgccacgatc | 1020 |
| aacctgggta | cggccctcaa | gagcgagggt | atccagggtg | tggggacggc | catgtcgatt | 1080 |
| ggaattgtgt | ctattttctt | gtttgtgttt | atcagccatg | tgcgggctgt | catcaggaaa | 1140 |
| gacattatgt | atcctgggaa | agacgaggat | gtggtggagt | aa | | 1182 |

<210> SEQ ID NO 29
<211> LENGTH: 393
<212> TYPE: PRT
<213> ORGANISM: Aspergillus terreus

<400> SEQUENCE: 29

Met Phe Glu Asn Thr Ala Pro Pro Gly Ser Ser Arg Ser Asp Ser Gly
1               5                   10                  15

Ile Leu Asp His Glu Phe Glu Lys Gln Pro Gly Ser Val Gly Met Arg
            20                  25                  30

Glu Arg Ile Arg His Phe Thr Trp Ala Trp Tyr Thr Leu Thr Met Ser
        35                  40                  45

Ala Gly Gly Leu Ala Leu Leu Gly Ser Gln Pro Asn Thr Phe Thr
    50                  55                  60

Gly Leu Arg Glu Ile Gly Leu Ala Val Tyr Leu Leu Asn Leu Leu Phe
65                  70                  75                  80

Phe Ala Leu Val Cys Ser Thr Met Ala Gly Arg Phe Ile Leu His Gly

|  |  |  |  | 85 |  |  |  |  | 90 |  |  |  |  | 95 |  |
|---|---|---|---|---|---|---|---|---|---|---|---|---|---|---|---|

Gly Leu Val Asp Ser Leu Arg His Glu Arg Glu Gly Ile Phe Phe Pro
           100               105              110

Thr Phe Trp Leu Ser Ile Ala Thr Ile Ile Thr Gly Leu Tyr Arg Tyr
         115              120             125

Phe Gly Glu Asp Ala Gly Arg Pro Phe Val Leu Ala Leu Glu Ala Leu
   130              135              140

Phe Trp Ile Tyr Cys Ala Cys Thr Leu Val Ala Val Ile Gln Tyr
145              150            155                160

Ser Trp Leu Phe Ser Gly Pro Lys Tyr Arg Leu Gln Thr Ala Met Pro
         165              170             175

Gly Trp Ile Leu Pro Ala Phe Pro Val Met Leu Ser Gly Thr Ile Ala
           180              185             190

Ser Val Ile Ala Glu Gln Gln Pro Ala Arg Ala Ala Ile Pro Ile Ile
         195              200             205

Val Ala Gly Thr Thr Phe Gln Gly Leu Gly Phe Ser Ile Ser Met Ile
   210              215              220

Met Tyr Ala His Tyr Val Gly Arg Leu Met Glu Ser Gly Leu Pro Cys
225              230            235                240

Arg Glu His Arg Pro Gly Met Phe Ile Ala Val Gly Pro Pro Ala Phe
         245              250             255

Thr Ala Leu Ala Leu Val Gly Met Thr Lys Gly Leu Pro His Asp Phe
           260              265             270

Gln Leu Ile Gly Asp Asp Phe Ala Phe Glu Asp Ala Arg Ile Leu Gln
         275              280             285

Leu Leu Ala Ile Ala Val Gly Val Phe Leu Trp Ala Leu Ser Leu Trp
   290              295              300

Phe Phe Cys Ile Ala Ala Ile Ala Val Val Arg Ser Pro Pro Thr Ala
305              310            315                320

Phe His Leu Ser Trp Trp Ala Met Val Phe Pro Asn Thr Gly Phe Thr
         325              330             335

Leu Ala Thr Ile Asn Leu Gly Thr Ala Leu Lys Ser Glu Gly Ile Gln
           340              345             350

Gly Val Gly Thr Ala Met Ser Ile Gly Ile Val Ser Ile Phe Leu Phe
         355              360             365

Val Phe Ile Ser His Val Arg Ala Val Ile Arg Lys Asp Ile Met Tyr
   370              375              380

Pro Gly Lys Asp Glu Asp Val Val Glu
385              390

<210> SEQ ID NO 30
<211> LENGTH: 1317
<212> TYPE: DNA
<213> ORGANISM: Schizosaccharomyces pombe

<400> SEQUENCE: 30

```
atgggagaat tgaaggaaat tctcaagcag cgctaccatg aattgctcga ctggaacgtc    60
aaagcacccc acgtccctct ctcgcagagg ttgaagcatt tcacatggtc gtggttcgcg   120
tgtacgatgg caaccggtgg cgtcggactc atcatcggat ccttcccttt ccgattctac   180
ggactcaaca cgatcggcaa gattgtgtac atcctccaga ttttcctctt ctccttgttc   240
ggctcgtgta tgctcttcag gttcatcaag tatccgtcca caatcaagga ctcctggaac   300
catcatctcg agaaactctt cattgcgact tgtctcctct cgatttcgac attcatcgat   360
```

```
atgttggcga tctacgccta ccccgacaca ggcgagtgga tggtgtgggt catccgaatc      420
ctctactaca tctacgtcgc ggtctccttc atttactgtg tgatggcgtt cttcacgatc      480
ttcaacaacc acgtctatac cattgaaacc gcctcgcctg catggatcct ccctatcttc      540
cctccgatga tctgtggtgt cattgccggt gcggtgaact ccacccagcc tgcgcaccag      600
ctcaaaaaca tggtgatttt cggaatcctc ttccagggat tgggtttctg gtctacttg       660 ctcttgttcg cagtcaacgt gctccggttc ttcacggtcg gcttggcaaa gcccaggac       720 cgacctggca tgttcatgtt cgtgggacct cctgcgttct ccggcttggc actcatcaac      780
atcgcgaggg gtgccatggg ctcgaggccg tacatcttcg tgggagcaaa ctcctcggaa      840
tacttgggtt tcgtgtcgac gttcatggcg atttcatct ggggcttggc agcatggtgt       900
tattgtctcg ccatggtgtc cttcctcgca ggcttcttca cacgcgcacc tttgaagttc      960
gcgtgtggtt ggttcgcatt catcttcccc aacgtgggct tcgtgaactg tacgattgag     1020
atcggcaaga tgatcgactc caaagccttc cagatgttcg ccacattat cggtgtcatc      1080 ctctgtatcc agtggatttt gctcatgtat ttgatggtgc gtgcgttctt ggtcaacgac     1140
ttgtgttatc ccggtaaaga cgaggacgcc catccgcctc ccaaacccaa cacaggcgtc     1200
ctcaacccca ccttccctcc cgaaaaagca cctgcctccc tcgaaaaagt cgatacacat     1260
gtcacttcca ctggcggaga gtcggatcct ccgtcctccg aacacgagtc ggtctaa       1317
```

<210> SEQ ID NO 31
<211> LENGTH: 1317
<212> TYPE: DNA
<213> ORGANISM: Schizosaccharomyces pombe

<400> SEQUENCE: 31

```
atgggtgaac tcaaggaaat cttgaaacag aggtatcatg agttgcttga ctggaatgtc       60
aaagcccctc atgtccctct cagtcaacga ctgaagcatt ttacatggtc ttggttttgca     120 tgtactatgg caactggtgg tgttggtttg attattggtt cttcccctt tcgattttat       180 ggtcttaata caattggcaa aattgtttat attcttcaaa tcttttttgtt ttctctcttt     240 ggatcatgca tgctttttcg ctttattaaa tatccttcaa ctatcaagga ttcctggaac     300
catcatttgg aaaagctttt cattgctact tgtcttcttt caatatccac gttcatcgac     360
atgcttgcca tatacgccta tcctgatacc ggcgagtgga tggtgtgggt cattcgaatc     420
ctttattaca tttacgttgc agtatccttt atatactgcg taatggcttt ttttacaatt     480
ttcaacaacc atgtatatac cattgaaacc gcatctcctg cttggattct tcctattttc     540
cctcctatga tttgtggtgt cattgctggc gccgtcaatt ctacacaacc cgctcatcaa     600
ttaaaaaata tggttatctt tggtatcctc tttcaaggac ttggttttg gtttatctt       660 ttactgtttg ccgtcaatgt cttacggttt tttactgtag gcctggcaaa accccaagat     720
cgacctggta tgtttatgtt tgtcggtcca ccagctttct caggtttggc cttaattaat     780
attgcgcgtg gtgctatggg cagtcgccct tatatttttg ttggcgccaa ctcatccgag     840
tatcttggtt ttgtttctac ctttatggct attttttattt ggggtcttgc tgcttggtgt    900
tactgtctcg ccatggttag cttttttagcg ggcttttttca ctcgagcccc tctcaagttt    960
gcttgtggat ggtttgcatt catttttcccc aacgtgggtt ttgttaattg taccattgag    1020
ataggtaaaa tgatagattc caaagctttc caaatgtttg acatatcat tgggtcatt     1080 cttttgtattc agtggatcct cctaatgtat ttaatggtcc gtgcgtttct cgtcaatgat    1140
ctttgctatc ctggcaaaga cgaagatgcc catcctccac caaaaccaaa tacaggtgtc    1200
```

```
cttaaccctc ccttcccacc tgaaaaagca cctgcatctt tggaaaaagt cgatacacat    1260
gtcacatcta ctggtggtga atcggatcct cctagtagtg aacatgaaag cgtttaa       1317
```

<210> SEQ ID NO 32
<211> LENGTH: 438
<212> TYPE: PRT
<213> ORGANISM: Schizosaccharomyces pombe

<400> SEQUENCE: 32

```
Met Gly Glu Leu Lys Glu Ile Leu Lys Gln Arg Tyr His Glu Leu Leu
1               5                   10                  15

Asp Trp Asn Val Lys Ala Pro His Val Pro Leu Ser Gln Arg Leu Lys
            20                  25                  30

His Phe Thr Trp Ser Trp Phe Ala Cys Thr Met Ala Thr Gly Gly Val
        35                  40                  45

Gly Leu Ile Ile Gly Ser Phe Pro Phe Arg Phe Tyr Gly Leu Asn Thr
    50                  55                  60

Ile Gly Lys Ile Val Tyr Ile Leu Gln Ile Phe Leu Phe Ser Leu Phe
65                  70                  75                  80

Gly Ser Cys Met Leu Phe Arg Phe Ile Lys Tyr Pro Ser Thr Ile Lys
                85                  90                  95

Asp Ser Trp Asn His His Leu Glu Lys Leu Phe Ile Ala Thr Cys Leu
            100                 105                 110

Leu Ser Ile Ser Thr Phe Ile Asp Met Leu Ala Ile Tyr Ala Tyr Pro
        115                 120                 125

Asp Thr Gly Glu Trp Met Val Trp Val Ile Arg Ile Leu Tyr Tyr Ile
    130                 135                 140

Tyr Val Ala Val Ser Phe Ile Tyr Cys Val Met Ala Phe Phe Thr Ile
145                 150                 155                 160

Phe Asn Asn His Val Tyr Thr Ile Glu Thr Ala Ser Pro Ala Trp Ile
                165                 170                 175

Leu Pro Ile Phe Pro Pro Met Ile Cys Gly Val Ile Ala Gly Ala Val
            180                 185                 190

Asn Ser Thr Gln Pro Ala His Gln Leu Lys Asn Met Val Ile Phe Gly
        195                 200                 205

Ile Leu Phe Gln Gly Leu Gly Phe Trp Val Tyr Leu Leu Leu Phe Ala
    210                 215                 220

Val Asn Val Leu Arg Phe Phe Thr Val Gly Leu Ala Lys Pro Gln Asp
225                 230                 235                 240

Arg Pro Gly Met Phe Met Phe Val Gly Pro Pro Ala Phe Ser Gly Leu
                245                 250                 255

Ala Leu Ile Asn Ile Ala Arg Gly Ala Met Gly Ser Arg Pro Tyr Ile
            260                 265                 270

Phe Val Gly Ala Asn Ser Ser Glu Tyr Leu Gly Phe Val Ser Thr Phe
        275                 280                 285

Met Ala Ile Phe Ile Trp Gly Leu Ala Ala Trp Cys Tyr Cys Leu Ala
    290                 295                 300

Met Val Ser Phe Leu Ala Gly Phe Phe Thr Arg Ala Pro Leu Lys Phe
305                 310                 315                 320

Ala Cys Gly Trp Phe Ala Phe Ile Phe Pro Asn Val Gly Phe Val Asn
                325                 330                 335

Cys Thr Ile Glu Ile Gly Lys Met Ile Asp Ser Lys Ala Phe Gln Met
            340                 345                 350
```

```
Phe Gly His Ile Ile Gly Val Ile Leu Cys Ile Gln Trp Ile Leu Leu
            355                 360                 365
Met Tyr Leu Met Val Arg Ala Phe Leu Val Asn Asp Leu Cys Tyr Pro
        370                 375                 380
Gly Lys Asp Glu Asp Ala His Pro Pro Lys Pro Asn Thr Gly Val
385                 390                 395                 400
Leu Asn Pro Thr Phe Pro Pro Glu Lys Ala Pro Ala Ser Leu Glu Lys
            405                 410                 415
Val Asp Thr His Val Thr Ser Thr Gly Gly Glu Ser Asp Pro Pro Ser
        420                 425                 430
Ser Glu His Glu Ser Val
        435

<210> SEQ ID NO 33
<211> LENGTH: 1194
<212> TYPE: DNA
<213> ORGANISM: Aspergillus aculeatus

<400> SEQUENCE: 33
atgctcgggc aacatccgcc tcccgacacc tcctgctcgg accttacaac ataccagcat     60
gagctcaaag cctccaaata ctctagttcc accaatgtgt ctctacggga ccgtctgcgt    120
cattttacct gggcgtggta tactctgact atgagcaccg gcggtctagc cctcctgctg    180
gccagccagc cctactcctt ctccggactg caacagatcg gcttgcagt ctacatcatc    240
aacctggcct tctttgcgtt gctgtgtagc ctcatggccg cacgcttcat tctccacggc    300
aacttcctcg actccctccg acacgaccgc gagggtcttt tctttcctac tttctggctt    360
tctattgcaa ctatcatcac cggcctgtac cgctacttcg gcgacaccac acagcctgca    420
ttcatttacg ctcttgaggt gctcttctgg ctctactgtg ccttcactct gatgaccgct    480
attatccaat actcctttgt ctttaccgcc caccactacc ctctacaaac gatgatgccc    540
tcatggatcc tccccgcatt ccctatcatg ctcagcggca cgatcgcctc cgtcattgcc    600
gaacagcagc ccgcgcgctc tgctattccc atgatcgtcg ccggcaccac cttccaaggc    660
cttggcttct ccatcagttt cctcatgtac gcgcactata tcgggcggct catggagacg    720
ggccttccgt cccgggaaca ccgacccggg atgttcatct gcgttggccc ccggctttc     780
acggcccttg ccctaatcgg catgaccaac ggccttcctg aggattttca agtccttcaa    840
gacccgcacc cctttcaaga cgcgcacatc ctccgactcc ttgccatcgc cacgggcgcc    900
ttcctctggg ccctcagtct ctggttctt agcattgcca tcatcgccac catccgcctc    960
ccacctacag ccttccacct caactggtgg gccatggttt tccaaacac gggttttact   1020
ctcgcgacca tcacgctggg caaagccttc gatagccctg agtcaaggg cgtcggatct   1080
gccatgtcca tttgcatcgt ggggatgtgg ctgttcgtgt ttgcgagcaa tatccgtgcc   1140
gttgtcaaac gggatattgt tttccctggg aaggacgagg atgtatcgga gtaa         1194

<210> SEQ ID NO 34
<211> LENGTH: 397
<212> TYPE: PRT
<213> ORGANISM: Aspergillus aculeatus

<400> SEQUENCE: 34

Met Leu Gly Gln His Pro Pro Asp Thr Ser Cys Ser Asp Leu Thr
1               5                  10                  15
Thr Tyr Gln His Glu Leu Lys Ala Ser Lys Tyr Ser Ser Ser Thr Asn
            20                  25                  30
```

Val Ser Leu Arg Asp Arg Leu Arg His Phe Thr Trp Ala Trp Tyr Thr
         35                  40                  45

Leu Thr Met Ser Thr Gly Gly Leu Ala Leu Leu Ala Ser Gln Pro
 50                  55                  60

Tyr Ser Phe Ser Gly Leu Gln Gln Ile Gly Leu Ala Val Tyr Ile Ile
 65                  70                  75                  80

Asn Leu Ala Phe Phe Ala Leu Leu Cys Ser Leu Met Ala Ala Arg Phe
                 85                  90                  95

Ile Leu His Gly Asn Phe Leu Asp Ser Leu Arg His Asp Arg Glu Gly
                 100                 105                 110

Leu Phe Phe Pro Thr Phe Trp Leu Ser Ile Ala Thr Ile Ile Thr Gly
             115                 120                 125

Leu Tyr Arg Tyr Phe Gly Asp Thr Thr Gln Pro Ala Phe Ile Tyr Ala
         130                 135                 140

Leu Glu Val Leu Phe Trp Leu Tyr Cys Ala Phe Thr Leu Met Thr Ala
145                 150                 155                 160

Ile Ile Gln Tyr Ser Phe Val Phe Thr Ala His His Tyr Pro Leu Gln
                 165                 170                 175

Thr Met Met Pro Ser Trp Ile Leu Pro Ala Phe Pro Ile Met Leu Ser
             180                 185                 190

Gly Thr Ile Ala Ser Val Ile Ala Glu Gln Gln Pro Ala Arg Ser Ala
         195                 200                 205

Ile Pro Met Ile Val Ala Gly Thr Thr Phe Gln Gly Leu Gly Phe Ser
    210                 215                 220

Ile Ser Phe Leu Met Tyr Ala His Tyr Ile Gly Arg Leu Met Glu Thr
225                 230                 235                 240

Gly Leu Pro Ser Arg Glu His Arg Pro Gly Met Phe Ile Cys Val Gly
                 245                 250                 255

Pro Pro Ala Phe Thr Ala Leu Ala Leu Ile Gly Met Thr Asn Gly Leu
             260                 265                 270

Pro Glu Asp Phe Gln Val Leu Gln Asp Pro His Pro Phe Gln Asp Ala
         275                 280                 285

His Ile Leu Arg Leu Leu Ala Ile Ala Thr Gly Ala Phe Leu Trp Ala
    290                 295                 300

Leu Ser Leu Trp Phe Phe Ser Ile Ala Ile Ala Thr Ile Arg Leu
305                 310                 315                 320

Pro Pro Thr Ala Phe His Leu Asn Trp Trp Ala Met Val Phe Pro Asn
                 325                 330                 335

Thr Gly Phe Thr Leu Ala Thr Ile Thr Leu Gly Lys Ala Phe Asp Ser
             340                 345                 350

Pro Gly Val Lys Gly Val Gly Ser Ala Met Ser Ile Cys Ile Val Gly
         355                 360                 365

Met Trp Leu Phe Val Phe Ala Ser Asn Ile Arg Ala Val Val Lys Arg
370                 375                 380

Asp Ile Val Phe Pro Gly Lys Asp Glu Asp Val Ser Glu
385                 390                 395

<210> SEQ ID NO 35
<211> LENGTH: 1194
<212> TYPE: DNA
<213> ORGANISM: Aspergillus aculeatus

<400> SEQUENCE: 35
atgctcgggc aacactcgcc tcccggcacc tcctgctcgg accttacaac ataccaacat      60

-continued

```
gagcttaaag cctccaaata ctctagttcc accaatgtgt ctctacggga ccgtctgcgt      120 catttacct gggcctggta tactctgact atgagcaccg gcggcctagc gcttctgctg       180
gccagccagc cctacacctt ctccggactg caacagatcg ggcttgcagt ctatatcatc     240
aacctggtct tcttttgcttt gctgtgcagc ctcatggcca cgcgcttcat tctccacggc    300
aacttcctcg actccctccg acacgaccgc gagggtcttt tctttcccac tttctggctt     360
tccattgcaa ctatcatcac cggactctac cgctacttcg gcgacaccac acagcctgca     420
ttcatttacg cccttgaggt gcttttctgg ctctactgtg ccttcacact gatgaccgct     480
atcatccaat actcttttgt ctttactgcc caccactacc ctctacaaac gatgatgccc     540
tcgtggatcc tccccgcatt ccccatcatg ctaagcggca cgatcgcctc tgtcattgcc     600
gaacagcagc ccgcgcgctc tgctattccc atgatcgtcg ccggcaccac cttccaaggc    660
cttggcttct ccatcagttt cctcatgtac gcgcactata tcggacgcct catggagacg    720
ggccttccgt cccgggaaca ccgacccggg atgttcatct gcgttggccc ccctgctttc    780
acggcccttg ccctaatcgg catgaccaac ggccttcctg aggattttca agtccttcaa    840
gacccgcacc cctttcaaga cgcgcatatc ctccgactcc ttgccatcgc acgggcgcc    900 ttcctctggg ccctcagtct ctggttcttc agcattgcca ttatcgccac catccgcctc    960
ccacctacgg cttccacct caactggtgg gccatggttt ttccaaacac gggttttact    1020
ctcgcgacca tcacgctggg caaagccttc gatagccctg gagtcaaggg cgtcggatct   1080
gccatgtcca tttgcatcgt ggggatgtgg ctgttcgtgt ttgcgagcaa tatccgcgcc   1140
gttgtcaaac gggatattgt gtttcctggc aaggacgagg atgtatcgga gtaa         1194
```

<210> SEQ ID NO 36
<211> LENGTH: 397
<212> TYPE: PRT
<213> ORGANISM: Aspergillus aculeatus

<400> SEQUENCE: 36

```
Met Leu Gly Gln His Ser Pro Pro Gly Thr Ser Cys Ser Asp Leu Thr
1               5                   10                  15

Thr Tyr Gln His Glu Leu Lys Ala Ser Lys Tyr Ser Ser Ser Thr Asn
            20                  25                  30

Val Ser Leu Arg Asp Arg Leu Arg His Phe Thr Trp Ala Trp Tyr Thr
        35                  40                  45

Leu Thr Met Ser Thr Gly Gly Leu Ala Leu Leu Ala Ser Gln Pro
    50                  55                  60

Tyr Thr Phe Ser Gly Leu Gln Gln Ile Gly Leu Ala Val Tyr Ile Ile
65                  70                  75                  80

Asn Leu Val Phe Phe Ala Leu Leu Cys Ser Leu Met Ala Thr Arg Phe
                85                  90                  95

Ile Leu His Gly Asn Phe Leu Asp Ser Leu Arg His Asp Arg Glu Gly
            100                 105                 110

Leu Phe Phe Pro Thr Phe Trp Leu Ser Ile Ala Thr Ile Ile Thr Gly
        115                 120                 125

Leu Tyr Arg Tyr Phe Gly Asp Thr Thr Gln Pro Ala Phe Ile Tyr Ala
    130                 135                 140

Leu Glu Val Leu Phe Trp Leu Tyr Cys Ala Phe Thr Leu Met Thr Ala
145                 150                 155                 160

Ile Ile Gln Tyr Ser Phe Val Phe Thr Ala His His Tyr Pro Leu Gln
                165                 170                 175
```

```
Thr Met Met Pro Ser Trp Ile Leu Pro Ala Phe Pro Ile Met Leu Ser
            180                 185                 190

Gly Thr Ile Ala Ser Val Ile Ala Glu Gln Gln Pro Ala Arg Ser Ala
        195                 200                 205

Ile Pro Met Ile Val Ala Gly Thr Thr Phe Gln Gly Leu Gly Phe Ser
    210                 215                 220

Ile Ser Phe Leu Met Tyr Ala His Tyr Ile Gly Arg Leu Met Glu Thr
225                 230                 235                 240

Gly Leu Pro Ser Arg Glu His Arg Pro Gly Met Phe Ile Cys Val Gly
                245                 250                 255

Pro Pro Ala Phe Thr Ala Leu Ala Leu Ile Gly Met Thr Asn Gly Leu
            260                 265                 270

Pro Glu Asp Phe Gln Val Leu Gln Asp Pro His Pro Phe Gln Asp Ala
        275                 280                 285

His Ile Leu Arg Leu Leu Ala Ile Ala Thr Gly Ala Phe Leu Trp Ala
    290                 295                 300

Leu Ser Leu Trp Phe Phe Ser Ile Ala Ile Ile Ala Thr Ile Arg Leu
305                 310                 315                 320

Pro Pro Thr Ala Phe His Leu Asn Trp Trp Ala Met Val Phe Pro Asn
                325                 330                 335

Thr Gly Phe Thr Leu Ala Thr Ile Thr Leu Gly Lys Ala Phe Asp Ser
            340                 345                 350

Pro Gly Val Lys Gly Val Gly Ser Ala Met Ser Ile Cys Ile Val Gly
        355                 360                 365

Met Trp Leu Phe Val Phe Ala Ser Asn Ile Arg Ala Val Val Lys Arg
    370                 375                 380

Asp Ile Val Phe Pro Gly Lys Asp Glu Asp Val Ser Glu
385                 390                 395
```

<210> SEQ ID NO 37
<211> LENGTH: 1353
<212> TYPE: DNA
<213> ORGANISM: Schizosaccharomyces japonicus

<400> SEQUENCE: 37

| | | | | | |
|---|---|---|---|---|---|
| atgtcgtcgg | agacaccgac | atactcctcc | tgggcatccc | agaggtacaa | cgaattgatt | 60 |
| gcatggaacg | tcaagggtcc | gaggttgccc | atcgcacaga | ggctcaagca | cttcacgtgg | 120 |
| tcgtggttca | cgtgtactat | ggcaacaggc | ggtgtcggaa | tgatcctcgc | gtcgctcccc | 180 |
| tataggttca | cgggcttgaa | caccatcgga | aaggtcgtct | tcattttcca | ggtggtcttg | 240 |
| ttggccatct | tctgttcggc | catggccttc | aggttcattc | gctacccgga | gactttcaag | 300 |
| aagtcgatct | atcaccactt | ggagaaattg | ttcatcggta | cattcttgct | ctcgatgtcg | 360 |
| accttcatcg | atatgctcgc | agcctacggc | tatccttcca | ccggtgaatg | gatggtgtac | 420 |
| ttgatccgaa | tcttctactg | gatgtacttc | gccgtctcct | tcgtctacgc | gatcttcgca | 480 |
| ttcgcaacta | ctttccatat | gcatccttat | accctcgaaa | cggcatcgcc | tgcctggatc | 540 |
| ctcccgattt | tccctgcgat | gatctccgga | gcagtggcag | gaaccgtggc | attcactcag | 600 |
| cctcccatc | agctcaaaaa | cctcgtggtg | tgtggcatta | tgttccaggg | tttgggcttc | 660 |
| tgggtctaca | tcatgttgtt | cgcggtcaac | atgctcaaat | tgttcacaaa | gggcatgatg | 720 |
| ggagcctcgg | aacgaccggg | tttgttcatg | ttcgtcggac | ctccggcata | cacaggcctc | 780 |
| gccctcatcg | gtatgggcaa | gaccgccatg | gattccaaaa | tctccatgtt | ctccgccact | 840 |

```
cccgtctcct ccgaacacct cgcattcatg tgtaccttca tggcactctt catgtgggt      900 ctcgcagcgt ggtgttattg tgtggcgatg gtctgtttcg cagcaggttt catgtccagg      960
gcacctatcc agttcaagtt gggatggttc gcgttcatct tccctgtcgt gggcttcgtg     1020
aacgtcacca tgaagatcgg cgagatgatt gactcggcag ccttcaaaat cttcggccac     1080
gtcatcggag ccatgttggc catccagtgg atgttcgtga tgttcttcat ggtgcgagcg     1140
gtcttgttgc aggaaatcat gtatcctgga cgggacgagg acgtcaaaac accgcctgga     1200
gccacacctc ctccgaccct cgtgacctcc cctctctcct tcgcatccct ccaggatgtc     1260
aaggatggac accccatcca ggtgacggtc tcccgcacta gggatcggtc gaaacagcac     1320
atgtcccagg gctcggacga ggaaaagatt taa                                  1353

<210> SEQ ID NO 38
<211> LENGTH: 1353
<212> TYPE: DNA
<213> ORGANISM: Schizosaccharomyces japonicus

<400> SEQUENCE: 38
atgtcttcgg aaacgccgac ttacagctct tgggcgagcc aacggtacaa cgaattgatc       60
gcttggaacg tcaagggtcc tcgcttaccc attgcccagc gtctaaaaca cttcacttgg      120
tcctggttta cctgtaccat ggccaccggt ggtgtcggta tgattctggc atcgctgccc      180
taccgattca caggcttaaa cacgattggt aaagtcgtgt tcattttcca ggtcgttttg      240
ctggcgattt tctgttcggc gatggccttt cggttcattc gttaccccga aaccttcaaa      300
aagtctattt accatcattt ggagaagctc ttcattggta ccttcctgct ttccatgtcg      360
acgttcatcg atatgctcgc cgcctacgga taccccagca ctggcgagtg gatggtgtac      420
ctaattcgca ttttttactg gatgtacttt gccgtctcgt tcgtatacgc catcttcgca      480
tttgctacca ccttttcacat gcatccctac accctggaga cggcttcccc agcatggatt      540
ctgcctattt tccagctat gattagcggc gctgtcgccg gtactgtggc cttcacacaa      600
ccgccgcacc aattgaagaa tttggtcgtg tgcggtatca tgttccaggg cttgggtttc      660
tgggtgtaca tcatgctgtt cgccgtgaac atgctcaagc tgtttacgaa gggtatgatg      720
ggtgcctctg aacgccctgg tcttttttatg ttcgttggtc ctccggccta taccggcttg      780
gctttaatcg gtatgggtaa aactgctatg gactccaaga tctccatgtt ttctgcaacc      840
cccgtttctt ctgaacacct tgcctttatg tgtacctta tggccttgtt tatgtggggt      900
cttgctgctt ggtgctattg tgtggccatg gtctgctttg ctgctggttt catgtctcgt      960
gctcctattc aattcaaact cggctggttc gcatttattt tcccagtcgt tggttttgtc     1020
aacgttacta tgaagattgg tgagatgatt gattcggccg cgttcaagat ctttggtcat     1080
gtcattggtg caatgcttgc cattcagtgg atgtttgtga tgttcttcat ggtccgcgcc     1140
gtcttactgc aagagatcat gtacccgggc cgcgacgaag atgtcaagac acctcccggt     1200
gccactcctc ctcccacttt ggtgacgagt ccccttgtcct ttgcttcgct gcaagacgta     1260
aaagatggcc atcccattca ggtcaccgtg tcccgcactc gagacagaag caaacagcac     1320
atgtcgcagg gctctgatga agaaaaaatc tag                                  1353

<210> SEQ ID NO 39
<211> LENGTH: 450
<212> TYPE: PRT
<213> ORGANISM: Schizosaccharomyces japonicus

<400> SEQUENCE: 39
```

```
Met Ser Ser Glu Thr Pro Thr Tyr Ser Ser Trp Ala Ser Gln Arg Tyr
1               5                   10                  15

Asn Glu Leu Ile Ala Trp Asn Val Lys Gly Pro Arg Leu Pro Ile Ala
            20                  25                  30

Gln Arg Leu Lys His Phe Thr Trp Ser Trp Phe Thr Cys Thr Met Ala
            35                  40                  45

Thr Gly Gly Val Gly Met Ile Leu Ala Ser Leu Pro Tyr Arg Phe Thr
        50                  55                  60

Gly Leu Asn Thr Ile Gly Lys Val Val Phe Ile Phe Gln Val Val Leu
65                  70                  75                  80

Leu Ala Ile Phe Cys Ser Ala Met Ala Phe Arg Phe Ile Arg Tyr Pro
                85                  90                  95

Glu Thr Phe Lys Lys Ser Ile Tyr His His Leu Glu Lys Leu Phe Ile
            100                 105                 110

Gly Thr Phe Leu Leu Ser Met Ser Thr Phe Ile Asp Met Leu Ala Ala
            115                 120                 125

Tyr Gly Tyr Pro Ser Thr Gly Glu Trp Met Val Tyr Leu Ile Arg Ile
        130                 135                 140

Phe Tyr Trp Met Tyr Phe Ala Val Ser Phe Val Tyr Ala Ile Phe Ala
145                 150                 155                 160

Phe Ala Thr Thr Phe His Met His Pro Tyr Thr Leu Glu Thr Ala Ser
                165                 170                 175

Pro Ala Trp Ile Leu Pro Ile Phe Pro Ala Met Ile Ser Gly Ala Val
            180                 185                 190

Ala Gly Thr Val Ala Phe Thr Gln Pro Pro His Gln Leu Lys Asn Leu
        195                 200                 205

Val Val Cys Gly Ile Met Phe Gln Gly Leu Gly Phe Trp Val Tyr Ile
        210                 215                 220

Met Leu Phe Ala Val Asn Met Leu Lys Leu Phe Thr Lys Gly Met Met
225                 230                 235                 240

Gly Ala Ser Glu Arg Pro Gly Leu Phe Met Phe Val Gly Pro Pro Ala
            245                 250                 255

Tyr Thr Gly Leu Ala Leu Ile Gly Met Gly Lys Thr Ala Met Asp Ser
            260                 265                 270

Lys Ile Ser Met Phe Ser Ala Thr Pro Val Ser Ser Glu His Leu Ala
            275                 280                 285

Phe Met Cys Thr Phe Met Ala Leu Phe Met Trp Gly Leu Ala Ala Trp
            290                 295                 300

Cys Tyr Cys Val Ala Met Val Cys Phe Ala Ala Gly Phe Met Ser Arg
305                 310                 315                 320

Ala Pro Ile Gln Phe Lys Leu Gly Trp Phe Ala Phe Ile Phe Pro Val
            325                 330                 335

Val Gly Phe Val Asn Val Thr Met Lys Ile Gly Glu Met Ile Asp Ser
            340                 345                 350

Ala Ala Phe Lys Ile Phe Gly His Val Ile Gly Ala Met Leu Ala Ile
            355                 360                 365

Gln Trp Met Phe Val Met Phe Phe Met Val Arg Ala Val Leu Leu Gln
        370                 375                 380

Glu Ile Met Tyr Pro Gly Arg Asp Glu Asp Val Lys Thr Pro Pro Gly
385                 390                 395                 400

Ala Thr Pro Pro Pro Thr Leu Val Thr Ser Pro Leu Ser Phe Ala Ser
            405                 410                 415
```

Leu Gln Asp Val Lys Asp Gly His Pro Ile Gln Val Thr Val Ser Arg
            420                 425                 430

Thr Arg Asp Arg Ser Lys Gln His Met Ser Gln Gly Ser Asp Glu Glu
        435                 440                 445

Lys Ile
    450

<210> SEQ ID NO 40
<211> LENGTH: 1179
<212> TYPE: DNA
<213> ORGANISM: Aspergillus clavatus

<400> SEQUENCE: 40

| | | | | | |
|---|---|---|---|---|---|
| atgttcgaaa | atcgtatacc | gccgacctcg | tctcagtcag | actctggctt | cctcgagaac | 60 |
| cagctggaaa | acaacatcg | actcagcctc | cgtgagaggt | taaggcactt | tacctgggcc | 120 |
| tggtacacat | tgaccatgag | cacaggtggg | ttggctctcc | tgatagcgag | ccagccatac | 180 |
| accttcaagg | ggttgaagac | cattggactg | gtggtctaca | tcgtgaactt | gatcttgttt | 240 |
| ggtcttgtct | gttcccttat | ggccactagg | ttcatcctcc | acggtggctt | cctcgactcc | 300 |
| cttcgccatg | agcgcgaggg | tcttttcttt | cctaccttct | ggctatccgt | agcaaccatc | 360 |
| atcaccggct | tgcatcgcta | cttcggctcc | gatgctcgag | aatcgtacct | gattgcactc | 420 |
| gaagtactct | tctgggtcta | ctgtgcctgt | acactggcca | cagcagtgat | ccagtactcc | 480 |
| ttcatcttct | ctgcgcacag | atacggcctc | cagaccatga | tgccctcctg | gattctccca | 540 |
| gccttcccca | tcatgctcag | tggcacgatt | gcctccgtca | tcggcgaagc | tcaacccgca | 600 |
| cggtcatcga | tccccgtcat | catggccgga | gtcaccttcc | agggcctggg | gttctcgatc | 660 |
| agcttcatga | tgtacgccca | ctatatcggc | cggctgatgg | aatcagggct | cccctgccgc | 720 |
| gagcacagac | ccggcatgtt | catctgcgtt | ggtccccgg | ctttcacagc | cctcgctcta | 780 |
| gtcgggatgg | ccaagggcct | gcccgccgag | ttcaagctca | tcaacgacgc | acacgccctc | 840 |
| gaagacgcgc | ggatcctcga | gctgctcgca | atcaccgcgg | gcatcttcct | ctgggccctg | 900 |
| agtctgtggt | tcttcttcat | cgccgtcatc | gccgtcctcc | ggtccccgcc | tacttccttc | 960 |
| catctcaact | ggtgggcctt | ggtcttcccg | aacacgggct | tcactttggc | caccatcacg | 1020 |
| cttggaaagg | cattgggcag | tcccgggatc | ttgggcgttg | ttctgccat | gtcccttggc | 1080 |
| atcgttggca | tgtggctgtt | tgtttttgtc | agccatatcc | gtgccatcat | caaccaggat | 1140 |
| atcatgtatc | cgggcaaaga | tgaggatgct | gcagactag | | | 1179 |

<210> SEQ ID NO 41
<211> LENGTH: 392
<212> TYPE: PRT
<213> ORGANISM: Aspergillus clavatus

<400> SEQUENCE: 41

Met Phe Glu Asn Arg Ile Pro Pro Thr Ser Ser Gln Ser Asp Ser Gly
1               5                   10                  15

Phe Leu Glu Asn Gln Leu Glu Lys Gln His Arg Leu Ser Leu Arg Glu
            20                  25                  30

Arg Leu Arg His Phe Thr Trp Ala Trp Tyr Thr Leu Thr Met Ser Thr
        35                  40                  45

Gly Gly Leu Ala Leu Leu Ile Ala Ser Gln Pro Tyr Thr Phe Lys Gly
    50                  55                  60

Leu Lys Thr Ile Gly Leu Val Val Tyr Ile Val Asn Leu Ile Leu Phe
65                  70                  75                  80

```
Gly Leu Val Cys Ser Leu Met Ala Thr Arg Phe Ile Leu His Gly Gly
                85                  90                  95
Phe Leu Asp Ser Leu Arg His Glu Arg Glu Gly Leu Phe Phe Pro Thr
            100                 105                 110
Phe Trp Leu Ser Val Ala Thr Ile Ile Thr Gly Leu His Arg Tyr Phe
        115                 120                 125
Gly Ser Asp Ala Arg Glu Ser Tyr Leu Ile Ala Leu Glu Val Leu Phe
    130                 135                 140
Trp Val Tyr Cys Ala Cys Thr Leu Ala Thr Ala Val Ile Gln Tyr Ser
145                 150                 155                 160
Phe Ile Phe Ser Ala His Arg Tyr Gly Leu Gln Thr Met Met Pro Ser
                165                 170                 175
Trp Ile Leu Pro Ala Phe Pro Ile Met Leu Ser Gly Thr Ile Ala Ser
            180                 185                 190
Val Ile Gly Glu Ala Gln Pro Ala Arg Ser Ser Ile Pro Val Ile Met
        195                 200                 205
Ala Gly Val Thr Phe Gln Gly Leu Gly Phe Ser Ile Ser Phe Met Met
    210                 215                 220
Tyr Ala His Tyr Ile Gly Arg Leu Met Glu Ser Gly Leu Pro Cys Arg
225                 230                 235                 240
Glu His Arg Pro Gly Met Phe Ile Cys Val Gly Pro Pro Ala Phe Thr
                245                 250                 255
Ala Leu Ala Leu Val Gly Met Ala Lys Gly Leu Pro Ala Glu Phe Lys
            260                 265                 270
Leu Ile Asn Asp Ala His Ala Leu Glu Asp Ala Arg Ile Leu Glu Leu
        275                 280                 285
Leu Ala Ile Thr Ala Gly Ile Phe Leu Trp Ala Leu Ser Leu Trp Phe
    290                 295                 300
Phe Phe Ile Ala Val Ile Ala Val Leu Arg Ser Pro Pro Thr Ser Phe
305                 310                 315                 320
His Leu Asn Trp Trp Ala Leu Val Phe Pro Asn Thr Gly Phe Thr Leu
                325                 330                 335
Ala Thr Ile Thr Leu Gly Lys Ala Leu Gly Ser Pro Gly Ile Leu Gly
            340                 345                 350
Val Gly Ser Ala Met Ser Leu Gly Ile Val Gly Met Trp Leu Phe Val
        355                 360                 365
Phe Val Ser His Ile Arg Ala Ile Ile Asn Gln Asp Ile Met Tyr Pro
    370                 375                 380
Gly Lys Asp Glu Asp Ala Ala Asp
385                 390

<210> SEQ ID NO 42
<211> LENGTH: 1182
<212> TYPE: DNA
<213> ORGANISM: Aspergillus fumigatus

<400> SEQUENCE: 42
atgttcaacg atcatgatca tgttccacca acatcatcac agtcggattc tggctttttt      60
gaacaagaaa tgaagaaatc tcctcgacta agccttcgtg agcgcctacg gcacttcacc     120
tgggcgtggt ataccttgac gatgagtacc ggtggactgg ctcttctgat tgctagtcag     180 ccgtataccctcaatggcat gaagggcatc gggatggtcg tttatatcct caatcttctg     240
ttattcgctc ttgtctgttc tttgatggtg ctgagattcg ttttgcatgg cggtttcctt     300
```

```
gacagcttgc gccaccctcg cgagggtctc ttcttcccta ccttctggct atccattgca    360
acgatcatca ctggcttgca tcgttacttc ggctccgacg acctagagtc gtacctcatc    420
gcactcgaag tcctcttctg ggtctactgt agttgcaccc tcgccacagc tgtgatccag    480
tactcattcc tctttgccgc ccactcctac ggcctgcaga caatgatgcc atcatggatc    540
ctaccagcct tccccatcat gctcagcgga accatcgcct cggtcatcag cgaatcccag    600
cccgcgcgat ccgcgatccc catcatcact gccggcgtta ccttccaggg cctcggcttc    660
tcaatcagct tcataatgta cgcccactac atcggccgac tcatgcagtc agggcttccc    720
tgccgcgaac acagaccagc catgttcatt gcgtggggc ctccgtcttt caccgcgttg    780
gcgctagtag ggatggccaa gggcctgccc gacgaattca agataatcaa agacgcacac    840
gtcgaggacg cccggatcct cgagctgatg gctattatcg tcggcgtgtt cctgtgggcc    900
ctgagtctct ggttcttctt cattgccttt gttgctgtcg tccggtgccg gcccactgcg    960
ttccaccctta gctggtgggc catggtcttc cccaacactg ggttcacgct ggccactatt   1020
accctgggga gggcattggg gagccctggc gtcttgggcg tcggctcggc catgtcggtc   1080
ggtgttgtct gcatgtgggt cttcgttttc gtctaccaca ttcgtgctgt catcaggcaa   1140
gacatcatgt acccgggcaa agacgaggat gtgctagatt aa                      1182
```

<210> SEQ ID NO 43
<211> LENGTH: 393
<212> TYPE: PRT
<213> ORGANISM: Aspergillus fumigatus

<400> SEQUENCE: 43

```
Met Phe Asn Asp His Asp His Val Pro Pro Thr Ser Ser Gln Ser Asp
1               5                   10                  15

Ser Gly Phe Phe Glu Gln Glu Met Lys Lys Ser Pro Arg Leu Ser Leu
            20                  25                  30

Arg Glu Arg Leu Arg His Phe Thr Trp Ala Trp Tyr Thr Leu Thr Met
        35                  40                  45

Ser Thr Gly Gly Leu Ala Leu Leu Ile Ala Ser Gln Pro Tyr Thr Phe
    50                  55                  60

Asn Gly Met Lys Gly Ile Gly Met Val Val Tyr Ile Leu Asn Leu Leu
65                  70                  75                  80

Leu Phe Ala Leu Val Cys Ser Leu Met Val Leu Arg Phe Val Leu His
                85                  90                  95

Gly Gly Phe Leu Asp Ser Leu Arg His Pro Arg Glu Gly Leu Phe Phe
            100                 105                 110

Pro Thr Phe Trp Leu Ser Ile Ala Thr Ile Ile Thr Gly Leu His Arg
        115                 120                 125

Tyr Phe Gly Ser Asp Asp Leu Glu Ser Tyr Leu Ile Ala Leu Glu Val
    130                 135                 140

Leu Phe Trp Val Tyr Cys Ser Cys Thr Leu Ala Thr Ala Val Ile Gln
145                 150                 155                 160

Tyr Ser Phe Leu Phe Ala Ala His Ser Tyr Gly Leu Gln Thr Met Met
                165                 170                 175

Pro Ser Trp Ile Leu Pro Ala Phe Pro Ile Met Leu Ser Gly Thr Ile
            180                 185                 190

Ala Ser Val Ile Ser Glu Ser Gln Pro Ala Arg Ser Ala Ile Pro Ile
        195                 200                 205

Ile Thr Ala Gly Val Thr Phe Gln Gly Leu Gly Phe Ser Ile Ser Phe
    210                 215                 220
```

Ile Met Tyr Ala His Tyr Ile Gly Arg Leu Met Gln Ser Gly Leu Pro
225                 230                 235                 240

Cys Arg Glu His Arg Pro Ala Met Phe Ile Cys Val Gly Pro Pro Ser
            245                 250                 255

Phe Thr Ala Leu Ala Leu Val Gly Met Ala Lys Gly Leu Pro Asp Glu
        260                 265                 270

Phe Lys Ile Ile Lys Asp Ala His Val Glu Asp Ala Arg Ile Leu Glu
    275                 280                 285

Leu Met Ala Ile Ile Val Gly Val Phe Leu Trp Ala Leu Ser Leu Trp
290                 295                 300

Phe Phe Phe Ile Ala Phe Val Ala Val Arg Cys Arg Pro Thr Ala
305                 310                 315                 320

Phe His Leu Ser Trp Trp Ala Met Val Phe Pro Asn Thr Gly Phe Thr
            325                 330                 335

Leu Ala Thr Ile Thr Leu Gly Arg Ala Leu Gly Ser Pro Gly Val Leu
        340                 345                 350

Gly Val Gly Ser Ala Met Ser Val Gly Val Val Cys Met Trp Val Phe
    355                 360                 365

Val Phe Val Tyr His Ile Arg Ala Val Ile Arg Gln Asp Ile Met Tyr
370                 375                 380

Pro Gly Lys Asp Glu Asp Val Leu Asp
385                 390

<210> SEQ ID NO 44
<211> LENGTH: 1294
<212> TYPE: DNA
<213> ORGANISM: Aspergillus oryzae

<400> SEQUENCE: 44
atgttcgctg ctcgccagtc tttcaacctc ctccagaagc gcgccttctc cgcctctgcc      60
agccaggtgt gtgattgaat ggatccattg gacctcggag ctagctctgc aacatcaaca     120
aaactaacat actaacttat cttcttcata ggcttccaag gttgccgttc ttggtgccgc     180
tggtggcatt ggccagcctc tctcccttct cctcaagctc aaccccgtg tttctgagct      240 tgccctctac gatatccgcg gtggccctgg tatgttttg cacagcttgc aacatctccg      300
acttcggtga ttcaagacag gctaacata aggatacaat aggtgttgcc gctgacctga     360
gccacatcaa caccaacagc accgtctctg ctacgaggc tacccctct ggcctccgtg      420 atgctctcaa gggctccgag atcgtcctca tccctgccgg tgttcctcgc aagcccggca     480
tgacccgtga cggtatgaac cgttaacttg tcaatggcac tgggaattga atactaatta     540
taatatcgcc agacctgttc aacaccaacg cctccattgt ccgcgacctt gctaaggccg     600
ccgccgaggc ttcccccgag ccaacatcc tcgtcatctc caaccctgta tgacgctttc     660
cacccactgc taccagttat ctcgcgctaa ttgcaatcag gtcaactcca ccgtccccat     720
cgtctctgag gtcttcaagt ccaagggtgt ctacaacccc aagcgtctct tcggtgtcac     780 taccccttgac gttgtccgtg cctctcgctt catctcccag gtccagaaga ccgacccctc     840
caacgaggcc gtcactgtcg tcggtggtca ctccggtgtg accattgtcc ctcttctctc     900
ccagtccagc caccccagca ttgagggtaa gacccgcgat gagctcgtca accgcatcca     960
gttcggtggt gatgaggttg tcaaggccaa ggatggtgct ggctctgcca ccctctccat    1020
ggccatggct ggtgctcgca tggctgagtc cctcctgaag ccgcccagg gtgagaaggg    1080 tgtcgttgag cccactttcg tcgacagccc tctctacaag gaccagggtg ttgacttctt    1140

```
cgcctccaag gtcgagctcg gccccaacgg tgttgagaag atcctcccccg ttggccaggt    1200 caacgcctac gaggagaagc tcctcgaggc ctgccttggt gacctcaaga gaacatcca      1260 gaagggtatt gacttcgtca aggccaaccc ttaa                                  1294
```

<210> SEQ ID NO 45
<211> LENGTH: 340
<212> TYPE: PRT
<213> ORGANISM: Aspergillus oryzae

<400> SEQUENCE: 45

```
Met Phe Ala Ala Arg Gln Ser Phe Asn Leu Leu Gln Lys Arg Ala Phe
1               5                   10                  15

Ser Ala Ser Ala Ser Gln Ala Ser Lys Val Ala Val Leu Gly Ala Ala
            20                  25                  30

Gly Gly Ile Gly Gln Pro Leu Ser Leu Leu Lys Leu Asn Pro Arg
        35                  40                  45

Val Ser Glu Leu Ala Leu Tyr Asp Ile Arg Gly Pro Gly Val Ala
    50                  55                  60

Ala Asp Leu Ser His Ile Asn Thr Asn Ser Thr Val Ser Gly Tyr Glu
65                  70                  75                  80

Ala Thr Pro Ser Gly Leu Arg Asp Ala Leu Lys Gly Ser Glu Ile Val
                85                  90                  95

Leu Ile Pro Ala Gly Val Pro Arg Lys Pro Gly Met Thr Arg Asp Asp
            100                 105                 110

Leu Phe Asn Thr Asn Ala Ser Ile Val Arg Asp Leu Ala Lys Ala Ala
        115                 120                 125

Ala Glu Ala Ser Pro Glu Ala Asn Ile Leu Val Ile Ser Asn Pro Val
    130                 135                 140

Asn Ser Thr Val Pro Ile Val Ser Glu Val Phe Lys Ser Lys Gly Val
145                 150                 155                 160

Tyr Asn Pro Lys Arg Leu Phe Gly Val Thr Thr Leu Asp Val Val Arg
                165                 170                 175

Ala Ser Arg Phe Ile Ser Gln Val Gln Lys Thr Asp Pro Ser Asn Glu
            180                 185                 190

Ala Val Thr Val Val Gly Gly His Ser Gly Val Thr Ile Val Pro Leu
        195                 200                 205

Leu Ser Gln Ser Ser His Pro Ser Ile Glu Gly Lys Thr Arg Asp Glu
    210                 215                 220

Leu Val Asn Arg Ile Gln Phe Gly Gly Asp Glu Val Val Lys Ala Lys
225                 230                 235                 240

Asp Gly Ala Gly Ser Ala Thr Leu Ser Met Ala Met Ala Gly Ala Arg
                245                 250                 255

Met Ala Glu Ser Leu Leu Lys Ala Ala Gln Gly Glu Lys Gly Val Val
            260                 265                 270

Glu Pro Thr Phe Val Asp Ser Pro Leu Tyr Lys Asp Gln Gly Val Asp
        275                 280                 285

Phe Phe Ala Ser Lys Val Glu Leu Gly Pro Asn Gly Val Glu Lys Ile
    290                 295                 300

Leu Pro Val Gly Gln Val Asn Ala Tyr Glu Lys Leu Leu Glu Ala
305                 310                 315                 320

Cys Leu Gly Asp Leu Lys Lys Asn Ile Gln Lys Gly Ile Asp Phe Val
                325                 330                 335

Lys Ala Asn Pro
```

```
<210> SEQ ID NO 46
<211> LENGTH: 20
<212> TYPE: DNA
<213> ORGANISM: Aspergillus oryzae

<400> SEQUENCE: 46
tgaccttcca cgctgaccac                                               20

<210> SEQ ID NO 47
<211> LENGTH: 20
<212> TYPE: DNA
<213> ORGANISM: Aspergillus oryzae

<400> SEQUENCE: 47
ggctgagaaa atatgttgca                                               20

<210> SEQ ID NO 48
<211> LENGTH: 30
<212> TYPE: DNA
<213> ORGANISM: Aspergillus oryzae

<400> SEQUENCE: 48
gatagaccac taatcatggt ggcgatggag                                    30

<210> SEQ ID NO 49
<211> LENGTH: 30
<212> TYPE: DNA
<213> ORGANISM: Aspergillus oryzae

<400> SEQUENCE: 49
tgcggtcctg agtcaggccc agttgctcga                                    30

<210> SEQ ID NO 50
<211> LENGTH: 20
<212> TYPE: DNA
<213> ORGANISM: Aspergillus oryzae

<400> SEQUENCE: 50
gggatttgaa cagcagaagg                                               20

<210> SEQ ID NO 51
<211> LENGTH: 20
<212> TYPE: DNA
<213> ORGANISM: Aspergillus oryzae

<400> SEQUENCE: 51
tcacaaaaga gtagaggcca                                               20

<210> SEQ ID NO 52
<211> LENGTH: 41
<212> TYPE: DNA
<213> ORGANISM: Artificial Sequence
<220> FEATURE:
<223> OTHER INFORMATION: ARTIFICIAL DNA PRIMER

<400> SEQUENCE: 52
gtgatagaac atcgtccata atgccgggcg atctcaaaac c                       41

<210> SEQ ID NO 53
<211> LENGTH: 39
<212> TYPE: DNA
<213> ORGANISM: Artificial Sequence
```

```
<220> FEATURE:
<223> OTHER INFORMATION: ARTIFICIAL DNA PRIMER

<400> SEQUENCE: 53
gtgtcagtca cctctagtta ctatgcatca aggacattc                              39

<210> SEQ ID NO 54
<211> LENGTH: 20
<212> TYPE: DNA
<213> ORGANISM: Artificial Sequence
<220> FEATURE:
<223> OTHER INFORMATION: ARTIFICIAL DNA PRIMER

<400> SEQUENCE: 54
gattgagatc ggcatttact                                                   20

<210> SEQ ID NO 55
<211> LENGTH: 20
<212> TYPE: DNA
<213> ORGANISM: Artificial Sequence
<220> FEATURE:
<223> OTHER INFORMATION: ARTIFICIAL DNA PRIMER

<400> SEQUENCE: 55
acgcggaaca gcagaatggc                                                   20

<210> SEQ ID NO 56
<211> LENGTH: 25
<212> TYPE: DNA
<213> ORGANISM: Artificial Sequence
<220> FEATURE:
<223> OTHER INFORMATION: ARTIFICIAL DNA PRIMER

<400> SEQUENCE: 56
ctatagcgaa atggattgat tgtct                                             25

<210> SEQ ID NO 57
<211> LENGTH: 20
<212> TYPE: DNA
<213> ORGANISM: Artificial Sequence
<220> FEATURE:
<223> OTHER INFORMATION: ARTIFICIAL DNA PRIMER

<400> SEQUENCE: 57
ttcaccgtga aacgtattga                                                   20
```

MICROORGANISMS FOR C4-DICARBOXYLIC ACID PRODUCTION

CROSS REFERENCE TO RELATED APPLICATIONS

This application is a divisional of U.S. patent application Ser. No. 13/407,584, filed Feb. 28, 2012, now U.S. Pat. No. 8,722,387, which claims priority benefit of U.S. Provisional Application No. 61/447,286, filed Feb. 28, 2011. The content of these applications are fully incorporated herein by reference.

REFERENCE TO A SEQUENCE LISTING

This application contains a Sequence Listing in computer readable form, which is incorporated herein by reference.

BACKGROUND OF THE INVENTION

1. Field of the Invention

The present invention relates to methods for the recombinant production of C4-dicarboxylic acids (e.g., malic acid).

2. Description of the Related Art

Organic acids have a long history of commercial use in a variety of industries. For example, organic acids are used in the food and feed industries (citric acid, ascorbic acid, lactic acid, acetic acid, and gluconic acid) as monomers for the production of various polymers (adipic acid, lactic acid, acrylic acid, and itaconic acid), as metal chelators (gluconic acid), and as "green" solvents (acetic acid) (Sauer et al., 2008, *Trends in Biotechnology* 26: 100-108). Organic acids may themselves be commercial products or they may be chemical building blocks used in the manufacture of other chemicals. In addition to specialty applications, it has long been recognized that C4-dicarboxylic acids can also serve as building block compounds for the production of large volume industrial chemicals, such as 1,4-butanediol, tetrahydrofuran, and gamma-butyrolactone. The cost of producing these large volume industrial chemicals by traditional petrochemical routes has increased significantly due to the high cost of petroleum derived building blocks.

Organic acids may be produced commercially either by chemical synthesis from petroleum derived feedstocks (e.g., fumaric acid, malic acid, acrylic acid, and adipic acid) or by microbial fermentation (e.g., citric acid, lactic acid, gluconic acid, and itaconic acid). Some organic acids—such as fumaric acid and malic acid—can also be produced by microbial fermentation, but are currently produced commercially by chemical synthesis from petrochemical feedstocks due to lower production costs. However, the rising cost of petroleum derived building block chemicals, the geopolitical instability affecting crude oil prices, and the desire to implement manufacturing processes that utilize feedstocks derived from renewable resources have stimulated a renewed interest in producing organic acids and other chemicals by microbial fermentation.

While C4-dicarboxylic acids such as malic acid are produced commercially today by chemical synthesis from petrochemical sources, it can also be produced by microbial fermentation. Malic acid has been produced at high levels in genetically engineered yeast (*Saccharomyces cerevisiae*) (Zelle et al., 2008, *Appl. Environ. Microbiol.* 74: 2766-2777) and naturally occurring filamentous fungi such as *Aspergillus* spp. (U.S. Pat. No. 3,063,910; Bercovitz et al., 1990, *Appl. Environ. Microbiol.* 56: 1594-1597). Abe et al. (U.S. Pat. No. 3,063,910) and Bercovitz et al. (1990, *Appl. Environ. Microbiol.* 56: 1594-1597) reported high levels of malic acid production in several species of *Aspergillus*. Moreover, Battat et al. (1991, *Biotechnol. Bioengineering,* 37: 1108-1116) reported malic acid production as high as 113 g/L by *Aspergillus flavus* in a stirred fermentor under optimized conditions. Dicarboxylic acid production by microbial fermentation in yeast is described in WO 2010/003728. Malic acid production by microbial fermentation is also described in WO 2009/011974, WO 2009/155382 and WO2010/111344. Improvement of the production of C4-dicarboxylic acids such as malic acid by genetic engineering may enable economical commercial malic acid production by fermentation.

Malic acid overproduction in a host such as *Aspergillus* spp. occurs under specific culture conditions (aerobic conditions and high C:N ratio; calcium carbonate may also added as a neutralizing agent and as source of $CO_2$ for malic acid biosynthesis). Under these conditions, overflow metabolism via the cytosolic, reductive tricarboxylic acid (TCA) cycle results in increased malic acid biosynthesis and secretion into the culture medium. Increased malic acid production has been reported in *Saccharomyces cerevisiae* by increasing the level of pyruvate carboxylase (Bauer et al., 1999, *FEMS Microbiol Lett.* 179: 107-113) or malate dehydrogenase (Pines et al., 1997, *Appl. Microbiol. Biotechnol.* 48: 248-255) using genetic engineering and increasing expression of a malic acid transporter (Zelle et al., 2008, supra). It has been suggested, based on biochemical evidence, that malate dehydrogenase activity is limiting malic acid production in *Aspergillus flavus* strain ATCC 13697 (Peleg et al., 1988, *Appl. Microbiol. Biotechnol.* 28: 69-75). U.S. application Ser. No. 12/870,523, entitled "Methods for Improving Malic Acid Production in Filamentous Fungi" filed Aug. 27, 2010, and U.S. Provisional application No. 61/356,868, entitled "Polypeptides Having C4-dicarboxylic acid Transporter Activity and Polynucleotides Encoding Same" filed Jun. 21, 2010—the contents of which are hereby incorporated by reference in their entireties—describe C4-dicarboxylic acid production.

It would be advantageous in the art to improve C4-dicarboxylic acid production, such as malic acid production, as a result of genetic engineering using recombinant DNA techniques. The present invention provides, inter alia, methods for improving C4-dicarboxylic acid production (e.g., malic acid production).

SUMMARY OF THE INVENTION

The present invention relates to recombinant host cells comprising bicarbonate transporter activity, wherein the host cell produces (or is capable of producing) an increased amount of a C4-dicarboxylic acid (e.g., malic acid). In one aspect, the recombinant host cells comprise a heterologous polynucleotide encoding a bicarbonate transporter (e.g., a sulfate-bicarbonate transporter), wherein the host cell produces (or is capable of producing) and/or secretes (or is capable of secreting) a greater amount of a C4-dicarboxylic acid (e.g., malic acid) compared to the host cell without the heterologous polynucleotide when cultivated under the same conditions. In some aspects, the host cell further comprises a heterologous polynucleotide encoding a C4-dicarboxylic acid transporter, a heterologous polynucleotide encoding a malate dehydrogenase, and/or a heterologous polynucleotide encoding a pyruvate carboxylase. In some aspects, the host cell is a filamentous fungal host cell, such as an *Aspergillus oryzae* host cell.

The present invention also relates to methods of using recombinant host cells for the production of a C4-dicarboxylic acid. In one aspect, the invention related to methods of producing a C4-dicarboxylic acid (e.g., malic acid), comprising: (a) cultivating a recombinant host cell (e.g., a filamentous fungal host cell) having bicarbonate transporter activity in a medium under suitable conditions to produce the C4-dicarboxylic acid; and (b) recovering the C4-dicarboxylic acid. In some aspects, the recombinant host cell comprises a heterologous polynucleotide encoding a bicarbonate transporter (e.g., a sulfate-bicarbonate transporter). In another aspect, the invention related to methods of producing a C4-dicarboxylic acid (e.g., malic acid) comprising (a) transforming into a host cell (e.g., a filamentous fungal host cell) a heterologous polynucleotide encoding a bicarbonate transporter described herein; (b) cultivating the transformed organism in a medium under suitable conditions to produce the C4-dicarboxylic acid; and (c) recovering the C4-dicarboxylic acid. In some aspects of the methods, the recombinant host cell further comprises a heterologous polynucleotide encoding a C4-dicarboxylic acid transporter, a heterologous polynucleotide encoding a malate dehydrogenase, and/or a heterologous polynucleotide encoding a pyruvate carboxylase.

BRIEF DESCRIPTION OF THE FIGURES

FIGS. 3A and 3B show the genomic nucleotide construct sequence and the deduced amino acid sequence of an *Aspergillus oryzae* NRRL 3488 bicarbonate transporter gene (bt1) (SEQ ID NOs: 1 and 2, respectively).
FIGS. 4A and 4B show the genomic nucleotide construct sequence and the deduced amino acid sequence of an *Aspergillus oryzae* NRRL 3488 bicarbonate transporter gene (bt2) (SEQ ID NOs: 3 and 4, respectively).
FIG. 6 shows the genomic DNA sequence and the deduced amino acid sequence of an *Aspergillus aculeatus* C4-dicarboxylic acid transporter gene (c4t521) (SEQ ID NOs: 5 and 6, respectively).
FIG. 7 shows the genomic DNA sequence and the deduced amino acid sequence of an *Aspergillus oryzae* NRRL 3488 malate dehydrogenase gene (mdh3) (SEQ ID NOs: 7 and 8, respectively).
FIGS. 9A and 9B together show the genomic DNA sequence and the deduced amino acid sequence of an *Aspergillus oryzae* NRRL 3488 pyruvate carboxylase gene (pyc) (SEQ ID NOs: 9 and 10, respectively).

DEFINITIONS

Figure 1:
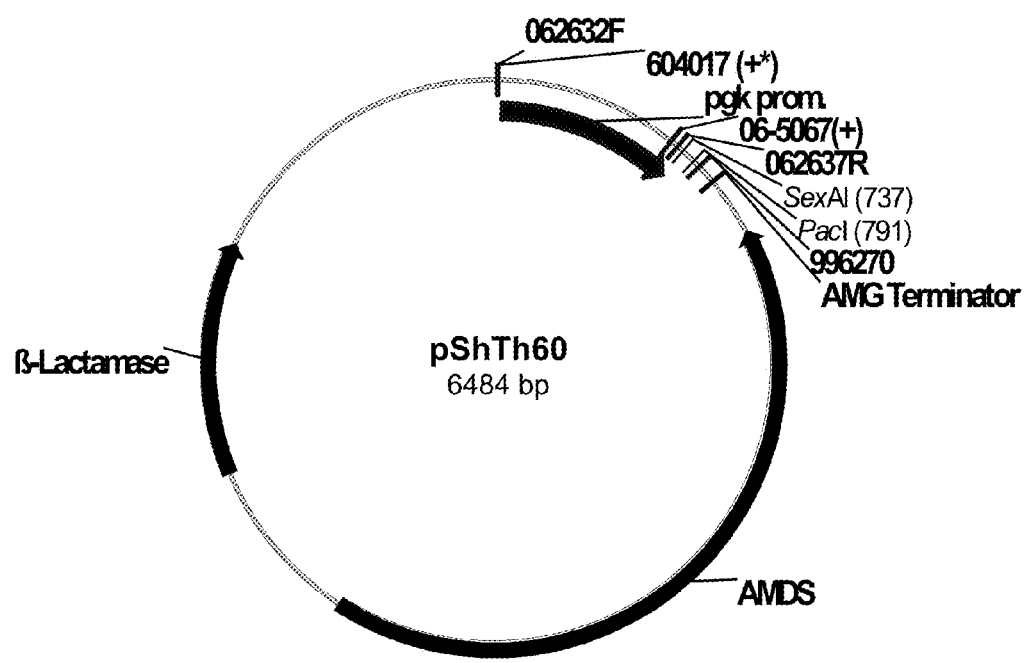
FIG. 1 shows a restriction map of pShTh60.

Bicarbonate transporter: The term "bicarbonate transporter" is defined herein as a protein—such as a membrane integrated protein—capable of facilitating the transfer of $HCO_3^-$ across a biological membrane, such as a cell membrane and/or the membrane of a cell organelle. Non-limiting classes of biocarbonate transporter proteins include the anion exchanger (AE) family of $Cl^-/HCO_3^-$ exchangers, the NBC family of $Na^+/HCO_3^-$ cotransporters, and the $Na^+$-dependent $Cl^-/HCO_3^-$ exchangers. In some aspects described herein, the bicarbonate transporter is a sulfate-bicarbonate transporter, wherein the transporter is capable of facilitating the transfer of both $HCO_3^-$ and $SO_4^{2-}$ anions across a biological membrane. Biocarbonate exchange activity can be determined as described in the art, e.g., as described in Sterling et al., 2002, *Am J Physiol Cell Physiol* 283: C1522-1529.

The bicarbonate transporters have at least 20%, e.g., at least 40%, at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, or at least 100% of the bicarbonate transporter activity of the mature polypeptide sequence of SEQ ID NO: 2 or 4.

C4-dicarboxylic acid transporter: The term "C4-dicarboxylic acid transporter" is defined herein as a dicarboxylic acid permease that can transport malic acid, succinic acid, oxaloacetic acid, malonic acid, and/or fumaric acid outside a cell (Grobler et al., 1995, *Yeast* 11: 1485-1491; Camarasa et al., 2001, *Applied and Environmental Microbiology* 67: 4144-4151). A computational method to predict mitochondrially imported proteins and their targeting sequences is described by Claros and Vincens, 1996, *Eur. J. Biochem.* 241: 779-786.

The C4-dicarboxylic acid transporters have at least 20%, e.g., at least 40%, at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, or at least 100% of the C4-dicarboxylic acid transporter activity (e.g., malic acid transporter activity) of the mature polypeptide sequence of SEQ ID NO: 6.

Malate dehydrogenase: The term "malate dehydrogenase" is defined herein as a malate:$NAD^+$ oxidoreductase (EC 1.1.1.37) that catalyzes the reduction of oxaloacetate in the presence of $NADH+H^+$ to malate and $NAD^+$. For purposes of the present invention, malate dehydrogenase activity is determined according to the following procedure. The assay solution consists of 1 mM oxaloacetic acid, 100 mM Tris pH 8.0, 10 mM $NaHCO_3$, 5 mM $MgCl_2$, and 0.1 mM NADH (Sigma Chemical Co., St. Louis, Mo., USA). The assay solution without oxaloacetic acid as substrate is run as a control to measure background NADH degradation rates. Dilutions of 1/100, 1/500, 1/2500, and 1/12500 of each supernatant are prepared with double-distilled water. Aliquots of 270 µl of the assay solution are dispensed into 96 well polystyrene flat bottom plates. A 30 µl sample of each diluted supernatant is added to initiate the assay. The reactions are monitored using a SPECTRAMAX® 340PC plate reader (Molecular Devices, Sunnyvale, Calif., USA) with the following settings: 340 nm, kinetic reading. A concentration series of NADH is used to construct a standard curve and a dilution series of purified malic dehydrogenase (Sigma Chemical Co., St. Louis, Mo., USA) is used as a positive control. One unit of malate dehydrogenase activity equals the amount of enzyme capable of converting 1 µmole of oxaloacetate and $NADH+H^+$ to malate and $NAD^+$ per minute at pH 8.0, 25° C.

The malate dehydrogenases have at least 20%, e.g., at least 40%, at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, or at least 100% of the malate dehydrogenase activity of the mature polypeptide sequence of SEQ ID NO: 8.

Pyruvate carboxylase: The term "pyruvate carboxylase" is defined herein as a pyruvate:carbon-dioxide ligase (ADP-forming) (EC 6.4.1.1) that catalyzes the carboxylation of pyruvate in the presence of ATP and $HCO_3^-$ to oxaloacetate, ADP, and phosphate. For purposes of the present invention, pyruvate carboxylase activity is determined according to the procedure of the SIGMA® Quality Control Test procedure for pyruvate carboxylase (Sigma Chemical Co., St. Louis, Mo., USA) except the assay uses Tris buffer at pH 8.0. One unit of pyruvate carboxylase activity equals the amount of enzyme capable of converting 1 µmole of pyruvate and $CO_2$ to oxaloacetate per minute at pH 7.8, 30° C.

The pyruvate carboxylases have at least 20%, e.g., at least 40%, at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, or at least 100% of the pyruvate carboxylase activity of the mature polypeptide sequence of SEQ ID NO: 10.

Heterologous polynucleotide: The term "heterologous polynucleotide" is defined herein as a polynucleotide that is not native to the host cell; a native polynucleotide in which structural modifications have been made to the coding region; a native polynucleotide whose expression is quantitatively altered as a result of a manipulation of the DNA by recombinant DNA techniques, e.g., a different (foreign) promoter; or a native polynucleotide whose expression is quantitatively altered by the introduction of one or more (several) extra copies of the polynucleotide into the host cell.

Isolated/purified: The terms "isolated" and "purified" mean a polypeptide or polynucleotide that is removed from at least one component with which it is naturally associated. For example, a polypeptide may be at least 1% pure, e.g., at least 5% pure, at least 10% pure, at least 20% pure, at least 40% pure, at least 60% pure, at least 80% pure, at least 90% pure, at least 93% pure, at least 95% pure, at least 97%, at least 98% pure, or at least 99% pure, as determined by SDS-PAGE and a polynucleotide may be at least 1% pure, e.g., at least 5% pure, at least 10% pure, at least 20% pure, at least 40% pure, at least 60% pure, at least 80% pure, at least 90%, at least 93% pure, at least 95% pure, at least 97%, at least 98% pure, or at least 99% pure, as determined by agarose electrophoresis.

Coding sequence: The term "coding sequence" means a polynucleotide sequence, which specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be a sequence of genomic DNA, cDNA, a synthetic polynucleotide, and/or a recombinant polynucleotide.

cDNA sequence: The term "cDNA sequence" means a sequence of DNA following reverse transcription from a mature, spliced, mRNA molecule obtained from a eukaryotic cell. The initial, primary RNA transcript from genomic DNA is a precursor to mRNA that is processed through a series of steps, including splicing, before appearing as mature spliced mRNA. A cDNA sequence lacks intervening intron sequences that may be present in the corresponding genomic DNA sequence. Accordingly, the phrase "the cDNA sequence of SEQ ID NO: X" intends the resulting sequence after the intervening intron sequences of SEQ ID NO: X, if present, are removed. In some instances—when a referenced genomic DNA sequence lacks intervening intron sequences—a cDNA sequence may be identical to its corresponding genomic DNA sequence.

Genomic DNA sequence. The term "genomic DNA sequence" means a DNA sequence found in the genome of a source organism (e.g., a eukaryotic or prokaryotic genome). In some instances, a genomic DNA sequence from a eukaryotic genome contains one or more intervening intron sequences that are removed from the primary RNA transcript as a result of RNA splicing. Accordingly, the phrase "the genomic DNA sequence of SEQ ID NO: Y" intends the corresponding DNA sequence from the source organism which includes intervening intron sequences, if any, that are present before RNA splicing.

Mature polypeptide sequence: The term "mature polypeptide sequence" means the portion of the referenced polypeptide sequence after any post-translational sequence modifications (such as N-terminal processing and/or C-terminal truncation). In some instances, the mature polypeptide sequence may be identical to the entire referenced polypeptide sequence. In one aspect, the mature polypeptide sequence is amino acids 1 to 770 of SEQ ID NO: 2 based on the SignalP program (Nielsen et al., 1997, *Protein Engineering* 10: 1-6) and the InterProScan program (The European Bioinformatics Institute) that predicts the absence of a signal peptide. In another aspect, the mature polypeptide sequence is amino acids 1 to 843 of SEQ ID NO: 4 based on the SignalP program and the InterProScan program that predicts the absence of a signal peptide. It is known in the art that a host cell may produce a mixture of two of more different mature polypeptide sequences (i.e., with a different C-terminal and/or N-terminal amino acid) expressed by the same polynucleotide.

Mature polypeptide coding sequence: The term "mature polypeptide coding sequence" means the portion of the referenced polynucleotide sequence (e.g., genomic or cDNA sequence) that encodes a mature polypeptide sequence. In some instances, the mature polypeptide coding sequence may be identical to the entire referenced polynucleotide sequence. In one aspect, the mature polypeptide coding sequence is nucleotides 1 to 2503 of SEQ ID NO: 1 based on the SignalP program (supra) and the InterProScan program (supra) that predicts the absence of a signal peptide coding sequence. In another aspect, the mature polypeptide coding sequence is nucleotides 1 to 2657 of SEQ ID NO: 3 based on the SignalP program and the InterProScan program that predicts the absence of a signal peptide coding sequence.

Fragment: The term "fragment" means a polypeptide having one or more (several) amino acids deleted from the amino and/or carboxyl terminus of a referenced polypeptide sequence. In one aspect, the fragment has bicarbonate transporter activity. In another aspect, a fragment contains at least 650 amino acid residues, e.g., at least 690 amino acid residues or at least 730 amino acid residues of SEQ ID NO: 2. In another aspect, a fragment contains at least 720 amino acid residues, e.g., at least 760 amino acid residues or at least 800 amino acid residues of SEQ ID NO: 4.

Subsequence: The term "subsequence" means a polynucleotide having one or more (several) nucleotides deleted from the 5' and/or 3' end of the referenced nucleotide sequence. In one aspect, the subsequence encodes a fragment having bicarbonate transporter activity. In another aspect, a subsequence contains at least 1950 nucleotides, e.g., at least 2070 nucleotides or at least 2190 nucleotides of SEQ ID NO: 1. In another aspect, a subsequence contains at least 2160 nucleotides, e.g., at least 2280 nucleotides or at least 2400 nucleotides of SEQ ID NO: 3.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

Expression: The term "expression" includes any step involved in the production of the polypeptide including, but not limited to, transcription, post-transcriptional modification, translation, post-translational modification, and secretion.

Nucleic acid construct: The term "nucleic acid construct" means a nucleic acid molecule—single-stranded or double-stranded—which is isolated from a naturally occurring gene, modified to contain segments of nucleic acids in a manner that would not otherwise exist in nature, or synthetic, wherein the nucleic acid molecule comprises one or more (several) control sequences.

Control sequence: The term "control sequence" means a nucleic acid sequence necessary for polypeptide expression. Control sequences may be native or foreign to the polynucleotide encoding the polypeptide, and native or foreign to each other. Such control sequences include, but are not limited to, a leader sequence, polyadenylation sequence, propeptide sequence, promoter sequence, signal peptide sequence, and transcription terminator sequence. The control sequences may be provided with linkers for the purpose of introducing specific restriction sites facilitating ligation of the control sequences with the coding region of the polynucleotide encoding a polypeptide.

Operably linked: The term "operably linked" means a configuration in which a control sequence is placed at an appropriate position relative to the coding sequence of a polynucleotide such that the control sequence directs the expression of the coding sequence.

Expression vector: The term "expression vector" means a linear or circular DNA molecule that comprises a polynucleotide encoding a polypeptide and is operably linked to control sequences, wherein the control sequences provide for expression of the polynucleotide encoding the polypeptide. At a minimum, the expression vector comprises a promoter sequence, and transcriptional and translational stop signal sequences.

Host cell: The term "host cell" means any cell type that is susceptible to transformation, transfection, transduction, and the like with a nucleic acid construct or expression vector comprising a polynucleotide of the present invention (e.g., a polynucleotide encoding a bicarbonate transporter). The term "host cell" encompasses any progeny of a parent cell that is not identical to the parent cell due to mutations that occur during replication.

Variant: The term "variant" means a polypeptide having activity, e.g., bicarbonate transporter activity, comprising an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding one or more (several), e.g., 1-3 amino acids, adjacent to an amino acid occupying a position.

Volumetric productivity: The term "volumetric productivity" refers to the amount of referenced product produced (e.g., the amount of a C4-dicarboxylic acid produced) per volume of the system used (e.g., the total volume of media and contents therein) per unit of time.

Fermentable medium: The term "fermentable medium" refers to a medium comprising one or more (several) sugars, such as glucose, fructose, sucrose, cellobiose, xylose, xylulose, arabinose, mannose, galactose, and/or soluble oligosaccharides, wherein the medium is capable, in part, of being converted (fermented) by a host cell into a desired product, such as a C4-dicarboxylic acid. In some instances, the fermentation medium is derived from a natural source, such as sugar cane, starch, or cellulose, and may be the result of pretreating the source by enzymatic hydrolysis (saccharification).

Reference to "about" a value or parameter herein includes aspects that are directed to that value or parameter per se. For example, description referring to "about X" includes the aspect "X".

As used herein and in the appended claims, the singular forms "a," "or," and "the" include plural referents unless the context clearly dictates otherwise. It is understood that the aspects of the invention described herein include "consisting" and/or "consisting essentially of" aspects.

Unless defined otherwise or clearly indicated by context, all technical and scientific terms used herein have the same meaning as commonly understood by one of ordinary skill in the art to which this invention belongs.

DETAILED DESCRIPTION OF THE INVENTION

The present invention describes, inter alia, the overexpression of specific genes in a host cell, such as a filamentous fungus (e.g., *Aspergillus*) to enhance the production of C4-dicarboxylic acids (e.g., malic acid). The invention encompasses the use of a heterologous gene for the expression of a bicarbonate transporter. The bicarbonate transporter can be any described bicarbonate transporter that is suitable for practicing the present invention. In one aspect, the bicarbonate transporter is a transporter that is overexpressed under culture conditions that produces C4-dicarboxylic acid in high titers. In one aspect, the bicarbonate transporter is a sulfate-bicarbonate transporter. The recombinant host cell may further comprise a heterologous polynucleotide encoding a C4-dicarboxylic acid transporter; a heterologous polynucleotide encoding a malate dehydrogenase; and/or a heterologous polynucleotide encoding a pyruvate carboxylase.

Bicarbonate Transporters and Polynucleotides Encoding Bicarbonate Transporters

In one aspect of the recombinant host cells and methods described herein, the bicarbonate transporter is selected from the group consisting of: (a) a bicarbonate transporter having at least 60% sequence identity to SEQ ID NO: 2 or 4, or the mature polypeptide sequence thereof; (b) a bicarbonate transporter encoded by a polynucleotide that hybridizes under low stringency conditions with (i) SEQ ID NO: 1 or 3, or the mature polypeptide coding sequence thereof, (ii) the cDNA sequence of SEQ ID NO: 1 or 3, or the mature polypeptide coding sequence thereof; or (iii) the full-length complementary strand of (i) or (ii); (c) a bicarbonate transporter encoded by a polynucleotide having at least 60% sequence identity to (iv) SEQ ID NO: 1 or 3, or the mature polypeptide coding sequence thereof, (v) the cDNA sequence of SEQ ID NO: 1 or 3, or the mature polypeptide coding sequence thereof; or (vi) the full-length complementary strand of (iv) or (v); (d) a bicarbonate transporter variant comprising a substitution, deletion, and/or insertion of one or more (several) amino acids of SEQ ID NO: 2 or 4, or the mature polypeptide sequence thereof; and (e) a fragment of a polypeptide of (a), (b), (c), or (d) that has bicarbonate transporter activity.

In one aspect, the bicarbonate transporter comprises or consists of an amino acid sequence of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 2 or 4, or the mature polypeptide sequence thereof. In one aspect, the bicarbonate transporter comprises an amino acid sequence that differs by no more than ten amino acids, e.g., by no more than five amino acids, by no more than four amino acids, by no more than three amino acids, by no more than two amino acids, or by one amino acid from SEQ ID NO: 2 or 4, or the mature polypeptide sequence thereof.

In one aspect, the bicarbonate transporter comprises or consists of an amino acid sequence of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 2 or the mature polypeptide sequence thereof. In one aspect, the bicarbonate transporter comprises an amino acid sequence that differs by no more than ten amino acids, e.g., by no more than five amino acids, by no more than four amino acids, by no more than three amino acids, by no more than two amino acids, or by one amino acid from SEQ ID NO: 2 or the mature polypeptide sequence thereof. In another aspect, the bicarbonate transporter comprises an amino acid sequence of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 4 or the mature polypeptide sequence thereof. In one aspect, the bicarbonate transporter comprises an amino acid sequence that differs by no more than ten amino acids, e.g., by no more than five amino acids, by no more than four amino acids, by no more than three amino acids, by no more than two amino acids, or by one amino acid from SEQ ID NO: 4 or the mature polypeptide sequence thereof.

In one aspect, the bicarbonate transporter comprises or consists of the amino acid sequence of SEQ ID NO: 2, the mature polypeptide sequence of SEQ ID NO: 2, an allelic variant thereof, or a fragment of the foregoing, having bicarbonate transporter activity. In another aspect, the bicarbonate transporter comprises or consists of the amino acid sequence of SEQ ID NO: 2. In another aspect, the bicarbonate transporter comprises or consists of the mature polypeptide sequence of SEQ ID NO: 2. In another aspect, the bicarbonate transporter comprises or consists of amino acids 1 to 770 of SEQ ID NO: 2.

In one aspect, the bicarbonate transporter comprises or consists of the amino acid sequence of SEQ ID NO: 4, the mature polypeptide sequence of SEQ ID NO: 4, an allelic variant thereof, or a fragment of the foregoing, having bicarbonate transporter activity. In another aspect, the bicarbonate transporter comprises or consists of the amino acid sequence of SEQ ID NO: 4. In another aspect, the bicarbonate transporter comprises or consists of the mature polypeptide sequence of SEQ ID NO: 4. In another aspect, the bicarbonate transporter comprises or consists of amino acids 1 to 843 of SEQ ID NO: 4.

In one aspect, the bicarbonate transporter is encoded by a polynucleotide that hybridizes under at least low stringency conditions, e.g., medium stringency conditions, medium-high stringency conditions, high stringency conditions, or very high stringency conditions with (i) SEQ ID NO: 1 or 3, or the mature polypeptide coding sequence thereof, (ii) the cDNA sequence of SEQ ID NO: 1 or 3, or the mature polypeptide coding sequence thereof; or (iii) the full-length complementary strand of (i) or (ii) (see, e.g., J. Sambrook, E. F. Fritsch, and T. Maniatus, 1989, *Molecular Cloning, A Laboratory Manual,* 2d edition, Cold Spring Harbor, N.Y.).

In one aspect, the bicarbonate transporter is encoded by a polynucleotide that hybridizes under at least low stringency conditions, e.g., medium stringency conditions, medium-high stringency conditions, high stringency conditions, or very high stringency conditions with (i) SEQ ID NO: 1 or the mature polypeptide coding sequence thereof, (ii) the cDNA sequence of SEQ ID NO: 1 or the mature polypeptide coding sequence thereof; or (iii) the full-length complementary strand of (i) or (ii). In another aspect, the bicarbonate transporter is encoded by a polynucleotide that hybridizes under at least low stringency conditions, e.g., medium stringency conditions, medium-high stringency conditions, high stringency conditions, or very high stringency conditions with (i) SEQ ID NO: 3 or the mature polypeptide coding sequence thereof, (ii) the cDNA sequence of SEQ ID NO: 3 or the mature polypeptide coding sequence thereof; or (iii) the full-length complementary strand of (i) or (ii).

In one aspect, the bicarbonate transporter is encoded by a polynucleotide having at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to (iv) SEQ ID NO: 1 or 3, or the mature polypeptide coding sequence thereof, (v) the cDNA sequence of SEQ ID NO: 1 or 3, or the mature polypeptide coding sequence thereof; or (vi) the full-length complementary strand of (iv) or (v).

In one aspect, the bicarbonate transporter is encoded by a polynucleotide having at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to (iv) SEQ ID NO: 1 or the mature polypeptide coding sequence thereof, (v) the cDNA sequence of SEQ ID NO: 1 or the mature polypeptide coding sequence thereof; or (vi) the full-length complementary strand of (iv) or (v).

In one aspect, the bicarbonate transporter is encoded by a polynucleotide having at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to (iv) SEQ ID NO: 3 or the mature polypeptide coding sequence thereof, (v) the cDNA sequence of SEQ ID NO: 3 or the mature polypeptide coding sequence thereof; or (vi) the full-length complementary strand of (iv) or (v).

In one aspect, the bicarbonate transporter is encoded by SEQ ID NO: 1 or 3, or the mature polypeptide coding sequence thereof. In one aspect, the bicarbonate transporter is encoded by SEQ ID NO: 1 or the mature polypeptide coding sequence thereof. In one aspect, the bicarbonate transporter is encoded by SEQ ID NO: 1. In one aspect, the bicarbonate transporter is encoded by SEQ ID NO: 3 or the mature polypeptide coding sequence thereof. In one aspect, the bicarbonate transporter is encoded by SEQ ID NO: 3. In one aspect, the bicarbonate transporter is encoded by a subsequence of SEQ ID NO: 1 or 3, wherein the subsequence encodes a polypeptide having bicarbonate transporter activity. In one aspect, the bicarbonate transporter is encoded by a subsequence of SEQ ID NO: 1, wherein the subsequence encodes a polypeptide having bicarbonate transporter activity. In one aspect, the bicarbonate transporter is encoded by a subsequence of SEQ ID NO: 3, wherein the subsequence encodes a polypeptide having bicarbonate transporter activity.

In one aspect, the bicarbonate transporter is a variant comprising a substitution, deletion, and/or insertion of one or more (several) amino acids of SEQ ID NO: 2 or 4, or the mature polypeptide sequence thereof. In one aspect, the bicarbonate transporter is a variant comprising a substitution, deletion, and/or insertion of one or more (several) amino acids of SEQ ID NO: 2. In one aspect, the bicarbonate transporter is a variant comprising a substitution, deletion, and/or insertion of one or more (several) amino acids of the mature polypeptide sequence of SEQ ID NO: 2. In one aspect, the bicarbonate transporter is a variant comprising a substitution, deletion, and/or insertion of one or more (several) amino acids of SEQ ID NO: 4. In one aspect, the bicarbonate transporter is a variant comprising a substitution, deletion, and/or insertion of one or more (several) amino acids of the mature polypeptide sequence of SEQ ID NO: 4.

Preferably, amino acid changes are of a minor nature, that is conservative amino acid substitutions or insertions that do not significantly affect the folding and/or activity of the protein; small deletions, typically of one to about 30 amino acids; small amino-terminal or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for bicarbonate transporter activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to the referenced parent polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

In some aspects, the total number of amino acid substitutions, deletions and/or insertions of SEQ ID NO: 2 or 4, or the mature polypeptide sequence thereof, is not more than 10, e.g., not more than 1, 2, 3, 4, 5, 6, 7, 8 or 9.

In another aspect, the bicarbonate transporter is a fragment of SEQ ID NO: 2 or 4, or the mature polypeptide sequence thereof, wherein the fragment has bicarbonate transporter activity. In one aspect, the bicarbonate transporter is a fragment of SEQ ID NO: 2 or the mature polypeptide sequence thereof, wherein the fragment has bicarbonate transporter activity. In one aspect, the fragment contains at least 650 amino acid residues, e.g., preferably at least 690 amino acid residues, or at least 730 amino acid residues of SEQ ID NO: 2. In one aspect, the fragment contains a bicarbonate transporter domain, e.g., the putative transporter domain of amino acids 280 to 556 of SEQ ID NO: 2. In another aspect, the bicarbonate transporter is a fragment of SEQ ID NO: 4 or the mature polypeptide sequence thereof, wherein the fragment has bicarbonate transporter activity. In one aspect, the fragment contains at least 720 amino acid residues, e.g., preferably at least 760 amino acid residues, or at least 800 amino acid residues of SEQ ID NO: 4. In one aspect, the fragment contains a bicarbonate transporter domain, e.g., the putative transporter domain of amino acids 192 to 480 of SEQ ID NO: 4.

The bicarbonate transporter may be a fused polypeptide or cleavable fusion polypeptide in which another polypeptide is fused at the N-terminus or the C-terminus of the polypeptide of the present invention. A fused polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Techniques used to isolate or clone a polynucleotide—such as a polynucleotide encoding a bicarbonate transporter—as well as any other polypeptide used in any of the aspects mentioned herein, are known in the art and include isolation from genomic DNA, preparation from cDNA, or a combination thereof. The cloning of the polynucleotides from such genomic DNA can be effected, e.g., by using the well known polymerase chain reaction (PCR) or antibody screening of expression libraries to detect cloned DNA fragments with shares structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Aspergillus*, or another or related organism, and thus, for example, may be an allelic or species variant of the polypeptide encoding region of the nucleotide sequence.

The polynucleotide of SEQ ID NO: 1 or 3, or a subsequence thereof; as well as the amino acid sequence of SEQ ID NO: 2 or 4; or a fragment thereof; may be used to design nucleic acid probes to identify and clone DNA encoding a bicarbonate transporter from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, e.g., at least 14 nucleotides, at least 25 nucleotides, at least 35 nucleotides, at least 70 nucleotides in lengths. The probes may be longer, e.g., at least 100 nucleotides, at least 200 nucleotides, at least 300 nucleotides, at least 400 nucleotides, at least 500 nucleotides in lengths. Even longer probes may be used, e.g., at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having bicarbonate transporter activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1 or 3, or a subsequence thereof, the carrier material is preferably used in a Southern blot.

For purposes of the present invention, hybridization indicates that the polynucleotide hybridizes to a labeled nucleic acid probe corresponding to SEQ ID NO: 1 or 3, the mature polypeptide coding sequence of SEQ ID NO: 1 or 3, or the full-length complementary strand thereof, or a subsequence of the foregoing; under very low to very high stringency conditions. Molecules to which the nucleic acid probe hybridizes under these conditions can be detected using, for example, X-ray film.

In one aspect, the nucleic acid probe is SEQ ID NO: 1 or 3. In another aspect, the nucleic acid probe is the mature polypeptide coding sequence of SEQ ID NO: 1 or 3. In another aspect, the nucleic acid probe is the mature polypeptide coding sequence of SEQ ID NO: 1. In another aspect, the nucleic acid probe is SEQ ID NO: 1. In another aspect, the nucleic acid probe is the mature polypeptide coding sequence of SEQ ID NO: 3. In another aspect, the nucleic acid probe is SEQ ID NO: 3. In another aspect, the nucleic acid probe is a polynucleotide that encodes the polypeptide of SEQ ID NO: 2 or a fragment thereof. In another aspect, the nucleic acid probe is a polynucleotide that encodes the polypeptide of SEQ ID NO: 4 or a fragment thereof.

For long probes of at least 100 nucleotides in length, very low to very high stringency conditions are defined as prehybridization and hybridization at 42° C. in 5×SSPE, 0.3% SDS, 200 micrograms/mL sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 45° C. (very low stringency), at 50° C. (low stringency), at 55° C. (medium stringency), at 60° C. (medium-high stringency), at 65° C. (high stringency), and at 70° C. (very high stringency).

For short probes of about 15 nucleotides to about 70 nucleotides in length, stringency conditions are defined as prehybridization and hybridization at about 5° C. to about 10° C. below the calculated $T_m$ using the calculation according to Bolton and McCarthy (1962, *Proc. Natl. Acad. Sci. USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per mL following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

The bicarbonate transporter of the present invention may be obtained from a microorganism of any genus. As used herein, the term "obtained from" in connection with a given source shall mean that the polypeptide encoded by a polynucleotide is produced by the source or by a cell in which the polynucleotide from the source has been inserted.

The bicarbonate transporter may be a bacterial bicarbonate transporter. For example, the bicarbonate transporter may be a Gram-positive bacterial polypeptide such as a *Bacillus, Streptococcus, Streptomyces, Staphylococcus, Enterococcus, Lactobacillus, Lactococcus, Clostridium, Geobacillus*, or *Oceanobacillus* bicarbonate transporter, or a Gram-negative bacterial polypeptide such as an *E. coli, Pseudomonas, Salmonella, Campylobacter, Helicobacter, Flavobacterium, Fusobacterium, Ilyobacter, Neisseria*, or *Ureaplasma* bicarbonate transporter.

In one aspect, the bicarbonate transporter is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* bicarbonate transporter.

In another aspect, the bicarbonate transporter is a *Streptococcus equisimilis, Streptococcus pyogenes, Streptococcus uberis*, or *Streptococcus equi* subsp. *Zooepidemicus* bicarbonate transporter. In another aspect, the bicarbonate transporter is a *Streptomyces achromogenes, Streptomyces avermitilis, Streptomyces coelicolor, Streptomyces griseus*, or *Streptomyces lividans* bicarbonate transporter.

The bicarbonate transporter may be a fungal bicarbonate transporter. In one aspect, the fungal bicarbonate transporter is a yeast bicarbonate transporter such as a *Candida, Kluyveromyces, Pichia, Saccharomyces, Schizosaccharomyces*, or *Yarrowia* bicarbonate transporter.

In another aspect, the fungal bicarbonate transporter is a filamentous fungal bicarbonate transporter such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* bicarbonate transporter.

In another aspect, the bicarbonate transporter is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* bicarbonate transporter.

In another aspect, the bicarbonate transporter is an *Acremonium cellulolyticus, Aspergillus aculeatus, Aspergillus awamori, Aspergillus flavus, Aspergillus fumigatus, Aspergillus foetidus, Aspergillus japonicus, Aspergillus nidulans, Aspergillus niger, Aspergillus oryzae, Aspergillus sojae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei*, or *Trichoderma viride* bicarbonate transporter.

In one aspect, the bicarbonate transporter is an *Aspergillus* bicarbonate transporter, such as an *Aspergillus oryzae* bicarbonate transporter. In one aspect, the bicarbonate transporter an *Aspergillus oryzae* bicarbonate transporter of SEQ ID NO: 2. In another aspect, the bicarbonate transporter an *Aspergillus oryzae* bicarbonate transporter of SEQ ID NO: 4.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

The bicarbonate transporter may also be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. The polynucleotide encoding a bicarbonate transporter may then be derived by similarly screening a genomic or cDNA library of another microorganism or mixed DNA sample. Once a polynucleotide encoding a bicarbonate transporter has been detected with suitable probe(s) as described herein, the sequence may be isolated or cloned by utilizing techniques that are known to those of ordinary skill in the art (see, e.g., J. Sambrook, E. F. Fritsch, and T. Maniatus, 1989, *Molecular Cloning, A Laboratory Manual,* 2d edition, Cold Spring Harbor, N.Y.).

C4-Dicarboxylic Acid Transporters and Polynucleotides Encoding C4-Dicarboxylic Acid Transporters In some aspects of the recombinant host cells and methods of use thereof, the host cells have C4-dicarboxylic acid transporter activity. In some aspects, the host cells comprise a heterologous polynucleotide encoding a C4-dicarboxylic acid transporter. The C4-dicarboxylic acid transporter can be any C4-dicarboxylic acid transporter that is suitable for practicing the invention. In one aspect, the C4-dicarboxylic acid transporter is present in the cytosol of the host cell.

In one aspect, the C4-dicarboxylic acid transporter is (a) a C4-dicarboxylic acid transporter having at least 60% sequence identity to SEQ ID NO: 6 or the mature polypeptide sequence thereof; (b) a C4-dicarboxylic acid transporter encoded by a polynucleotide that hybridizes under low stringency conditions with SEQ ID NO: 5, the mature polypeptide coding sequence thereof, or the full-length complementary strand of the foregoing; (c) a C4-dicarboxylic acid transporter encoded by a polynucleotide having at least 60% sequence identity to SEQ ID NO: 5, the mature polypeptide coding sequence thereof, or the full-length complementary strand of the foregoing; (d) a C4-dicarboxylic acid transporter variant comprising a substitution, deletion, and/or insertion of one or more (several) amino acids of SEQ ID NO: 6 or the mature polypeptide sequence thereof; and (e) a fragment of a polypeptide of (a), (b), (c), or (d) that has C4-dicarboxylic acid transporter activity.

In one aspect, the C4-dicarboxylic acid transporter comprises or consists of an amino acid sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 6 or the mature polypeptide sequence thereof. In one aspect, the C4-dicarboxylic acid transporter comprises an amino acid sequence that differs by no more than ten amino acids, e.g., by no more than five amino acids, by no more than four amino acids, by no more than three amino acids, by no more than two amino acids, or by one amino acid from SEQ ID NO: 6 or the mature polypeptide sequence thereof.

In one aspect, the C4-dicarboxylic acid transporter comprises or consists of the amino acid sequence of SEQ ID NO: 6, the mature polypeptide sequence of SEQ ID NO: 6, an allelic variant thereof, or a fragment of the foregoing, having C4-dicarboxylic acid transporter activity. In another aspect, the C4-dicarboxylic acid transporter comprises or consists of the amino acid sequence of SEQ ID NO: 6. In another aspect, the C4-dicarboxylic acid transporter comprises or consists of the mature polypeptide sequence of SEQ ID NO: 6. In another aspect, the C4-dicarboxylic acid transporter comprises or consists of amino acids 1 to 418 of SEQ ID NO: 6. In another aspect, the C4-dicarboxylic acid transporter comprises or consists of amino acids 18 to 418 of SEQ ID NO: 6.

In one aspect, the C4-dicarboxylic acid transporter is encoded by a polynucleotide that hybridizes under at least low stringency conditions, e.g., medium stringency conditions, medium-high stringency conditions, high stringency conditions, or very high stringency conditions with SEQ ID NO: 5, the mature polypeptide coding sequence thereof, or the full-length complementary strand of the foregoing (J. Sambrook, E.F. Fritsch, and T. Maniatis, 1989, supra).

In one aspect, the C4-dicarboxylic acid transporter is encoded by a polynucleotide having at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to SEQ ID NO: 5, the mature polypeptide coding sequence thereof, or the full-length complementary strand of the foregoing.

In one aspect, the C4-dicarboxylic acid transporter is encoded by SEQ ID NO: 5 or the mature polypeptide coding sequence thereof. In one aspect, the C4-dicarboxylic acid transporter is encoded by SEQ ID NO: 5. In one aspect, the C4-dicarboxylic acid transporter is encoded by the mature polypeptide coding sequence of SEQ ID NO: 5. In one aspect, the mature polypeptide coding sequence is nucleotides 1 to 1257 of SEQ ID NO: 5. In one aspect, the mature polypeptide coding sequence is nucleotides 52 to 1257 of SEQ ID NO: 5. In one aspect, the C4-dicarboxylic acid transporter is encoded by a subsequence of SEQ ID NO: 5, wherein the subsequence encodes a polypeptide having C4-dicarboxylic acid transporter activity. In one aspect, the subsequence contains at least 1065 nucleotides, e.g., at least 1125 nucleotides or at least 1185 nucleotides of SEQ ID NO: 5.

In one aspect, the C4-dicarboxylic acid transporter is a variant comprising a substitution, deletion, and/or insertion of one or more (several) amino acids of SEQ ID NO: 6 or the mature polypeptide sequence thereof, as described supra. In one aspect, the C4-dicarboxylic acid transporter is a variant comprising a substitution, deletion, and/or insertion of one or more (several) amino acids of SEQ ID NO: 6. In one aspect, the C4-dicarboxylic acid transporter is a variant comprising a substitution, deletion, and/or insertion of one or more (several) amino acids of the mature polypeptide sequence of SEQ ID NO: 6. In some aspects, the total number of amino acid substitutions, deletions and/or insertions of SEQ ID NO: 6 or the mature polypeptide sequence thereof is not more than 10, e.g., not more than 1, 2, 3, 4, 5, 6, 7, 8 or 9.

In another aspect, the C4-dicarboxylic acid transporter is a fragment of SEQ ID NO: 6 or the mature polypeptide sequence thereof, wherein the fragment has C4-dicarboxylic acid transporter activity. In one aspect, the fragment contains at least 355 amino acid residues, e.g., at least 375 amino acid residues, or at least 395 amino acid residues of SEQ ID NO: 6.

The C4-dicarboxylic acid transporter may also be an allelic variant or artificial variant of a C4-dicarboxylic acid transporter.

The C4-dicarboxylic acid transporter can also include fused polypeptides or cleavable fusion polypeptides, as described supra.

Techniques used to isolate or clone a polynucleotide encoding a C4-dicarboxylic acid transporter are described supra.

The polynucleotide sequence of SEQ ID NO: 5 or a subsequence thereof; as well as the amino acid sequence of SEQ ID NO: 6 or a fragment thereof; may be used to design nucleic acid probes to identify and clone DNA encoding C4-dicarboxylic acid transporter from strains of different genera or species, as described supra. Such probes are encompassed by the present invention. A genomic DNA or cDNA library prepared from such other organisms may be screened for DNA that hybridizes with the probes described above and encodes a C4-dicarboxylic acid transporter, as described supra.

In one aspect, the nucleic acid probe is SEQ ID NO: 5. In another aspect, the nucleic acid probe is the mature polypeptide sequence of SEQ ID NO: 5. In another aspect, the nucleic acid probe is a polynucleotide sequence that encodes SEQ ID NO: 6, the mature polypeptide sequence thereof, or a fragment of the foregoing.

For long probes of at least 100 nucleotides in length, very low to very high stringency and washing conditions are defined as described supra. For short probes of about 15 nucleotides to about 70 nucleotides in length, stringency and washing conditions are defined as described supra.

The C4-dicarboxylic acid transporter may be obtained from microorganisms of any genus. In one aspect, the C4-dicarboxylic acid transporter may be a bacterial, a yeast, or a filamentous fungal C4-dicarboxylic acid transporter obtained from the microorganisms described herein. In another aspect, the C4-dicarboxylic acid transporter is an *Aspergillus* C4-dicarboxylic acid transporter, such as an *Aspergillus aculeatus* C4-dicarboxylic acid transporter, e.g., the *Aspergillus aculeatus* C4-dicarboxylic acid transporter of SEQ ID NO: 6.

Other C4-dicarboxylic acid transporter that can be used with the host cells and methods of use described herein include, but are not limited to, the *Aspergillus flavus* C4 dicarboxylic acid transporter (AFLA_107340), the *Aspergillus oryzae* C4-dicarboxylic acid transporter of SEQ ID NO: 27 (encoded by the polynucleotide sequence of SEQ ID NO: 26; see US 2011/0053233), the *Aspergillus terreus* C4-dicarboxylic acid transporter of SEQ ID NO: 29 (encoded by the polynucleotide sequence of SEQ ID NO: 28; see US 2011/0053233), the *Schizosaccharomyces pombe* C4-dicarboxylic acid transporter of SEQ ID NO: 32 (encoded by the polynucleotide sequence of SEQ ID NO: 30 or 31; see US 2011/0053233), the *Aspergillus aculeatus* C4-dicarboxylic acid transporter of SEQ ID NO: 34 (encoded by the polynucleotide sequence of SEQ ID NO: 33; see U.S. application Ser. No. 13/165,696, entitled "Polypeptides Having C4-dicarboxylic acid Transporter Activity and Polynucleotides Encoding Same" filed Jun. 21, 2011), the *Aspergillus aculeatus* C4-dicarboxylic acid transporter of SEQ ID NO: 36 (encoded by the polynucleotide sequence of SEQ ID NO: 35; see U.S. application Ser. No. 13/165,696, supra), the *Schizosaccharomyces japonicus* C4-dicarboxylic acid transporter of SEQ ID NO: 39 (encoded by the polynucleotide sequence of SEQ ID NO: 37 or 38; see PCT/US11/38881, entitled "C4-dicarboxylic acid Production in Filamentous Fungi" filed Jun. 2, 2011), the *Aspergillus clavatus* C4-dicarboxylic acid transporter of SEQ ID NO: 41 (encoded by the polynucleotide sequence of SEQ ID NO: 40; see U.S. application Ser. No. 13/165,719, entitled "Methods for Improving C4-dicarboxylic acid Production in Filamentous Fungi" filed Jun. 21, 2011), the *Aspergillus fumigatus* C4-dicarboxylic acid transporter of SEQ ID NO: 43 (encoded by the polynucleotide sequence of SEQ ID NO: 42; see U.S. application Ser. No. 13/165,719, supra), or any aspect of the C4-dicarboxylic acid transporter described in the respective reference therein. Any aspect described herein related to sequence identity, hybridization, amino acid modifications (e.g., substitutions, deletions, and/or insertions), fragments or subsequences thereof is embraced for the C4-dicarboxylic acid transporters above.

The invention embraces any aspect of sequence identity, hybridization, variants and fragments described herein as applied to the C4-dicarboxylic acid transporter polypeptide sequences and polynucleotide sequences described above. For example, in one aspect, the C4-dicarboxylic acid transporter is (a) a C4-dicarboxylic acid transporter having at least 60%, e.g., at least 65%, at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to SEQ ID NO: 27, 29, 32, 34, 36, 39, 41, or 43, or the mature polypeptide sequence thereof; (b) a C4-dicarboxylic acid transporter encoded by a polynucleotide that hybridizes under low stringency conditions, e.g., medium stringency conditions, medium-high stringency conditions, high stringency conditions, or very high stringency conditions with (i) SEQ ID NO: 26, 28, 30, 31, 33, 35, 37, 38, 40, or 42, or the mature polypeptide coding sequence thereof, (ii) the cDNA sequence of SEQ ID NO: 26, 28, 30, 31, 33, 35, 37, 38, 40, or 42, or the mature polypeptide coding sequence thereof, or (iii) the full-length complementary strand of the (i) or (ii); (c) a C4-dicarboxylic acid transporter encoded by a polynucleotide having at least 60%, e.g., at least 65%, at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to (iv) SEQ ID NO: 26, 28, 30, 31, 33, 35, 37, 38, 40, or 42, or the mature polypeptide coding sequence thereof, (v) the cDNA sequence of SEQ ID NO: 26, 28, 30, 31, 33, 35, 37, 38, 40, or 42, or the mature polypeptide coding sequence thereof, or (vi) the full-length complementary strand of the (iv) or (v); (d) a C4-dicarboxylic acid transporter variant comprising a substitution, deletion, and/or insertion of one or more (several) amino acids of SEQ ID NO: 27, 29, 32, 34, 36, 39, 41, or 43, or the mature polypeptide sequence thereof; or (e) a fragment of a polypeptide of (a), (b), (c), or (d) that has C4-dicarboxylic acid transporter activity.

The C4-dicarboxylic acid transporter may also be identified and obtained from other sources including microorganisms isolated from nature (e.g., soil, composts, water, etc.) or DNA samples obtained directly from natural materials (e.g., soil, composts, water, etc.) as described supra.

Malate Dehydrogenases and Polynucleotides Encoding Malate Dehydrogenases

In some aspects of the recombinant host cells and methods of use thereof, the host cells have malate dehydrogenase activity. In some aspects, the host cells comprise a heterologous polynucleotide encoding a malate dehydrogenase. The malate dehydrogenase can be any malate dehydrogenase that is suitable for practicing the invention. In one aspect, the malate dehydrogenase is an enzyme that is present in the cytosol of the host cell.

In one aspect of the recombinant host cells and methods described herein, the malate dehydrogenase is (a) a malate dehydrogenase having at least 60% sequence identity to SEQ ID NO: 8 or the mature polypeptide sequence thereof; (b) a malate dehydrogenase encoded by a polynucleotide that hybridizes under low stringency conditions with (i) SEQ ID NO: 7 or the mature polypeptide coding sequence thereof, (ii) the cDNA sequence of SEQ ID NO: 7 or the mature polypeptide coding sequence thereof, or (iii) the full-length complementary strand of (i) or (ii); (c) a malate dehydrogenase encoded by a polynucleotide having at least 60% sequence identity to (iv) SEQ ID NO: 7 or the mature polypeptide coding sequence thereof, (v) the cDNA sequence of SEQ ID NO: 7 or the mature polypeptide coding sequence thereof; or (vi) the full-length complementary strand of (iv) or (v); (d) a malate dehydrogenase variant comprising a substitution, deletion, and/or insertion of one or more (several) amino acids of SEQ ID NO: 8 or the mature polypeptide sequence thereof; and (e) a fragment of a polypeptide of (a), (b), (c), or (d) that has malate dehydrogenase activity.

In one aspect, the malate dehydrogenase comprises or consists of an amino acid sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 8 or the mature polypeptide sequence thereof. In one aspect, the malate dehydrogenase comprises an amino acid sequence that differs by no more than ten amino acids, e.g., by no more than five amino acids, by no more than four amino acids, by no more than three amino acids, by no more than two amino acids, or by one amino acid from SEQ ID NO: 8 or the mature polypeptide sequence thereof.

In one aspect, the malate dehydrogenase comprises or consists of the amino acid sequence of SEQ ID NO: 8, the mature polypeptide sequence of SEQ ID NO: 8, an allelic variant thereof, or a fragment of the foregoing, having malate dehydrogenase activity. In another aspect, the malate dehydrogenase comprises or consists of the amino acid sequence of SEQ ID NO: 8. In another aspect, the malate dehydrogenase comprises or consists of the mature polypeptide sequence of SEQ ID NO: 8. In another aspect, the malate dehydrogenase comprises or consists of amino acids 1 to 330 of SEQ ID NO: 8.

In one aspect, the malate dehydrogenase is encoded by a polynucleotide that hybridizes under at least low stringency conditions, e.g., medium stringency conditions, medium-high stringency conditions, high stringency conditions, or very high stringency conditions with (i) SEQ ID NO: 7 or the mature polypeptide coding sequence thereof, (ii) the cDNA sequence of SEQ ID NO: 7 or the mature polypeptide coding sequence thereof, or (iii) the full-length complementary strand of (i) or (ii) (J. Sambrook, E. F. Fritsch, and T. Maniatis, 1989, supra).

In one aspect, the malate dehydrogenase is encoded by a polynucleotide having at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to (iv) SEQ ID NO: 7 or the mature polypeptide coding sequence thereof, (v) the cDNA sequence of SEQ ID NO: 7 or the mature polypeptide coding sequence thereof; or (vi) the full-length complementary strand of (iv) or (v).

In one aspect, the malate dehydrogenase is encoded by SEQ ID NO: 7, or the mature polypeptide coding sequence thereof. In one aspect, the malate dehydrogenase is encoded by SEQ ID NO: 7. In one aspect, the malate dehydrogenase is encoded by the mature polypeptide coding sequence of SEQ ID NO: 7. In one aspect, the malate dehydrogenase is encoded by a subsequence of SEQ ID NO: 7, wherein the subsequence encodes a polypeptide having malate dehydrogenase activity. In one aspect, the subsequence contains at least 885 nucleotides, e.g., at least 930 nucleotides or at least 975 nucleotides of SEQ ID NO: 7.

In one aspect, the malate dehydrogenase is a variant comprising a substitution, deletion, and/or insertion of one or more (several) amino acids of SEQ ID NO: 8, or the mature polypeptide sequence thereof, as described supra. In one aspect, the malate dehydrogenase is a variant comprising a substitution, deletion, and/or insertion of one or more (several) amino acids of SEQ ID NO: 8. In one aspect, the malate dehydrogenase is a variant comprising a substitution, deletion, and/or insertion of one or more (several) amino acids of the mature polypeptide sequence of SEQ ID NO: 8. In some aspects, the total number of amino acid substitutions, deletions and/or insertions of the mature polypeptide sequence of SEQ ID NO: 8 or the mature polypeptide sequence thereof is not more than 10, e.g., not more than 1, 2, 3, 4, 5, 6, 7, 8 or 9.

In another aspect, the malate dehydrogenase is a fragment of SEQ ID NO: 8, or the mature polypeptide sequence thereof, wherein the fragment has malate dehydrogenase activity. In one aspect, the fragment contains at least 295 amino acid residues, e.g., at least 310 amino acid residues, or at least 325 amino acid residues of SEQ ID NO: 8.

The malate dehydrogenase may also be an allelic variant or artificial variant of a malate dehydrogenase.

The malate dehydrogenase can also include fused polypeptides or cleavable fusion polypeptides, as described supra.

Techniques used to isolate or clone a polynucleotide encoding a malate dehydrogenase are described supra.

The polynucleotide of SEQ ID NO: 7; or a subsequence thereof; as well as the amino acid sequence of SEQ ID NO: 8; or a fragment thereof; may be used to design nucleic acid probes to identify and clone DNA encoding malate dehydrogenases from strains of different genera or species, as described supra. Such probes are encompassed by the present invention. A genomic DNA or cDNA library prepared from such other organisms may be screened for DNA that hybridizes with the probes described above and encodes an malate dehydrogenase, as described supra.

In one aspect, the nucleic acid probe is SEQ ID NO: 7. In another aspect, the nucleic acid probe is the mature polypeptide coding sequence of SEQ ID NO: 7. In another aspect, the nucleic acid probe is a polynucleotide sequence that encodes SEQ ID NO: 8, the mature polypeptide sequence thereof, or a fragment of the foregoing.

For long probes of at least 100 nucleotides in length, very low to very high stringency and washing conditions are defined as described supra. For short probes of about 15 nucleotides to about 70 nucleotides in length, stringency and washing conditions are defined as described supra.

The malate dehydrogenase may be obtained from microorganisms of any genus. In one aspect, the malate dehydrogenase may be a bacterial, a yeast, or a filamentous fungal malate dehydrogenase obtained from the microorganisms described herein. In another aspect, the malate dehydrogenase is an *Aspergillus oryzae* malate dehydrogenase, e.g., the *Aspergillus oryzae* malate dehydrogenase of SEQ ID NO: 8.

Other malate dehydrogenases that can be used to practice the present invention include, but are not limited to, a *Aspergillus nidulans* malate dehydrogenase (AN6717.1; SIMS et al., 2004, *Mycol. Res.* 108: 853-857); *Aspergillus niger* malate dehydrogenase (An16g00120; Pel et al., 2007, *Nature Biotechnology* 25: 221-231); *Phytophthora infestans* malate dehydrogenase (PITG 13614.1; Calcagno et al., 2009, *Mycological Research* 113: 771-781); *Saccharomyces cerevisiae* malate dehydrogenase (YKL085W; McAlister-Henn and Thompson, 1987, *J Bacteriol.* 169: 5157-5166); *Talaromyces emersonii* malate dehydrogenase (AF439996, AF487682; Maloney et al., 2004, *Eur. J. Biochem.* 271: 3115-3126); and *Ustilago maydis* malate dehydrogenase (um00403, um11161; McCann and Snetselaar, 2008, *Fungal Genetics and Biology* 45: S77-S87), the *Aspergillus oryzae* malate dehydrogenase of SEQ ID NO: 45 (encoded by the polynucleotide sequence of SEQ ID NO: 44; see U.S. application Ser. No. 12/870,523, entitled "Methods for Improving Malic Acid Production in Filamentous Fungi" filed Aug. 27, 2010), or any aspect of the malate dehydrogenase described in the respective reference therein. Any aspect described herein related to sequence identity, hybridization, amino acid modifications (e.g., substitutions, deletions, and/or insertions), fragments or subsequences thereof is embraced for the malate dehydrogenases above.

The invention embraces any aspect of sequence identity, hybridization, variants and fragments described herein as applied to the malate dehydrogenase polypeptide sequences and polynucleotide sequences described above. For example, in one aspect, the malate dehydrogenase is (a) a malate dehydrogenase having at least 60%, e.g., at least 65%, at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to SEQ ID NO: 45, or the mature polypeptide sequence thereof; (b) a malate dehydrogenase encoded by a polynucleotide that hybridizes under low stringency conditions, e.g., medium stringency conditions, medium-high stringency conditions, high stringency conditions, or very high stringency conditions with (i) SEQ ID NO: 44 or the mature polypeptide coding sequence thereof, (ii) the cDNA sequence of SEQ ID NO: 44 or the mature polypeptide coding sequence thereof, or (iii) the full-length complementary strand of the (i) or (ii); (c) a malate dehydrogenase encoded by a polynucleotide having at least 60%, e.g., at least 65%, at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to (iv) SEQ ID NO: 44 or the mature polypeptide coding sequence thereof, (v) the cDNA sequence of SEQ ID NO: 44 or the mature polypeptide coding sequence thereof, or (vi) the full-length complementary strand of the (iv) or (v); (d) a malate dehydrogenase variant comprising a substitution, deletion, and/or insertion of one or more (several) amino acids of SEQ ID NO: 45 or the mature polypeptide sequence thereof; or (e) a fragment of a polypeptide of (a), (b), (c), or (d) that has malate dehydrogenase activity.

The malate dehydrogenase may also be identified and obtained from other sources including microorganisms isolated from nature (e.g., soil, composts, water, etc.) or DNA samples obtained directly from natural materials (e.g., soil, composts, water, etc.) as described supra.

Pyruvate Carboxylases and Polynucleotides Encoding Pyruvate Carboxylases

In some aspects of the recombinant host cells and methods of use thereof, the host cells have pyruvate carboxylase activity. In some aspects, the host cells comprise a heterologous polynucleotide encoding a pyruvate carboxylase. The pyruvate carboxylase can be any pyruvate carboxylase that is suitable for practicing the invention. In one aspect, the pyruvate carboxylase is an enzyme that is present in the cytosol of the host cell.

In one aspect of the recombinant host cells and methods described herein, the pyruvate carboxylase is (a) a pyruvate carboxylase having at least 60% sequence identity to SEQ ID NO: 10 or the mature polypeptide sequence thereof; (b) a pyruvate carboxylase encoded by a polynucleotide that hybridizes under low stringency conditions with (i) SEQ ID NO: 9 or the mature polypeptide coding sequence thereof, (ii) the cDNA sequence of SEQ ID NO: 9 or the mature polypeptide coding sequence thereof, or (iii) the full-length complementary strand of (i) or (ii); (c) a pyruvate carboxylase encoded by a polynucleotide having at least 60% sequence identity to (iv) SEQ ID NO: 9 or the mature polypeptide coding sequence thereof, (v) the cDNA sequence of SEQ ID NO: 9 or the mature polypeptide coding sequence thereof; or (vi) the full-length complementary strand of (iv) or (v); (d) a pyruvate carboxylase variant comprising a substitution, deletion, and/or insertion of one or more (several) amino acids of SEQ ID NO: 10 or the mature polypeptide sequence thereof; and (e) a fragment of a polypeptide of (a), (b), (c), or (d) that has pyruvate carboxylase activity.

In one aspect, the pyruvate carboxylase comprises or consists of an amino acid sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 10, or the mature polypeptide sequence thereof. In one aspect, the pyruvate carboxylase comprises an amino acid sequence that differs by no more than ten amino acids, e.g., by no more than five amino acids, by no more than four amino acids, by no more than three amino acids, by no more than two amino acids, or by one amino acid from SEQ ID NO: 10 or the mature polypeptide sequence thereof.

In one aspect, the pyruvate carboxylase comprises or consists of the amino acid sequence of SEQ ID NO: 10, the mature polypeptide sequence of SEQ ID NO: 10, an allelic variant thereof, or a fragment of the foregoing, having pyruvate carboxylase activity. In another aspect, the pyruvate carboxylase comprises or consists of the amino acid sequence of SEQ ID NO: 10. In another aspect, the pyruvate carboxylase comprises or consists of the mature polypeptide sequence of SEQ ID NO: 10. In another aspect, the pyruvate carboxylase comprises or consists of amino acids 1 to 1193 of SEQ ID NO: 10.

In one aspect, the pyruvate carboxylase is encoded by a polynucleotide that hybridizes under at least low stringency conditions, e.g., medium stringency conditions, medium-high stringency conditions, high stringency conditions, or very high stringency conditions with (i) SEQ ID NO: 9 or the mature polypeptide coding sequence thereof, (ii) the cDNA sequence of SEQ ID NO: 9 or the mature polypeptide coding sequence thereof, or (iii) the full-length complementary strand of (i) or (ii) (J. Sambrook, E. F. Fritsch, and T. Maniatis, 1989, supra).

In one aspect, the pyruvate carboxylase is encoded by a polynucleotide having at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to (iv) SEQ ID NO: 9 or the mature polypeptide coding sequence thereof, (v) the cDNA sequence of SEQ ID NO: 9 or the mature polypeptide coding sequence thereof; or (vi) the full-length complementary strand of (iv) or (v).

In one aspect, the pyruvate carboxylase is encoded by SEQ ID NO: 9 or the mature polypeptide coding sequence thereof. In one aspect, the pyruvate carboxylase is encoded by SEQ ID NO: 9. In one aspect, the pyruvate carboxylase is encoded by the mature polypeptide coding sequence of SEQ ID NO: 9. In one aspect, the pyruvate carboxylase is encoded by a subsequence of SEQ ID NO: 9, wherein the subsequence encodes a polypeptide having pyruvate carboxylase activity. In one aspect, the subsequence contains at least 3060 nucleotides, e.g., at least 3240 nucleotides or at least 3420 nucleotides of SEQ ID NO: 9.

In one aspect, the pyruvate carboxylase is a variant comprising a substitution, deletion, and/or insertion of one or more (several) amino acids of SEQ ID NO: 10, or the mature polypeptide sequence thereof, as described supra. In one aspect, the pyruvate carboxylase is a variant comprising a substitution, deletion, and/or insertion of one or more (several) amino acids of SEQ ID NO: 10. In one aspect, the pyruvate carboxylase is a variant comprising a substitution, deletion, and/or insertion of one or more (several) amino acids of the mature polypeptide sequence of SEQ ID NO: 10. In some aspects, the total number of amino acid substitutions, deletions and/or insertions of SEQ ID NO: 10 or the mature polypeptide sequence thereof is not more than 10, e.g., not more than 1, 2, 3, 4, 5, 6, 7, 8 or 9.

In another aspect, the pyruvate carboxylase is a fragment of SEQ ID NO: 10, or the mature polypeptide sequence thereof, wherein the fragment has pyruvate carboxylase activity. In one aspect, the fragment contains at least 1020 amino acid residues, e.g., at least 1080 amino acid residues, or at least 1140 amino acid residues of SEQ ID NO: 10.

The pyruvate carboxylase may also be an allelic variant or artificial variant of a pyruvate carboxylase.

The pyruvate carboxylase can also include fused polypeptides or cleavable fusion polypeptides, as described supra.

The pyruvate carboxylase can also be a variant of a mitochondrial pyruvate carboxylase, such that in vivo importation into the mitochondria is reduced thereby increasing the level of the pyruvate carboxylase variant in the cytosol.

Techniques used to isolate or clone a polynucleotide encoding a pyruvate carboxylase are described supra.

The polynucleotide of SEQ ID NO: 9 or a subsequence thereof, as well as the amino acid sequence of SEQ ID NO: 10 or a fragment thereof, may be used to design nucleic acid probes to identify and clone DNA encoding pyruvate carboxylases from strains of different genera or species, as described supra. Such probes are encompassed by the present invention. A genomic DNA or cDNA library prepared from such other organisms may be screened for DNA that hybridizes with the probes described above and encodes a pyruvate carboxylase, as described supra.

In one aspect, the nucleic acid probe is SEQ ID NO: 9. In another aspect, the nucleic acid probe is the mature polypeptide coding sequence of SEQ ID NO: 9. In another aspect, the nucleic acid probe is a polynucleotide sequence that encodes SEQ ID NO: 10, the mature polypeptide sequence thereof, or a fragment of the foregoing.

For long probes of at least 100 nucleotides in length, very low to very high stringency and washing conditions are defined as described supra. For short probes of about 15 nucleotides to about 70 nucleotides in length, stringency and washing conditions are defined as described supra.

The pyruvate carboxylase may be obtained from microorganisms of any genus. In one aspect, the pyruvate carboxylase may be a bacterial, a yeast, or a filamentous fungal pyruvate carboxylase obtained from the microorganisms described herein. In another aspect, the pyruvate carboxylase is an *Aspergillus oryzae* pyruvate carboxylase, e.g., the *Aspergillus oryzae* pyruvate carboxylase of SEQ ID NO: 10.

Other pyruvate carboxylases that can be used to practice the present invention include, but are not limited to, a *Aspergillus clavatus* NRRL 1 pyruvate carboxylase (XP_001271664; Direct Submission, Submitted (26 Oct. 2006), The Institute for Genomic Research, 9712 Medical Center Drive, Rockville, Md. 20850, USA); *Aspergillus fumigatus* Af293 pyruvate carboxylase (XP_752054; Nierman et al., 2005, *Nature* 438: 1151-1156); *Aspergillus nidulans* FGSC A4 pyruvate carboxylase (XP_662066; Galagan et al., 2005, *Nature* 438: 1105-1115); *Aspergillus niger* pyruvate carboxylase (An15g02820; Pel et al., 2007, *Nature Biotechnology* 25: 221-231; ASPNG 5061; Panneman et al., Submitted (July 1998) to the EMBL/GenBank/DDBJ databases); *Aspergillus terreus* pyruvate carboxylase (093918; Direct Submission, Submitted (October 1998) The Institute for Genomic Research, 9712 Medical Center Drive, Rockville, Md. 20850, USA); *Magnaporthe grisea* 70-15 pyruvate carboxylase (XP_367852; Direct Submission, Submitted (26 Sep. 2005) Broad Institute of MIT and Harvard, 320 Charles Street, Cambridge, Mass. 02142, USA); *Neurospora crassa* OR74A pyruvate carboxylase (XP_965636; Galagan et al., 2003, *Nature* 422: 859-868); *Rhizopus oryzae* pyruvate carboxylase (RO3G_06931.1); *Saccharomyces cerevisiae* pyruvate carboxylase (NP_009777; Gaffeau et al., 1996, *Science* 274: 546-547); *Schizosaccharomyces pombe* pyruvate carboxylase (NP_595900; Direct Submission, Submitted (29 Jun. 2007) European *Schizosaccharomyces* genome sequencing project, Sanger Institute, The Wellcome Trust Genome Campus, Hinxton, Cambridge CB10 1SA); and *Ustilago maydis* pyruvate carboxylase (um01054; McCann and Snetselaar, 2008, *Fungal Genetics and Biology* 45: S77-S87). Any aspect described herein related to sequence identity, hybridization, amino acid modifications (e.g., substitutions, deletions, and/or insertions), fragments or subsequences thereof is embraced for the pyruvate carboxylases above.

The pyruvate carboxylase may also be identified and obtained from other sources including microorganisms isolated from nature (e.g., soil, composts, water, etc.) or DNA samples obtained directly from natural materials (e.g., soil, composts, water, etc.) as described supra.

Nucleic Acid Constructs

The present invention also relates to recombinant host cells and methods utilizing nucleic acid constructs comprising a heterologous polynucleotide encoding a bicarbonate transporter (and/or encoding a C4-dicarboxylic acid transporter, a malate dehydrogenase, or a pyruvate carboxylase) linked to one or more (several) control sequences that direct expression in a suitable host cell under conditions compatible with the control sequence(s). Such nucleic acid constructs may be used in any of the host cells and methods describe herein. The polynucleotides described herein may be manipulated in a variety of ways to provide for expression of a desired polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter sequence, a polynucleotide that is recognized by a host cell for expression of a polynucleotide encoding any polypeptide described herein (e.g., a bicarbonate transporter, a C4-dicarboxylic acid transpoter, a malate decarboxylase, or a pyruvate carboxlase). The promoter sequence contains transcriptional control sequences that mediate the expression of the polypeptide. The promoter may be any polynucleotide that shows transcriptional activity in the host cell of choice including mutant, truncated, and hybrid promoters, and may be obtained from genes encoding extracellular or intracellular polypeptides either homologous or heterologous to the host cell.

Each polynucleotide described herein may be operably linked to a promoter that is foreign to the polynucleotide. For example, in one aspect, the heterologous polynucleotide encoding a bicarbonate transporter is operably linked to a promoter that is foreign to the polynucleotide. In another aspect, the heterologous polynucleotide encoding C4-dicarboxylic acid is operably linked to promoter foreign to the polynucleotide. In another aspect, the heterologous polynucleotide encoding a malate dehydrogenase is operably linked to promoter foreign to the polynucleotide. In another aspect, the heterologous polynucleotide encoding a pyruvate carboxylase is operably linked to promoter foreign to the polynucleotide.

Examples of suitable promoters for directing the transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *E. coli* lac operon, *E. coli* trc promoter (Egon et al., 1988, Gene 69: 301-315), *Streptomyces coelicolor* agarase gene (dagA), and prokaryotic beta-lactamase gene (VIIIa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American*, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from a gene encoding a neutral alpha-amylase in Aspergilli in which the untranslated leader has been replaced by an untranslated leader from a gene encoding triose phosphate isomerase in Aspergilli; non-limiting examples include modified promoters from the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, which is recognized by a host cell to terminate transcription. The terminator sequence is operably linked to the 3'-terminus of the polynucleotide encoding the polypeptide. Any terminator that is functional in the host cell of choice may be used in the present invention.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase (gpd). Other useful terminators for yeast host cells are described by Romanos et al., 1992, supra.

The control sequence may also be a suitable leader sequence, when transcribed is a nontranslated region of an mRNA that is important for translation by the host cell. The leader sequence is operably linked to the 5'-terminus of the polynucleotide encoding the polypeptide. Any leader sequence that is functional in the host cell of choice may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence; a sequence operably linked to the 3'-terminus of the polynucleotide and, when transcribed, is recognized by the host cell as a signal to add polyadenosine residues to transcribed mRNA. Any polyadenylation sequence that is functional in the host cell of choice may be used.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present at the N-terminus of a polypeptide, the propeptide sequence is positioned next to the N-terminus of a polypeptide and the signal peptide sequence is positioned next to the N-terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant host cells and methods utilizing recombinant expression vectors comprising a heterologous polynucleotide encoding a bicarbonate transporter (and/or encoding a C4-dicarboxylic acid transporter, a malate dehydrogenase, or a pyruvate carboxylase); as well as a promoter; and transcriptional and translational stop signals. Such recombinant expression vectors may be used in any of the host cells and methods described herein. The various nucleotide and control sequences may be joined together to produce a recombinant expression vector that may include one or more (several) convenient restriction sites to allow for insertion or substitution of the polynucleotide encoding the polypeptide at such sites. Alternatively, the polynucleotide(s) may be expressed by inserting the polynucleotide(s) or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

In one aspect, each polynucleotide encoding a bicarbonate transporter, a C4-dicarboxylic acid transporter, a malate dehydrogenase, and/or a pyruvate carboxylase described herein is contained on an independent vector. In one aspect, at least two of the polynucleotides are contained on a single vector. In one aspect, at least three of the polynucleotides are contained on a single vector. In one aspect, all the polynucleotides encoding the bicarbonate transporter, the C4-dicarboxylic acid transporter, the malate dehydrogenase, and the pyruvate carboxylase are contained on a single vector.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, chloramphenicol, kanamycin, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide described herein may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

As described herein, the present invention relates to, inter alia, recombinant host cells comprising one or more (several) polynucleotide(s) described herein which may be operably linked to one or more (several) control sequences that direct the expression of one or more (several) of the described polypeptides for the recombinant production of a C4-dicarboxylic acid. The invention also embraces methods of using such host cells for the production of a C4-dicarboxylic acid. The host cell may comprise any one or combination of a plurality of the polynucleotides described. For example, in one aspect, the recombinant host cell comprises a heterologous polynucleotide encoding a bicarbonate transporter; and optionally comprises a heterologous polynucleotide encoding a C4-dicarboxylic acid transporter, a heterologous polynucleotide encoding a malate dehydrogenase, and/or a heterologous polynucleotide encoding pyruvate decarboxylase; wherein the host cell produces (or is capable of producing) a greater amount of a C4-dicarboxylic acid compared to the host cell without the heterologous polynucleotide encoding the bicarbonate transporter when cultivated under the same conditions.

In one aspect, the recombinant host cell comprises:

(1) a heterologous polynucleotide encoding a bicarbonate transporter, such as as a C4 bicarbonate transporter selected from: (a) a bicarbonate transporter having at least 60% sequence identity to SEQ ID NO: 2 or 4, or the mature polypeptide sequence thereof; (b) a bicarbonate transporter encoded by a polynucleotide that hybridizes under low stringency conditions with (i) SEQ ID NO: 1 or 3, or the mature polypeptide coding sequence thereof, (ii) the cDNA sequence of SEQ ID NO: 1 or 3, or the mature polypeptide coding sequence thereof; or (iii) the full-length complementary strand of (i) or (ii); (c) a bicarbonate transporter encoded by a polynucleotide having at least 60% sequence identity to (iv) SEQ ID NO: 1 or 3, or the mature polypeptide coding sequence thereof, (v) the cDNA sequence of SEQ ID NO: 1 or 3, or the mature polypeptide coding sequence thereof; or (vi) the full-length complementary strand of (iv) or (v); (d) a bicarbonate transporter variant comprising a substitution, deletion, and/or insertion of one or more (several) amino acids of SEQ ID NO: 2 or 4, or the mature polypeptide sequence thereof; and (e) a fragment of (a), (b), (c), or (d) that has bicarbonate transporter activity;

(2) an optional heterologous second polynucleotide encoding a C4-dicarboxylic acid transporter, such as a C4-dicarboxylic acid transporter selected from: (a) a C4-dicarboxylic acid transporter having at least 60% sequence identity to SEQ ID NO: 6 or the mature polypeptide sequence thereof; (b) a C4-dicarboxylic acid transporter encoded by a polynucleotide that hybridizes under low stringency conditions with SEQ ID NO: 5, the mature polypeptide coding sequence thereof, or the full-length complementary strand of the foregoing; (c) a C4-dicarboxylic acid transporter encoded by a polynucleotide having at least 60% sequence identity to SEQ ID NO: 5, the mature polypeptide coding sequence thereof, or the full-length complementary strand of the foregoing; (d) a C4-dicarboxylic acid transporter variant comprising a substitution, deletion, and/or insertion of one or more (several) amino acids of SEQ ID NO: 6 or the mature polypeptide sequence thereof; and (e) a fragment of a polypeptide of (a), (b), (c), or (d) that has C4-dicarboxylic acid transporter activity;

(3) an optional heterologous third polynucleotide encoding a malate dehydrogenase, such as a malate dehydrogenase selected from: (a) a malate dehydrogenase having at least 60% sequence identity to SEQ ID NO: 8 or the mature polypeptide sequence thereof; (b) a malate dehydrogenase encoded by a polynucleotide that hybridizes under low stringency conditions with (i) SEQ ID NO: 7 or the mature polypeptide coding sequence thereof, (ii) the cDNA sequence of SEQ ID NO: 7 or the mature polypeptide coding sequence thereof, or (iii) the full-length complementary strand of (i) or (ii); (c) a malate dehydrogenase encoded by a polynucleotide having at least 60% sequence identity to (iv) SEQ ID NO: 7 or the mature polypeptide coding sequence thereof, (v) the cDNA sequence of SEQ ID NO: 7 or the mature polypeptide coding sequence thereof; or (vi) the full-length complementary strand of (iv) or (v); (d) a malate dehydrogenase variant comprising a substitution, deletion, and/or insertion of one or more (several) amino acids of SEQ ID NO: 8 or the mature polypeptide sequence thereof; and (e) a fragment of a polypeptide of (a), (b), (c), or (d) that has malate dehydrogenase activity; and (4) an optional heterologous fourth polynucleotide encoding a pyruvate carboxylase, such as as a pyruvate carboxylase selected from: (a) a pyruvate carboxylase having at least 60% sequence identity to SEQ ID NO: 10 or the mature polypeptide sequence thereof; (b) a pyruvate carboxylase encoded by a polynucleotide that hybridizes under low stringency conditions with (i) SEQ ID NO: 9 or the mature polypeptide coding sequence thereof, (ii) the cDNA sequence of SEQ ID NO: 9 or the mature polypeptide coding sequence thereof, or (iii) the full-length complementary strand of (i) or (ii); (c) a pyruvate carboxylase encoded by a polynucleotide having at least 60% sequence identity to (iv) SEQ ID NO: 9 or the mature polypeptide coding sequence thereof, (v) the cDNA sequence of SEQ ID NO: 9 or the mature polypeptide coding sequence thereof; or (vi) the full-length complementary strand of (iv) or (v); (d) a pyruvate carboxylase variant comprising a substitution, deletion, and/or insertion of one or more (several) amino acids of SEQ ID NO: 10 or the mature polypeptide sequence thereof; and (e) a fragment of a polypeptide of (a), (b), (c), or (d) that has pyruvate carboxylase activity;

wherein the host cell produces (or is capable of producing) a greater amount of a C4-dicarboxylic acid (e.g., malic acid) compared to the host cell without the one or more (several) polynucleotide(s) (e.g., without the heterologous polynucleotide encoding a bicarbonate transporter), when cultivated under the same conditions.

A construct or vector (or multiple constructs or vectors) comprising the one or more (several) polynucleotide(s) is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source. The aspects described below apply to the host cells, per se, as well as methods using the host cells.

The host cell may be any cell capable of the recombinant production of a polypeptide of the present invention, e.g., a prokaryote or a eukaryote, and/or any cell capable of the recombinant production of a C4-dicarboxylic acid (e.g., malic acid).

The prokaryotic host cell may be any gram-positive or gram-negative bacterium. Gram-positive bacteria include, but not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may, for instance, be effected by protoplast transformation (see, e.g., Chang and Cohen, 1979, *Mol. Gen. Genet.* 168: 111-115), by using competent cells (see, e.g., Young and Spizizen, 1961, *J. Bacteriol.* 81: 823-829, or Dubnau and Davidoff-Abelson, 1971, *J. Mol. Biol.* 56: 209-221), by electroporation (see, e.g., Shigekawa and Dower, 1988, *Biotechniques* 6: 742-751), or by conjugation (see, e.g., Koehler and Thorne, 1987, *J. Bacteriol.* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (*Praha*) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios* 68: 189-207, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota (as defined by Hawksworth et al., *In, Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevi-*

*siae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus aculeatus, Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

In one aspect, the host cell is an *Aspergillus* host cell. In another aspect, the host cell is *Aspergillus oryzae*.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023 and Yelton et al., 1984, *Proc. Natl. Acad. Sci. USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

In some aspects, the host cell comprises one or more (several) polynucleotide(s) described herein, wherein the host cell secretes (and/or is capable of secreting) an increased level of C4-dicarboxylic acid compared to the host cell without the one or more (several) polynucleotide(s) when cultivated under the same conditions. In some aspects, the host cell secretes and/or is capable of secreting an increased level of C4-dicarboxylic acid (e.g., malic acid) of at least 5%, e.g., at least 10%, at least 15%, at least 20%, at least 25%, at least 50%, at least 100%, at least 150%, at least 200%, at least 300%, or at least 500% compared to the host cell without the one or more (several) polynucleotide(s) (e.g., without the heterologous polynucleotide encoding a bicarbonate transporter), when cultivated under the same conditions.

In any of the aspects of the recombinant host cells and methods described herein, the C4-dicarboxylic acid may be malic acid, succinic acid, oxaloacetic acid, malonic acid, or fumaric acid, or combinations thereof. In some aspects, the C4-dicarboxylic acid is malic acid, succinic acid, or fumaric acid, or combinations thereof. In some aspects, the C4-dicarboxylic acid is malic acid or fumaric acid, or a combination of malic acid and fumaric acid. In some aspects, the C4-dicarboxylic acid is malic acid.

In any of these aspects, the host cell produces (and/or is capable of producing) a C4-dicarboxylic acid at a yield of at least than 10%, e.g., at least than 20%, at least than 30%, at least than 40%, at least than 50%, at least than 60%, at least than 70%, at least than 80%, or at least than 90%, of theoretical.

In any of these aspects, the recombinant host has an C4-dicarboxylic acid volumetric productivity (e.g., malic acid volumetric productivity) greater than about 0.1 g/L per hour, e.g., greater than about 0.2 g/L per hour, 0.5 g/L per hour, 0.6 g/L per hour, 0.7 g/L per hour, 0.8 g/L per hour, 0.9 g/L per hour, 1.0 g/L per hour, 1.1 g/L per hour, 1.2 g/L per hour, 1.3 g/L per hour, 1.5 g/L per hour, 1.75 g/L per hour, 2.0 g/L per hour, 2.25 g/L per hour, 2.5 g/L per hour, or 3.0 g/L per hour; or between about 0.1 g/L per hour and about 2.0 g/L per hour, e.g., between about 0.3 g/L per hour and about 1.7 g/L per hour, about 0.5 g/L per hour and about 1.5 g/L per hour, about 0.7 g/L per hour and about 1.3 g/L per hour, about 0.8 g/L per hour and about 1.2 g/L per hour, or about 0.9 g/L per hour and about 1.1 g/L per hour.

The recombinant host cells may be cultivated in a nutrient medium suitable for production of the bicarbonate transporter, C4-dicarboxylic acid transporter, malate dehydrogenase, or pyruvate carboxylase using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the desired polypeptide to be expressed and/or isolated. The cultivation takes place in a suitable nutrient medium comprising carbon and nitrogen sources and inorganic salts, using procedures known in the art. Suitable media are available from commercial suppliers, may be prepared according to published compositions (e.g., in catalogues of the American Type Culture Collection), or may be prepared from commercially available ingredients.

The bicarbonate transporter, C4-dicarboxylic acid transporter, malate dehydrogenase, and pyruvate carboxylase, and activities thereof, can be detected using methods known in the art. These detection methods may include use of specific antibodies, formation of an enzyme product, or disappearance of an enzyme substrate. See, for example, Sambrook et al., *Molecular Cloning: A Laboratory Manual*, Third Ed., Cold Spring Harbor Laboratory, New York (2001); Ausubel et al., *Current Protocols in Molecular Biology*, John Wiley and Sons, Baltimore, Md. (1999); and Hanai et al., *Appl. Environ. Microbiol.* 73:7814-7818 (2007)).

Methods

The present invention also relates to methods of using the recombinant host cells described herein for the production of a C4-dicarboxylic acid. In one aspect, the invention embraces a method of producing a C4-dicarboxylic acid (e.g., malic acid), comprising: (a) cultivating any one of the recombinant host cells described herein (e.g., any host cell with bicarbonate transporter activity, and optionally, C4-dicarboxylic acid transporter activity, malate dehydrogenase activity, and/or pyruvate carboxylase activity) in a medium under suitable conditions to produce the C4-dicarboxylic acid; and (b) recovering the C4-dicarboxylic acid. In one aspect, the invention embraces a method of producing a C4-dicarboxylic acid (e.g., malic acid), comprising: (a) cultivating in a medium any one of the recombinant host cells described herein, wherein the host cell comprises a heterologous polynucleotide encoding a bicarbonate transporter; and optionally, a heterologous polynucleotide encoding a C4-dicarboxylic acid transporter, a heterologous polynucleotide encoding a malate dehydrogenase, and/or a heterologous polynucleotide encoding a pyruvate decarboxylase under suitable conditions to produce the C4-dicarboxylic acid; and (b) recovering the C4-dicarboxylic acid. In one aspect, the medium is a fermentable medium.

In one aspect of the methods, the C4-dicarboxylic acid (e.g., malic acid) is produced at a titer greater than about 10 g/L, e.g., greater than about 25 g/L, 50 g/L, 75 g/L, 100 g/L, 125 g/L, 150 g/L, 160 g/L, 170 g/L, 180 g/L, 190 g/L, 200 g/L, 210 g/L, 225 g/L, 250 g/L, 275 g/L, 300 g/L, 325 g/L, 350 g/L, 400 g/L, or 500 g/L; or between about 10 g/L and about 500 g/L, e.g., between about 50 g/L and about 350 g/L, about 100 g/L and about 300 g/L, about 150 g/L and about 250 g/L, about 175 g/L and about 225 g/L, or about 190 g/L and about 210 g/L.

In one aspect of the methods, the amount of produced C4-dicarboxylic acid (e.g., malic acid) is at least 5%, e.g., at least 10%, at least 15%, at least 20%, at least 25%, at least 30%, at least 50%, or at least 100% greater compared to cultivating the host cell without the polynucleotide that encodes the bicarbonate transporter under the same conditions.

In some aspects of the methods, the C4-dicarboxylic acid is selected from malic acid, succinic acid, oxaloacetic acid, malonic acid, and fumaric acid. In one aspect, the C4-dicarboxylic acid is malic acid.

The recombinant C4-dicarboxylic acid can be optionally recovered from the fermentation medium using any procedure known in the art (see, for example, WO 1998/022611 and U.S. Pat. No. 7,601,865) including, but not limited to, chromatography (e.g., size exclusion chromatography, adsorption chromatography, ion exchange chromatography), electrophoretic procedures, differential solubility, osmosis, distillation, extraction (e.g., liquid-liquid extraction), pervaporation, extractive filtration, membrane filtration, membrane separation, reverse, or ultrafiltration. In one example, the C4-dicarboxylic acid is recovered from other material in the fermentation medium by filtration.

In some aspects of the methods, the recombinant C4-dicarboxylic acid before and/or after being optionally purified is substantially pure. With respect to the methods of producing a C4-dicarboxylic acid (or a specific C4-dicarboxylic acid thereof, such as malic acid), "substantially pure" intends a recovered preparation of the C4-dicarboxylic acid that contains no more than 15% impurity, wherein impurity intends compounds other than C4-dicarboxylic acids. In one variation, a preparation of substantially pure C4-dicarboxylic acid is provided wherein the preparation contains no more than 25% impurity, or no more than 20% impurity, or no more than 10% impurity, or no more than 5% impurity, or no more than 3% impurity, or no more than 1% impurity, or no more than 0.5% impurity.

Suitable assays to test for the production of C4-dicarboxylic acids for the methods of production and host cells described herein can be performed using methods known in the art. For example, the final C4-dicarboxylic acid product (e.g., malic acid), and other organic compounds, can be analyzed by methods such as HPLC (High Performance Liquid Chromatography), GC-MS (Gas Chromatography Mass Spectroscopy) and LC-MS (Liquid Chromatography-Mass Spectroscopy) or other suitable analytical methods using routine procedures well known in the art. The release of C4-dicarboxylic acid in the fermentation broth can also be tested with the culture supernatant. Byproducts and residual sugar in the fermentation medium (e.g., glucose) can be quantified by HPLC using, for example, a refractive index detector for glucose and alcohols, and a UV detector for organic acids (Lin et al., *Biotechnol. Bioeng.* 90:775-779 (2005)), or using other suitable assay and detection methods well known in the art.

The present invention is further described by the following examples that should not be construed as limiting the scope of the invention.

EXAMPLES

Chemicals used as buffers and substrates were commercial products of at least reagent grade.

Fungal Strains

*Aspergillus oryzae* NRRL 3488 (or ATCC 56747) was used as a source of a bicarbonate transporter gene (bt1), a pyruvate carboxylase gene (pyc), a malate dehydrogenase gene (mdh3), and for production of the C4-dicarboxylic acids. *Aspergillus aculeatus* was used as a source of a C4-dicarboxylic acid transport protein gene (c4t521).

Media

YEG medium was composed of 20 g glucose, 5 g yeast extract, and deionized water to 1 liter.

COVE plates were composed of 1 M sucrose, 2% COVE salt solution, 10 mM acetamide, 15 mM CsCl, and 25 g/l Agar Noble.

COVE salt solution was composed of 26 g KCl, 26 g $MgSO_4.7H_2O$, 76 g $KH_2PO_4$, 50 ml of COVE trace elements solution, and deionized water to 1 liter.

COVE trace elements solution was composed of 0.04 g $Na_2B_4O_7.10H_2O$, 0.04 g $CuSO_4.5H_2O$, 1.2 g $FeSO_4.7H_2O$, 0.7 g $MnSO_4.H_2O$, 0.8 g $Na_2MoO_2.2H_2O$, 10 g $ZnSO_4.7H_2O$ and deionized water to 1 liter.

Seed medium was composed of 40 g glucose, 6 g Bacto-peptone, 750 mg $KH_2PO_4$, 750 mg $K_2HPO_4$, 100 mg $MgSO_4.7H_2O$, 100 mg $CaCl_2.H_2O$, 5 mg $FeSO_4.7H_2O$, 5 mg NaCl, and deionized water to 1 liter.

Seed medium B was composed of 30 g glucose, 3 g Bacto-peptone, 560 mg $KH_2PO_4$, 560 mg $K_2HPO_4$, 925 mg $NaH_2PO_4.H_2O$, 820 mg $Na_2HPO_4$, 75 mg $MgSO_4.7H_2O$, 75 mg $CaCl_2.H_2O$, 0.75 ml of 1000× Micronutrient Solution, and deionized water to 1 liter.

Acid production medium C was composed of 100 g glucose, 80 g $CaCO_3$, 6 g Bacto Peptone, 150 mg $KH_2PO_4$, 150 mg $K_2HPO_4$, 100 mg $MgSO_4.7H_2O$, 100 mg $CaCl_2.H_2O$, 1 ml 1000× Micronutrient Solution, and deionized water to 1 liter.

Fermentor batch medium was composed of 60 g glucose, 120 g $CaCO_3$, 9 g Bacto-peptone, 150 mg $KH_2PO_4$, 150 mg $K_2HPO_4$, 100 mg $MgSO.7H_2O$, 100 mg $CaCl_2-2H_2O$, 5 mg $FeSO_4.7H_2O$, 5 mg NaCl, 5 mL Pluronic L61, and deionized water to 1 liter.

1000× Micronutrient Solution was composed of 5 g NaCl, 5 g $FeSO_47H_2O$, 1 g citric acid, and deionized water to 1 liter.

PDA plates were composed of 39 g/l potato dextrose agar. 2XYT+amp plates were composed of 16 g tryptone, 10 g yeast extract, 5 g NaCl, 100 mg ampicillin, 15 g Bacto agar, and deionized water to 1 liter.

Example 1

Cloning of an *Aspergillus oryzae* Bicarbonate Transporter Gene (bt1) and Construction of Expression Vector pAmFs69

The bicarbonate transporter gene bt1 (A0090012000782) was cloned from *Aspergillus oryzae* NRRL3488 genomic DNA by PCR amplification using primers homologous to the *Aspergillus oryzae* predicted bicarbonate transporter gene model number A0090012000782 found in the published *A. oryzae* ATCC 42149 genome sequence (Galagan et al., 2005, Nature 438: 1105-1115).

Genomic DNA from *A. oryzae* NRRL3488 was isolated by inoculating 100 ml YEG medium in a shake flask with 2×10⁶ spores and incubating the flask at 37° C. overnight with shaking at 200 rpm. The mycelia were harvested in MIRACLOTH® (Calbiochem, San Diego, Calif., USA) lined funnel and approximately 2 grams of tissue was frozen in liquid nitrogen. The mycelia were disrupted by grinding in a cold mortar and pestle. Genomic DNA was isolated from the powdered mycelia using a DNeasy® Plant Maxi Kit (QIAGEN Inc., Valencia, Calif., USA) according to the manufacturer's instructions. The *Aspergillus oryzae* bt1 gene was amplified using forward primer 069824 and reverse primer 069825 shown below:

```
Primer 069824:
                                    (SEQ ID NO: 11)
5'-GTGATAGAACATCGTCCATAATGGAATCCAGCGCTGTACA-3'

Primer 069825:
                                    (SEQ ID NO: 12)
5'-GTGTCAGTCACCTCTAGTTATCAGATTTCAATCTCGTCTT-3'
```

The amplification reactions were performed using Phusion® Hot Start High-Fidelity DNA Polymerase (Finnzymes OY, Finland) according to manufacturer's instructions. Each PCR reaction contained 47 ng of *Aspergillus oryzae* NRRL3488 genomic DNA, 200 µM dNTPs, 50 pM of forward primer, 50 pM reverse primer, 1× Phusion® GC Buffer reaction buffer (Finnzymes OY, Finland), and 50 units of Phusion® Hot Start High-Fidelity DNA Polymerase in a final volume of 50 µl. The amplification reactions were incubated in an EPPENDORF®MASTERCYCLER® (Eppendorf Scientific Inc., Westbury, N.Y., USA) programmed for 1 cycle at 98° C. for 30 seconds; 35 cycles at 98° C. for 10 seconds, 66° C. for 30 seconds, and 72° C. for 2.5 minutes; and 1 cycle at 72° C. for 10 minutes. The PCR product was purified by 1% agarose gel electrophoresis in 50 mM Tris base-50 mM acetate-0.1 mM disodium EDTA (TAE) buffer. A fragment of approximately 2.5 kb was excised from the gel and extracted from the agarose using a QIAQUICK® Gel Extraction Kit (QIAGEN Inc., Valencia, Calif., USA).

Figure 2:
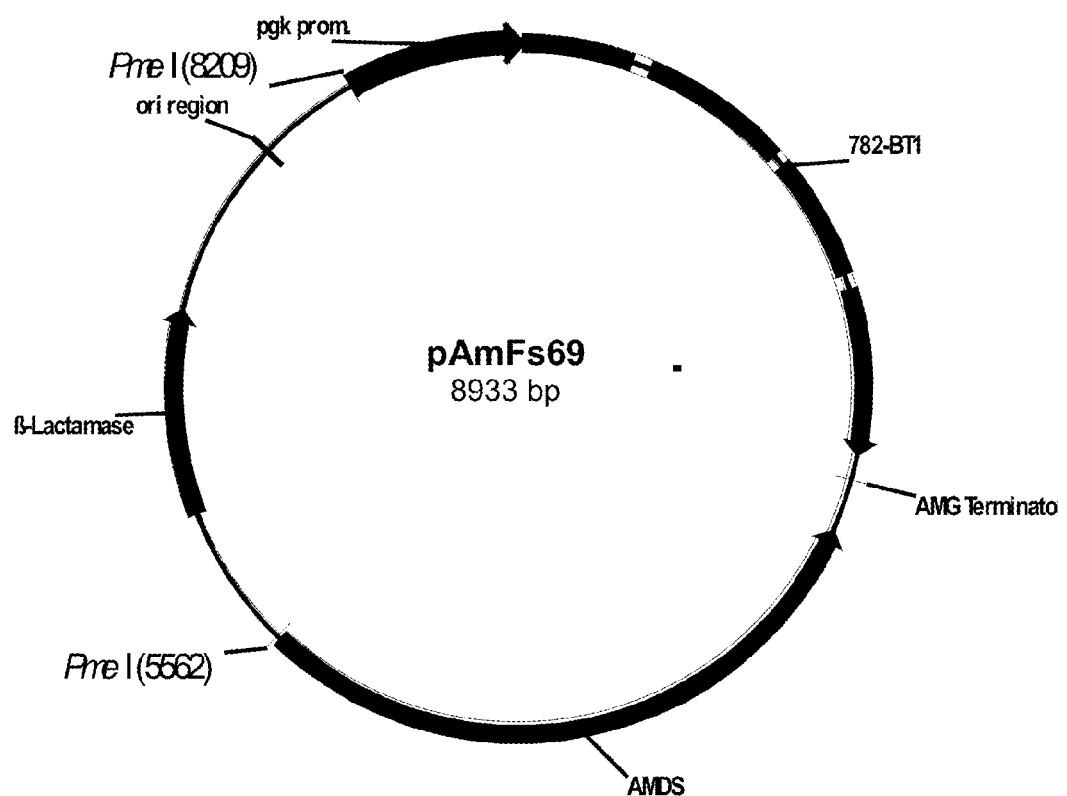
FIG. 2 shows a restriction map of pAmFs69.

Plasmid pShTh60 (FIG. 1; see also PCT Application No. PCT/US10/47002, filed Aug. 27, 2010) was digested with Sex AI and Pac I, separated by 0.8% agarose gel electrophoresis in TBE buffer (10.8 g/L Tris Base, 5.5 g/L Boric acid, 2 mM EDTA, pH 8.0) and purified using a QIAQUICK® Gel Extraction Kit (QIAGEN Inc., Valencia, Calif., USA). The purified PCR product above was then inserted into the digested pShTh60 fragment using an In-Fusion™ Advantage reaction kit (Clontech, Mountain View, Calif., USA) according to the manufacturer's instructions resulting in plasmid pAmFs69 (FIG. 2).

A 2.5 µl aliquot of the ligation reaction above was transformed into ONE SHOT® TOP10 chemically competent *E. coli* cells according to the manufacturer's instructions. Transformants were plated onto 2XYT+amp plates and incubated at 37° C. overnight.

DNA sequence analysis was used on the resulting transformants to confirm the integrity of the bt1 coding sequence. Primers 610849, 610851, 610853, 610855, 610857, 610859, and 610861 shown below were used with an ABI3130XL DNA Analyzer (Applied Biosystems, Inc., Foster City, Calif., USA) and the primer walking technique with dye-terminator chemistry (Giesecke et al., 1992, *J. Virol. Methods* 38: 47-60).

```
                                    (SEQ ID NO: 13)
Primer 610849: 5'-GAACAGGAAGAAATCCAAAA-3'

(SEQ ID NO: 14)
Primer 610851: 5'-GTCGGCATAGCCACTGCAAT-3'

(SEQ ID NO: 15)
Primer 610853: 5'-TGTTGCCGCCAAGGGACTTA-3'

(SEQ ID NO: 16)
Primer 610855: 5'-CCGAGAGCGTTGAGTTAATC-3'

(SEQ ID NO: 17)
Primer 610857: 5'-AGCATTAGGGCTAGCTCCGT-3'

(SEQ ID NO: 18)
Primer 610859: 5'-CCAAGATGCCATGTCAGGAC-3'

(SEQ ID NO: 19)
Primer 610861: 5'-TCACAAAAGAGTAGAGGCCA-3'
```

The nucleotide construct of the genomic DNA sequence (SEQ ID NO: 1), and deduced amino acid sequence (SEQ ID NO: 2) of the *Aspergillus oryzae* bt1 gene are shown in FIGS. 3A and 3B. The genomic coding sequence of 2503 bp (including one stop codon) is interrupted by three introns of 78 bp (465-542), 51 bp (1173-1223), and 61 bp (1747-1807). The corresponding cDNA sequence (bold nucleotide sequence shown in FIGS. 3A and 3B) is 2313 bp, including one stop codon. The predicted encoded protein is 770 amino acids, with a predicted molecular mass of 83.9 kDa and an isoelectric pH of 6.9.

Example 2

Cloning of an *Aspergillus oryzae* Bicarbonate Transporter Gene AO090003000798 and Construction of Corresponding Expression Vector The bicarbonate transporter gene bt2 (AO090003000798) was cloned from *Aspergillus oryzae* NRRL3488 genomic DNA by PCR amplification using primers homologous to the *Aspergillus oryzae* predicted bicarbonate transporter gene model number AO090003000798 found in the published *A. oryzae* ATCC 42149 genome sequence (Galagan et al., 2005, supra).

Genomic DNA from *A. oryzae* NRRL3488 was isolated and the mycelia were harvested and processed as described in Example 1. The *Aspergillus oryzae* bt2 gene was amplified using forward primer 0614058 and reverse primer 0614057 shown below:

```
Primer 0614058:
                                          (SEQ ID NO: 52)
5'-GTGATAGAACATCGTCCATAATGCCGGGCGATCTCAAAACC-3'

Primer 0614057:
                                          (SEQ ID NO: 53)
5'-GTGTCAGTCACCTCTAGTTACTATGCATCAAGGACATTC-3'
```

The amplification reactions were performed using Phusion® Hot Start High-Fidelity DNA Polymerase (Finnzymes) according to manufacturer's instructions. Each PCR reaction contained 47 ng of *Aspergillus oryzae* NRRL3488 genomic DNA, 200 μM dNTPs, 50 pM of forward primer, 50 pM reverse primer, 1× Phusion® GC Buffer reaction buffer (Finnzymes), and 50 units of Phusion® Hot Start High-Fidelity DNA Polymerase in a final volume of 50 μl. The amplification reactions were incubated in an EPPENDORF® MASTERCYCLER® (Eppendorf Scientific Inc.) programmed for 1 cycle at 98° C. for 2 minutes; 35 cycles at 98° C. for 15 seconds, 65° C. for 15 seconds, and 74° C. for 1 minute; and 1 cycle at 74° C. for 1 minute. The PCR product was purified by 1% agarose gel electrophoresis in 50 mM Tris base-50 mM acetate-0.1 mM disodium EDTA (TAE) buffer. A fragment of approximately 2.7 kb was excised from the gel and extracted from the agarose using a QIAQUICK® Gel Extraction Kit (QIAGEN Inc.).

Figure 11:
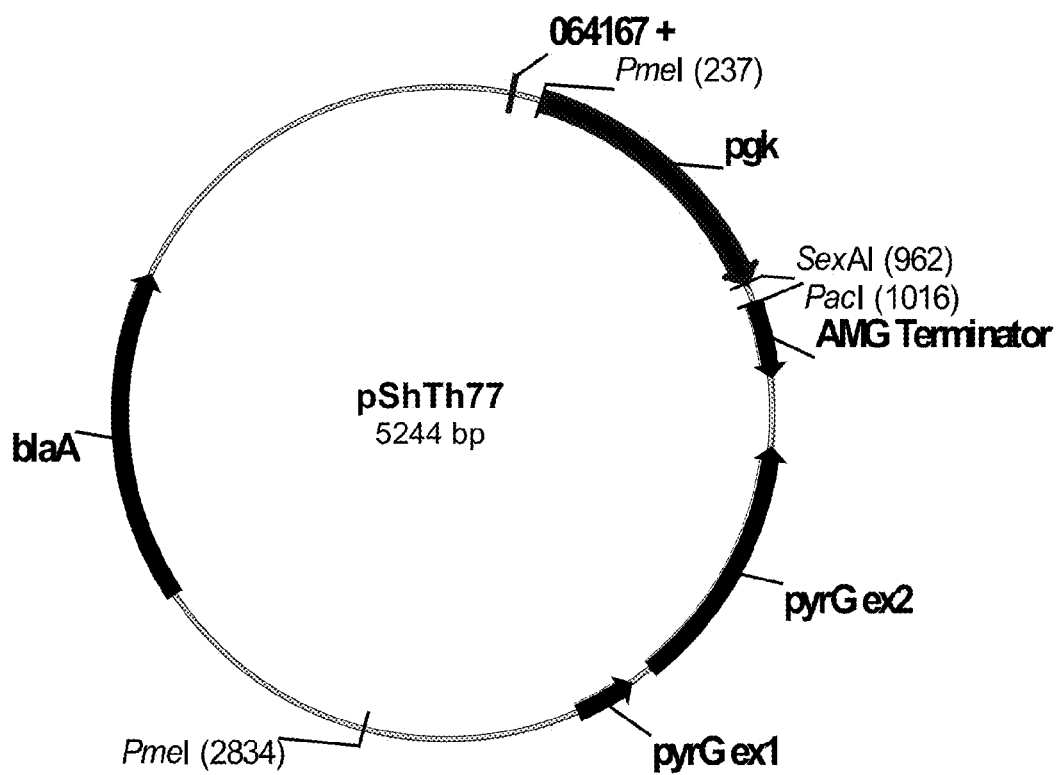
FIG. 11 shows a restriction map of pShTh77.
Figure 12:
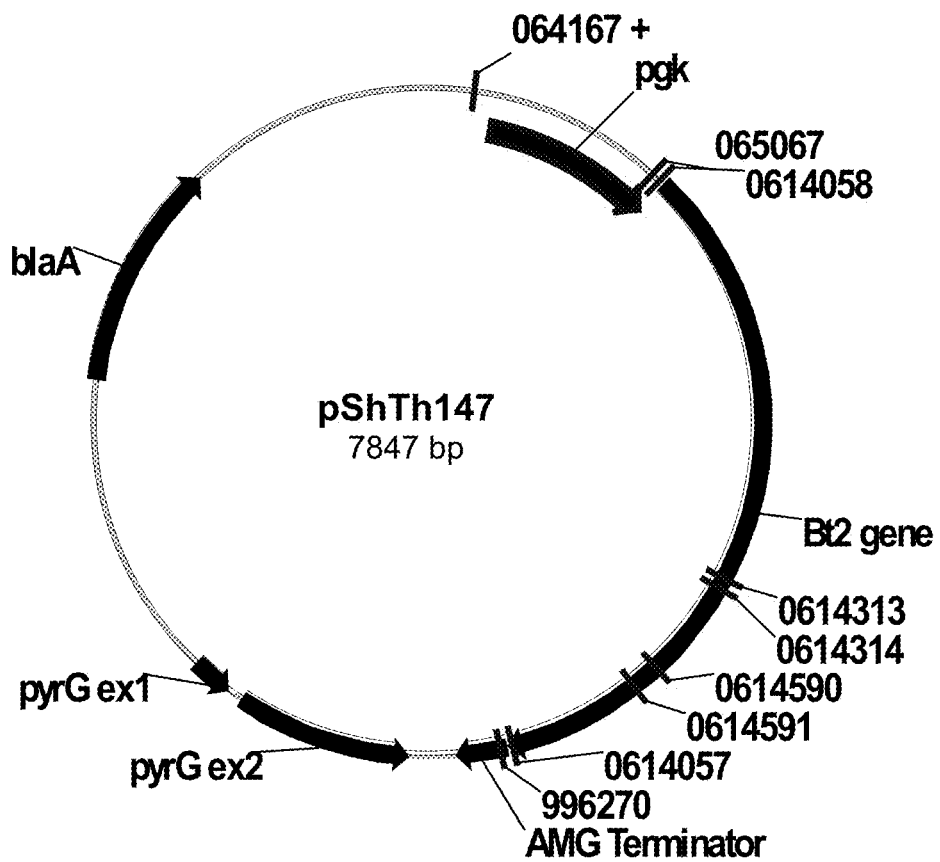
FIG. 12 shows a restriction map of pShTh147.

Plasmid pShTh77 (FIG. 11) was digested with Sex AI and Pac I, separated by 0.8% agarose gel electrophoresis in TBE buffer (10.8 g/L Tris Base, 5.5 g/L Boric acid, 2 mM EDTA, pH 8.0) and purified using a QIAQUICK® Gel Extraction Kit (QIAGEN Inc., Valencia, Calif., USA). The purified PCR product above was then inserted into the digested pShTh77 fragment using an In-Fusion™ Advantage reaction kit (Clontech) according to the manufacturer's instructions resulting in plasmid pShTh147 (FIG. 12).

A 2.5 μl aliquot of the ligation reaction above was transformed into ONE SHOT® TOP10 chemically competent *E. coli* cells according to the manufacturer's instructions. Transformants were plated onto 2XYT+amp plates and incubated at 37° C. overnight.

DNA sequence analysis was used on the resulting transformants to confirm the integrity of the bt2 coding sequence. Primers 0614313, 0614314, 996270, and 0611428, shown below were used with an ABI3130XL DNA Analyzer (Applied Biosystems, Inc., Foster City, Calif., USA) and the primer walking technique with dye-terminator chemistry (Giesecke et al., 1992, *J. Virol. Methods* 38: 47-60).

```
                                           (SEQ ID NO: 54)
    Primer 0614313:  5'-GATTGAGATCGGCATTTACT-3'

(SEQ ID NO: 55)
    Primer 0614314:  5'-ACGCGGAACAGCAGAATGGC-3'

(SEQ ID NO: 56)
    Primer 996270:   5'-CTATAGCGAAATGGATTGATTGTCT-3'

(SEQ ID NO: 57)
    Primer 0611428:  5'-TTCACCGTGAAACGTATTGA-3'
```

The nucleotide construct of the genomic DNA sequence (SEQ ID NO: 3), and deduced amino acid sequence (SEQ ID NO: 4) of the *Aspergillus oryzae* bt1 gene are shown in FIGS. 4A and 4B. The genomic coding sequence of 2657 bp (including stop codon) is interrupted by two introns of 64 bp (302-365) and 61 bp (512-572). The corresponding cDNA sequence (bold nucleotide sequence shown in FIGS. 4A and 4B) is 2532 bp, including one stop codon. The predicted encoded protein is 843 amino acids, with a predicted molecular mass of 92.5 kDa and an isoelectric pH of 8.4.

Example 3

Cloning of an *Aspergillus aculeatus* C4-Dicarboxylic Acid Transporter Gene and Construction of Expression Vector pSaMF36

Genomic DNA from *Aspergillus aculeatus* was isolated by inoculating 100 ml of YEG medium in a shake flask with 2×10⁶ spores and incubating the flask at 34° C. overnight with shaking at 160 rpm. The mycelia were harvested by filtration using a MIRACLOTH® (Calbiochem, San Diego, Calif., USA) lined funnel and approximately 2 g of mycelia were recovered and frozen in liquid nitrogen. The frozen mycelia were disrupted by quickly smashing with a hammer while wrapped inside the MIRACLOTH®. The disrupted mycelia were then transferred to a 50 ml polypropylene conical centrifuge tube containing 10 ml of 1× lysis buffer (100 mM EDTA, 10 mM Tris pH 8.0, 1% Triton® X-100, 0.5 M Guanidine-HCl, 200 mM NaCl) and 3 μl of RNase A (QIAGEN Inc., Valencia, Calif., USA, 100 mg/ml). The tube was mixed by gentle vortexing, and then incubated at room temperature for 5 minutes after which was added 150 μl Proteinase K (QIAGEN Inc., Valencia, Calif., USA; 20 mg/ml). The tube was mixed by inversion and incubated at 50° C. for 1 hour. The tube was then centrifuged at 7240×g for 20 minutes. The supernatant was then added to a pre-equilibrated QIAGEN-tip 100 (QIAGEN Inc., Valencia, Calif., USA) and the remaining DNA extraction steps were performed according to the manufacturer's instructions. The DNA was resuspended in 100 μl TE buffer (10 mM Tris Base, 1 mM EDTA, pH 8.0).

The 1257 bp C4-dicarboxylic acid transporter gene c4t521 was amplified from isolated *Aspergillus aculeatus* genomic DNA using primers 069700 and 069701 shown below.

```
    Primer 069700:
                                           (SEQ ID NO: 20)
    5'-TGTGATAGAACATCGTCCATAATGCACGACCACAGC-3'

Primer 069701:
                                           (SEQ ID NO: 21)
    5'-GTGTCAGTCACCTCTAGTTATCATTCGAACAACTCGGACA-3'
```

The PCR reaction was composed of 10 μl 5× reaction buffer, 1 μl *A. aculeatus* genomic DNA template (105 ng/μl), 1 μl primer 069700 (100 ng/μl), 1 μl primer 069701 (100 ng/μl), 1 μl dNTP mixture (10 mM), 35.5 μl deionized water, and 0.5 μl Phusion™ Hot Start High-Fidelity DNA polymerase (Finnzymes, Inc, Massachusetts, USA). The amplification reaction was incubated in an EPPENDORF® MASTERCYCLER® programmed for 1 cycle at 98° C. for 30 seconds; 30 cycles each at 98° C. for 10 seconds, 60° C. for 30 seconds, 72° C. for 1 minute; and one cycle at 72° C. for 10 minutes. The PCR product was digested with Dpn I for 1 hour to degrade any plasmid DNA template.

Figure 5:
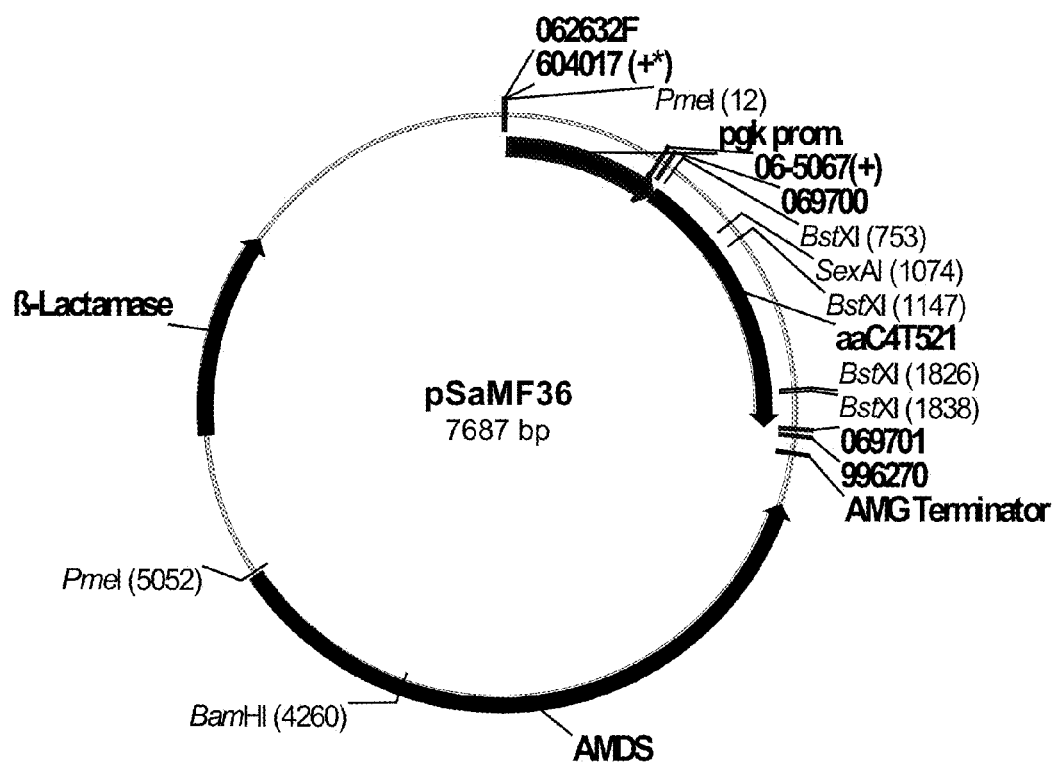
FIG. 5 shows a restriction map of pSaMF36.

Plasmid pShTh60 (FIG. 1) was digested with Sex AI and Pac I, separated by 0.8% agarose gel electrophoresis in TBE buffer, and purified using a QIAQUICK® Gel Extraction Kit. The purified PCR product above was then inserted into the digested pShTh60 fragment using an In-Fusion™ Advantage reaction kit composed of 2 μl 5× buffer, 3 μl purified PCR product (26 ng/μl), 1.5 μl gel-purified Sex AI and Pac I digested and gel-purified pShTh60 (132 ng/μl), 1

µl In-Fusion™ enzyme and 2.5 µl deionized water. The reaction was incubated at 37° C. for 15 minutes, 50° C. for 15 minutes, placed on ice for 5 minutes and diluted with 40 µl TE buffer resulting in pSaMF36 (FIG. 5).

A 2.5 µl aliquot of the ligation reaction above was transformed into ONE SHOT® TOP10 chemically competent E. coli cells according to the manufacturer's instructions. Transformants were plated onto 2XYT+amp plates and incubated at 37° C. overnight. The resulting transformants were picked and subjected to DNA sequencing to confirm that the mat521 gene was successfully integrated into the vector.

The nucleotide construct of the genomic DNA sequence (SEQ ID NO: 5) and deduced amino acid sequence (SEQ ID NO: 6) of the Aspergillus aculeatus c4t521 gene are shown in FIG. 6. The genomic coding sequence of 1257 bp (including stop codon) contains no introns. The predicted encoded protein is 418 amino acids, with a predicted molecular mass of 46.8 kDa and an isoelectric pH of 6.36. Using the SignalP program (Nielsen et al., 1997, Protein Engineering 10:1-6), a signal peptide of 17 residues was predicted. Based on this program, the predicted mature protein contains 401 amino acids with a predicted molecular mass of 44.9 kDa and an isoelectric pH of 6.89.

Example 4

Cloning of an Aspergillus oryzae Malate Dehydrogenase Gene and Construction of Expression Vector pSaMF21

Plasmid pSaMF21 was constructed to contain the NAD-dependent malate dehydrogenase (mdh3) gene sequence (DOGAN: AO090701000013), a 1430 bp fragment from Aspergillus oryzae as described in PCT Application No. PCT/US10/47002, filed Aug. 27, 2010. The nucleotide construct of the genomic DNA sequence (SEQ ID NO: 7) and deduced amino acid sequence (SEQ ID NO: 8) of the Aspergillus oryzae NRRL 3488 malate dehydrogenase mdh3 gene are shown in FIG. 7. The genomic coding sequence of 1430 bp (including stop codon) is interrupted by 7 introns of 57 bp (14-70 bp), 70 bp (103-172 bp), 74 bp (284-357 bp), 68 bp (446-513 bp), 58 bp (892-949 bp), 48 bp (1035-1082 bp), and 62 bp (1228-1289 bp). The G+C content of the coding region of the mdh3 gene is 50.3%. The corresponding cDNA sequence (bold nucleotide sequence shown in FIG. 7) is 993 bp, including one stop codon. The predicted encoded protein is 330 amino acids with a predicted mass of 34.5 kDa and an isoelectric pH of 6.79.

Briefly, the plasmid was constructed by linearizing pShTh60 (FIG. 1) by restriction digestion with Sex AI and Pac I. The digested vector was separated by 0.8% agarose gel electrophoresis in TBE buffer and purified using a QIAQUICK® Gel Extraction Kit. The mdh3 gene was amplified from pShTh71 (PCT Application No. PCT/US10/47002, filed Aug. 27, 2010) using primers 067522 and 067525.

```
Primer 067522:
                                     (SEQ ID NO: 22)
5'-AGAACATCGTCCATAATGGTCAAAGCTGGTGAGTTA-3'

Primer 067525:
                                     (SEQ ID NO: 23)
5'-GTGTCAGTCACCTCTAGTTATTACTTTGGTGGTGGGTTCT-3'
```

Figure 8:
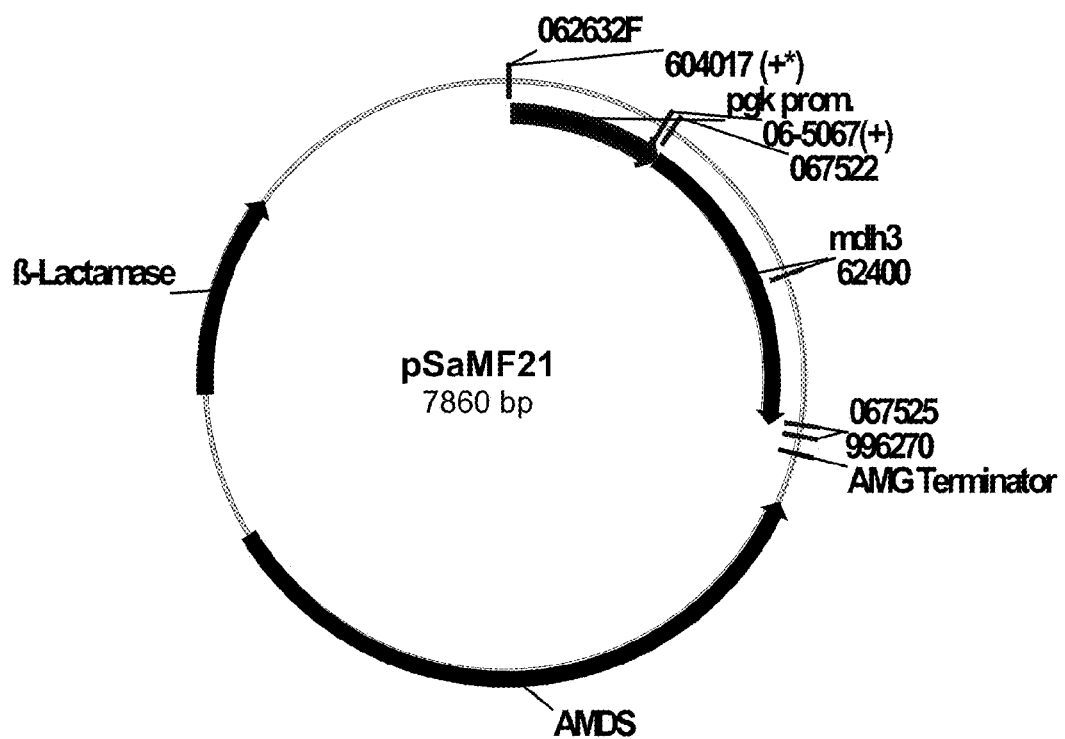
FIG. 8 shows a restriction map of pSaMF21.

The PCR reaction was composed of 5 µl 10× reaction buffer, 1 µl pShTh71 template (87 ng/µl), 1 µl primer 067522 (100 ng/µl), 1 µl primer 067525 (100 ng/µl), 1 µl dNTP mixture (10 mM), 45.5 µl deionized water, and 0.5 µl Herculase® HotStart DNA polymerase (Stratagene, La Jolla, Calif., USA). The amplification reaction was incubated in an EPPENDORF® MASTERCYCLER® programmed for 1 cycle at 95° C. for 2 minutes; 10 cycles each at 95° C. for 10 seconds, 58° C. for 30 seconds, and 72° C. for 1.5 minutes; 20 cycles each at 95° C. for 10 seconds, 50° C. for 30 seconds, and 72° C. for 1.5 minutes plus 10 seconds per cycle. The PCR reaction was subjected to a restriction digest with Dpn I for 1 hour to degrade any plasmid DNA template. The PCR product was then purified using the MinElute® PCR Purification Kit (QIAGEN Inc., Valencia, Calif., USA). The purified PCR product was inserted into the vector using an In-Fusion™ Advantage reaction composed of 2 µl 5× buffer, 0.5 µl purified PCR product (110 ng/µl), 1.7 µl gel-purified Sex AI and Pac I restriction digested pShTh60 (FIG. 1; 78 ng/µl), 1 µl In-Fusion™ enzyme and 4.8 µl deinonized water. The reaction was incubated at 37° C. for 15 minutes followed by 50° C. for 15 minutes after which it was placed on ice for 5 minutes and diluted with 40 µl TE buffer resulting in pSaMF21 (FIG. 8). A 2 µl aliquot of the ligation reaction was transformed into ONE SHOT® TOP10 chemically competent E. coli cells (Invitrogen, San Diego, Calif., USA) according to the manufacturer's instructions. Transformants were plated onto 2XYT+amp plates and incubated at 37° C. overnight. The resulting transformants were picked and subjected to DNA sequencing to confirm that the mdh3 gene was successfully integrated into the vector.

Example 5

Cloning of an Aspergillus oryzae Pyruvate Carboxylase Gene and Construction of Expression Vector pRyan1

Plasmid pRyan1 was constructed to contain the pyruvate carboxylase (pyc) gene sequence (DOGAN: AO090023000801), a 3646 bp fragment from Aspergillus oryzae (including two stop codons) as described in PCT Application No. PCT/US10/47002, filed Aug. 27, 2010. The nucleotide construct of the genomic DNA sequence (SEQ ID NO: 9) and deduced amino acid sequence (SEQ ID NO: 10) of the Aspergillus oryzae pyruvate carboxylase gene are shown in FIGS. 9A and 9B. Both the Aspergillus oryzae NRRL 3488 and ATCC 56747 pyruvate carboxylase genes have the same nucleotide sequence. The G+C content of the coding region of the gene is 57.1%. The genomic coding sequence of 3643 bp (including one stop codon) is interrupted by 1 intron of 61 bp (3475-3535 bp). The G+C content of the coding region of the gene is 57.1%. The corresponding cDNA sequence (bold nucleotide sequence shown in FIGS. 9A and 9B) is 3582 bp, including one stop codon. The predicted encoded protein is 1193 amino acids with a predicted mass of 131 kDa.

Briefly, the plasmid was constructed by linearizing pShTh60 (FIG. 1) by restriction digestion with Sex AI and Pac I. The digested vector was separated by 0.8% agarose gel electrophoresis in TBE buffer and purified using a QIAQUICK® Gel Extraction Kit. The pyc gene was amplified from *Aspergillus oryzae* NRRL 3488 genomic DNA using primers 066549 and 067388 shown below.

```
Primer 066549:
                                        (SEQ ID NO: 24)
5'-TAGAACATCGTCCATAATGGCGGCTCCGTTTCGTCA-3'

Primer 067388:
                                        (SEQ ID NO: 25)
5'-GTGTCAGTCACCTCTAGTTATTATTACGCTTTGACGATCT-3'
```

The PCR reaction was composed of 5 μl 10× reaction buffer, 1 μl *Aspergillus oryzae* NRRL3488 genomic DNA (110 ng/μl), 1 μl primer 066549 (100 ng/μl), 1 μl primer 067388 (100 ng/μl), 1 μl dNTP mixture (10 mM), 45.5 μl deionized water, and 0.5 μl Herculase® HotStart DNA polymerase. The amplification reaction was incubated in an EPPENDORF® MASTERCYCLER® programmed for 1 cycle at 95° C. for 2 minutes; 10 cycles each at 95° C. for 10 seconds, 58° C. for 30 seconds, and 72° C. for 3.5 minutes; 20 cycles each at 95° C. for 10 seconds, 58° C. for 30 seconds, and 72° C. for 3.5 minutes plus 10 seconds per cycle. The PCR product was then purified using a MinElute® PCR Purification Kit.

Figure 10:
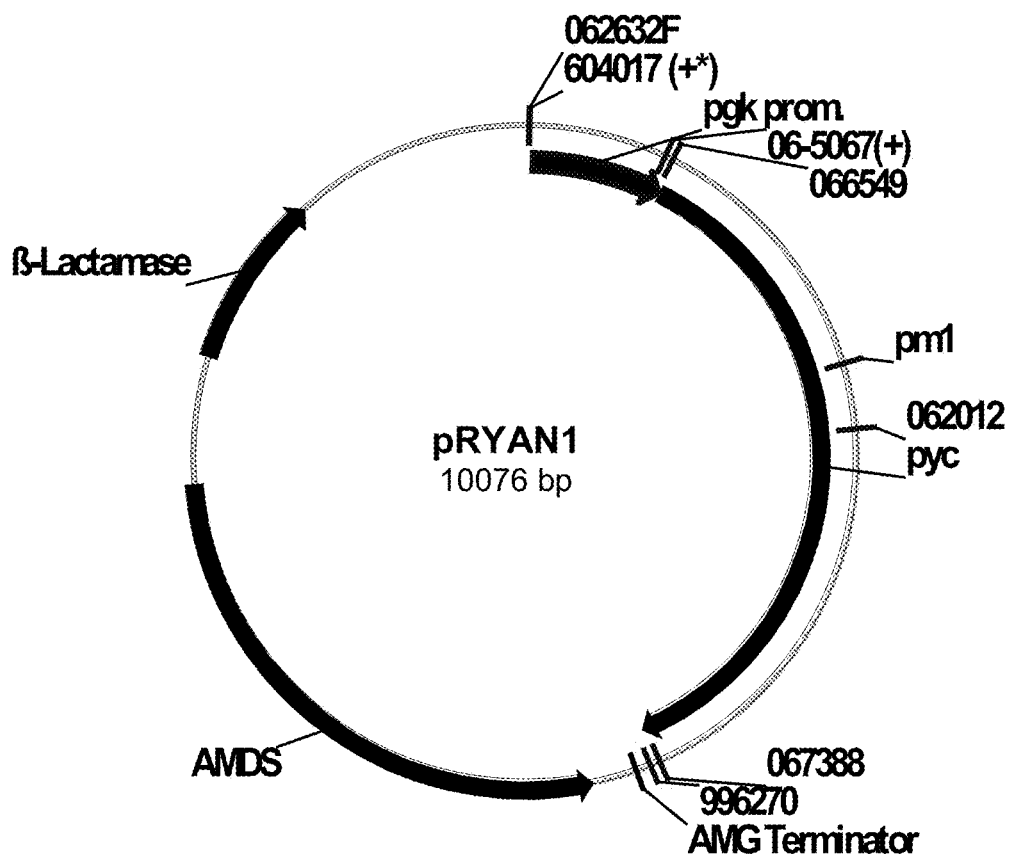
FIG. 10 shows a restriction map of pRYAN1.

The purified PCR product was inserted into the vector using an In-Fusion™ Advantage reaction composed of 2 μl 5× buffer, 1 μl purified PCR product (144 ng/μl), 2 μl gel purified Sex AI and Pac I restriction digested pShTh60 (FIG. 1; 78 ng/μl), 1 μl In-Fusion™ enzyme and 4 μl deionized water. The reaction was incubated at 37° C. for 15 minutes followed by 50° C. for 15 minutes after which it was placed on ice for 5 minutes and diluted with 40 μl TE buffer resulting in pRYAN1 (FIG. 10). A 2 μl aliquot of the ligation reaction was transformed into ONE SHOT® TOP10 chemically competent *E. coli* cells according to the manufacturer's instructions. Transformants were plated onto 2XYT+amp plates and incubated at 37° C. overnight. The resulting transformants were picked and subjected to DNA sequencing to confirm that the pyc gene was successfully integrated into the vector. Nucleotide 1308 was changed from C to T, but did not affect the protein sequence.

Example 6

Transformation of Expression Vector Fragments of pAmFs69, pRyan1, pSaMf21, pSaMf36 into *Aspergillus oryzae* NRRL3488 (ShTh6900)

Protoplast preparation and transformation of *Aspergillus oryzae* NRRL3488 were performed by inoculating approximately $2 \times 10^7$ spores into 100 ml YEG medium and incubating the flask at 27° C. for 16-18 hours at 140 rpm. Mycelia were collected by pouring the culture through a sterile funnel lined with MIRACLOTH® and rinsing with 50 ml of 0.7 M KCl. The washed mycelia were resuspended in a 125 ml flask with 20 ml of protoplasting solution composed of 5 mg of GLUCANEX™ (Novozymes NS, Bagsværd, Denmark) and 0.5 mg of chitinase (Sigma, USA) per ml of 0.7 M KCl (filter sterilized) and incubated at 34° C., for 30 minutes with mixing at 80 rpm. The protoplasting solution was poured through a sterile funnel lined with MIRACLOTH® and rinsed with 50 ml of STC composed of 1 M sorbitol-10 mM Tris-HCl pH 6.5-10 mM $CaCl_2$. The flow-through was collected in two 50 ml polypropylene tubes. The tubes were spun in the centrifuge at 1300×g for 10 minutes at room temperature. The supernatant was discarded and the protoplast pellet was resuspended in 20 ml of STC buffer. The protoplasts were washed by two rounds pellet resuspension in 20 ml of STC buffer and centrifugation at 1300×g for 10 minutes at room temperature. The final pellet was resuspended in 2 ml of STC buffer. The protoplasts were counted by removing a 10 μl sample and counting them in a haemocytometer (VWR, West Chester, Pa., USA). The volume was adjusted with STC buffer to obtain a protoplast concentration of $2 \times 10^7$ per ml.

The plasmid expression vectors pAmFs69 (Example 1), pSaMF36 (Example 3), pSaMF21 (Example 4) and pRyan1 (Example 5) were individually prepared for transformation by restriction digestion with Pme I for 4 hours at 37° C. The approximately 5-6 kb expression cassettes from each construct were separated from the vector sequences by 0.8% agarose gel electrophoresis in TBE buffer, and purified using a QIAQUICK® Gel Extraction Kit according to manufacturer's instructions.

Four transformation reactions were prepared by adding 100 μl of protoplast preparation above into four 12 ml polypropylene tubes. To each tube was added two micrograms of the digested pRyan1 pyc fragment, and one microgram each of the digested pAmFs69 bt1 fragment, digested pSaMF36 C4T521 fragment, and the digested pSaMF21 mdh fragment to a 250 μl polyethylene glycol (PEG) solution (60% w/v polyethylene glycol (PEG), 10 mM Tris 6.5, mM CaCl) followed by gentle mixing and incubation at 37° C. for 30 minutes. Each transformation reaction was diluted with 6 ml of STC buffer, followed by plating three separate aliquots onto COVE plates. Each plate was then incubated at 34° C. for 7-10 days. Sixty of the resulting transformants (designated ShTh6900 transformants) were transferred to individual COVE plates and incubated at 34° C. for 5 days. Spore stocks were prepared by collecting the spores in 0.1% TWEEN® 80. Cultures were stored by preparing a glycerol stock of each (800 μl spore stock, 200 μl 0.1% TWEEN® 80) and frozen at −80° C.

Transformants were grown in shake flask and genomic DNA isolated according to the description above. Individual PCR reactions to test for the presence of each of the four expression vector fragments were composed of 5 μl 10× reaction buffer; 0.5 μl template (80-300 ng/μl); 1.0 μl forward primer (50 pM; see below); 1.0 μl reverse primer (50 pM; see below); 0.5 μl dNTP mixture (10 mM), 16.75 μl deionized water, and 0.25 μl Phusion® DNA polymerase.

```
Forward Primer 065067 (for the pRyan1 pyc, pSaMf21
mdh, and pSaMF36 C4T521 fragments):
                                        (SEQ ID NO: 46)
5'-TGACCTTCCACGCTGACCAC-3'

Forward Primer 0610854 (for the pAmFs69 bt1
fragment):
                                        (SEQ ID NO: 47)
5'-GGCTGAGAAAATATGTTGCA-3'

Reverse Primer 0611365 (for the pSaMF36 C4T521
fragment):
                                        (SEQ ID NO: 48)
5'-GATAGACCACTAATCATGGTGGCGATGGAG-3'

Reverse Primer 061752 (for the pRyan1 pyc
fragment)
                                        (SEQ ID NO: 49)
5'-TGCGGTCCTGAGTCAGGCCCAGTTGCTCGA-3'
```

```
Reverse Primer 062400 (for the pSaMF21 mdh
fragment)
                                      (SEQ ID NO: 50)
5'-GGGATTTGAACAGCAGAAGG-3'

Reverse Primer 996270 (for the pAmFs69 bt1
fragment)
                                      (SEQ ID NO: 51)
5'-TCACAAAAGAGTAGAGGCCA-3'
```

The amplification reactions were incubated in an EPPENDORF® MASTERCYCLER® programmed for 1 cycle at 98° C. for 30 seconds; 35 cycles each at 98° C. for 10 seconds; 66° C. (for the pRyan1 pyc fragment) or 58° C. (for the pAmFs69 bt1, pSaMf21 mdh, and pSaMf36 C4T521 fragments) for 10 seconds; 72° C. for 15 seconds; and one cycle of 72° C. for 10 minutes. *Aspergillus oryzae* NRRL 3488 genomic DNA (110 ng/µl) was used as a negative control template and each plasmid (pRyan1, pAmFs69, pSaMf21, or pSaMf36 diluted to 20 ng/µl) was used as positive control template. Amplification reaction mixtures were analyzed by gel electrophoresis using 2 µl of each reaction mixture on a 0.8% agarose gel. Transformants resulting in the expected PCR fragment sizes confirming integration were then tested for production of malic acid as described below.

Control transformants containing expression vector fragments of pSaMF36, pSaMF21, and pRyan1, but lacking pAmFs69 (designated SaMf3603 transformants) were prepared and verified in a similar procedure to that described above.

Example 7

Production of Malic Acid in Shake Flask Cultures of *Aspergillus oryzae* Transformants Containing Expression Vector Fragments of pAmFs69, pRyan1, pSaMf21, and pSaMf36 (ShTh6900)

Spores from ShTh6900 transformants described in Example 6 and *Aspergillus oryzae* NRRL 3488 as a control were plated onto individual PDA plates and allowed to sporulate at 34° C. for 5 to 7 days. Spores were collected in 0.1% TWEEN® 80 and counted using a hemacytometer. Seed cultures were prepared in 250 ml flasks containing 100 ml of seed medium B and inoculated with 300 µl of spore suspension. Seed cultures were grown for approximately 17 hours at 30° C. with shaking at 200 rpm. Acid production cultures were prepared in 250 ml unbaffled flasks containing 50 ml of acid production medium C and 3 ml of the 17 hour seed cultures. Cultures were incubated at 30° C. with shaking at 200 rpm for 2-10 days.

Quantitation of malic acid for the shake flask culture transformants was performed by Reverse Phase High Pressure Liquid Chromatography (RP-HPLC) using an 1200 Series Binary LC System and 1200 Series Diode Array Detector (DAD) (Agilent Technologies, Santa Clara, Calif. USA). Reverse phase separation was performed using an Aqua 5µ C18 125 Å 205×4.6 mm ID column and AQ C18 4×3.0 mm Security Guard Cartridge (Phenomenex, Inc., Torrance, Calif., USA). The mobile phase consisted of 10% methanol (HPLC grade) and 90% 145 mM phosphate pH 1.5 buffer.

Whole culture samples were removed and diluted 1:10 in HPLC Running Buffer composed of 850 ml of 64 mM phosphate buffer and 150 ml of methanol pH 1.65. The samples were then filtered through a 25 mm 0.45 micron polyethersulfone membrane (Whatman, Florham Park, N.J., USA) and 1.5 ml of the filtrates were placed into a HPLC vial for acid analysis. The remaining amount of the shake flask cultures were filtered through 3 layers of cheese cloth and rinsed three times with 10 volumes of double distilled sterile water to remove insoluble $CaCO_3$. Cell pellets were harvested from the cheese cloth, placed into a 15 ml culture tube and stored at −20° C.

RP-HPLC was performed using an injection volume of 10 µl at a flow rate of 0.7 ml/minute (isocratic) with a column temperature of 25° C. and run time of 11 minutes. Detection was set at 210 nm, 8 nm bandwidth, with the reference at 360 nm, 40 nm bandwidth. The void time was determined to be 3.8 minutes. The quantitative capabilities of the reverse phase method were determined for malic acid by performing replicate injections of serially diluted malic acid standards with concentrations ranging from 49.2-3.93 mM. The relative standard deviation for (RSD) for replicate injections was 5%. Malic acid shows $R^2 \geq 0.9999$.

*Aspergillus oryzae* ShTh6900 transformants containing expression vector fragments of pAmFs69, pRyan1, pSaMf21, and pSaMf36 showed malic acid titers more than two-fold over the *Aspergillus oryzae* NRRL 3488 control strains, and higher than titers observed in separate experiments with SaMf3603 transformants (containing expression vector fragments of pSaMF36, pSaMF21, and pRyan1, but lacking the expression vector fragment of pAmFs69).

Example 8

Fermentation of *Aspergillus oryzae* Transformants Containing Expression Vector Fragments of pAmFs69, pRyan1, pSaMf21, and pSaMf36 (ShTh6900)

*Aspergillus oryzae* ShTh6900 transformants described in Example 7 and control transformant *Aspergillus oryzae* SaMf3603 (containing expression vector fragments of pSaMF36, pSaMF21, and pRyan1, but lacking the expression vector fragment of pAmFs69) were grown for approximately 7 days at 34° C. on PDA plates. A 5-6 ml volume of sterile sodium phosphate buffer (50 mM, pH 6.8) containing 0.2% TWEEN® 80 was added to each plate and spores were suspended by scraping with an inoculating loop. Each suspension was transferred by pipette to a 50 ml conical tube. For each tube, 25 ml of sterile sodium phosphate buffer (50 mM, pH 6.8) containing 0.2% TWEEN® 80 was added to a 500 ml unbaffled flask containing 75 ml of seed medium, which was then inoculated with 2 ml of spore suspension. The flasks were then incubated at 34° C. and 180 rpm for about 24 hours. The seed flasks were combined to supply the 144 ml inoculum required per tank.

Three-liter fermentors containing 1.8 liters of fermentor batch medium were individually inoculated by introducing 144 ml (8%) of the seed culture broth from three combined seed flasks of either an *Aspergillus oryzae* ShTh6900 transformants or an *Aspergillus oryzae* ShTh3603 transformants. The fermentors were equilibrated at 34° C.±0.1° C. and stirred at 500 rpm. Inlet air flow was maintained at 1 v/v/m. A 25% glucose stream was administered at a rate of approximately 7.3 g/hr beginning at about 20 hours of fermentation. Sterile $CaCO_3$ (about 100 g) was added around day 5 to keep the fermentation pH in the range of 6 to 7. Samples were withdrawn daily and analyzed for malic acid production as described in Example 6. Fermentation was completed after 7 or 8 days.

The ShTh6900 transformants showed higher malic acid titers than the SaMF3603 control strains, with a faster production rate (especially over the first 72 hours) and a more rapid consumption of glucose.

Example 9

Transformation of Expression Vector Fragments of pShTh147 into *Aspergillus oryzae* M727 (ShTh147)

Protoplast preparation and transformation of *Aspergillus oryzae* M727 (a mutant strain of ShTh6900 produced by standard mutagenesis with NTG and selected for increased C4 acid production) were performed by inoculating approximately 2×10$^7$ spores into 100 ml YEG medium and incubating the flask at 27° C. for 16-18 hours at 140 rpm. Mycelia were collected by pouring the culture through a sterile funnel lined with MIRACLOTH® and rinsing with 50 ml of 0.7 M KCl. The washed mycelia were resuspended in a 125 ml flask with 20 ml of protoplasting solution composed of 5 mg of GLUCANEX™ (Novozymes A/S) and 0.5 mg of chitinase (Sigma) per ml of 0.7 M KCl (filter sterilized) and incubated at 34° C., for 30 minutes with mixing at 80 rpm. The protoplasting solution was poured through a sterile funnel lined with MIRACLOTH® and rinsed with 50 ml of STC composed of 1 M sorbitol-10 mM Tris-HCl pH 6.5-10 mM CaCl$_2$. The flow-through was collected in two 50 ml polypropylene tubes. The tubes were spun in the centrifuge at 1300×g for 10 minutes at room temperature. The supernatant was discarded and the protoplast pellet was resuspended in 20 ml of STC buffer. The protoplasts were washed by two rounds pellet resuspension in 20 ml of STC buffer and centrifugation at 1300×g for 10 minutes at room temperature. The final pellet was resuspended in 2 ml of STC buffer. The protoplasts were counted by removing a 10 µl sample and counting them in a haemocytometer (VWR). The volume was adjusted with STC buffer to obtain a protoplast concentration of 2×10$^7$ per ml.

The plasmid expression vectors pShTh147 (Example 2) was prepared for transformation by restriction digestion with Pme I for 4 hours at 37° C. The approximately 5.2 kb expression cassette was separated from the vector sequences by 0.8% agarose gel electrophoresis in TBE buffer, and purified using a QIAQUICK® Gel Extraction Kit according to manufacturer's instructions.

Four transformation reactions were prepared by adding 100 µl of protoplast preparation above into four 12 ml polypropylene tubes. To each tube was added two micrograms of the digested pShTh147 bt2 fragment to a 250 µl polyethylene glycol (PEG) solution (60% w/v polyethylene glycol (PEG), 10 mM Tris 6.5, 10 mM CaCl) followed by gentle mixing and incubation at 37° C. for 30 minutes. Each transformation reaction was diluted with 6 ml of STC buffer, followed by plating three separate aliquots onto COVE plates. Each plate was then incubated at 34° C. for 7-10 days. Forty of the resulting transformants (designated ShTh147 transformants) were transferred to individual COVE plates and incubated at 34° C. for 5 days. Spore stocks were prepared by collecting the spores in 0.1% TWEEN® 80. Cultures were stored by preparing a glycerol stock of each (800 µl spore stock, 200 µl 0.1% TWEEN® 80) and frozen at −80° C.

Example 10

Production of Malic Acid in Shake Flask Cultures of *Aspergillus oryzae* Transformants Containing Expression Vector Fragments of pAmFs69, pRyan1, pSaMf21, pSaMf36, and pShTh147 (ShTh147)

Spores from ShTh147 transformants described in Example 9 and *Aspergillus oryzae* NRRL 3488 as a control were plated onto individual PDA plates and allowed to sporulate at 34° C. for 5 to 7 days. Spores were collected in 0.1% TWEEN® 80 and counted using a hemacytometer. Seed cultures were prepared in 250 mL flasks containing 100 mL of seed medium B and inoculated with 1 mL of harvested spores. Seed cultures were grown for approximately 22 hours at 30° C. with shaking at 200 rpm. Acid production cultures were prepared in 250 mL unbaffled flasks containing 50 mL of acid production medium C and 3 mL of the 22 hour seed cultures. Cultures were incubated at 30° C. with shaking at 200 rpm for 3 days.

Quantitation of malic acid for the shake flask culture transformants was performed by Reverse Phase High Pressure Liquid Chromatography (RP-HPLC) using an 1200 Series Binary LC System and 1200 Series Diode Array Detector (DAD) (Agilent Technologies, Santa Clara, Calif. USA). Reverse phase separation was performed using an Aqua 5µ C18 125 Å 205×4.6 mm ID column and AQ C18 4×3.0 mm Security Guard Cartridge (Phenomenex, Inc., Torrance, Calif., USA). The mobile phase consisted of 10% methanol (HPLC grade) and 90% 145 mM phosphate pH 1.5 buffer.

Whole culture samples were removed and diluted 1:20 in HPLC Running Buffer composed of 900 ml of 145 mM phosphate buffer and 100 ml of methanol pH 1.50. The samples were then filtered through a 96 well 0.45 micron Durapore PVDF membrane into a 96 well plate for acid analysis.

RP-HPLC was performed using an injection volume of 10 µl at a flow rate of 0.7 ml/minute (isocratic) and column temperature at 20° C. Detection was at 210 nm, 4 nm bandwidth, with the reference at 360 nm, 40 nm bandwidth. The run time was 13 minutes. The void time was determined to be 3.8 minutes. The quantitative capabilities of the reverse phase method were determined for malic acid by performing replicate injections of serially diluted malic acid standards with concentrations ranging from 49.2-3.93 mM. The relative standard deviation for (RSD) for replicate injections was ≤5%. Malic acid shows $R^2 \geq 0.9999$.

After shake flask testing, six *Aspergillus oryzae* ShTh147 transformants were identified that produced malic acid at levels above the M727 control, including two that were improved 1.15× and 1.14×.

The present invention may be further described by the following numbered paragraphs:

[1] A recombinant host cell comprising a heterologous polynucleotide that encodes a bicarbonate transporter, wherein the host cell is capable of producing a greater amount of a C4-dicarboxylic acid compared to the host cell without the heterologous polynucleotide when cultivated under the same conditions.

[2] The recombinant host cell of paragraph [1], wherein the bicarbonate transporter is a sulfate-bicarbonate transporter.

[3] The recombinant host cell of paragraph [1] or [2], wherein the bicarbonate transporter is selected from:
   (a) a polypeptide having at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 2 or 4, or the mature polypeptide sequence thereof;

(b) a polypeptide encoded by a polynucleotide that hybridizes under low stringency conditions, medium stringency conditions, medium-high stringency conditions, high stringency conditions, or very high stringency conditions with (i) SEQ ID NO: 1 or 3, or the mature polypeptide coding sequence thereof, (ii) the cDNA sequence of SEQ ID NO: 1 or 3, or the mature polypeptide coding sequence thereof; or (iii) the full-length complementary strand of (i) or (ii);

(c) a polypeptide encoded by a polynucleotide having at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to (iv) SEQ ID NO: 1 or 3, or the mature polypeptide coding sequence thereof, (v) the cDNA sequence of SEQ ID NO: 1 or 3, or the mature polypeptide coding sequence thereof; or (vi) the full-length complementary strand of (iv) or (v);

(d) a variant comprising a substitution, deletion, and/or insertion of one or more (several) amino acids of SEQ ID NO: 2 or 4, or the mature polypeptide sequence thereof; and (e) a fragment of (a), (b), (c), or (d) that has bicarbonate transporter activity.

[4] The recombinant host cell of any one of paragraphs [1]-[3], wherein the bicarbonate transporter has at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 2 or 4, or the mature polypeptide sequence thereof.

[5] The recombinant host cell of any one of paragraphs [1]-[4], wherein the bicarbonate transporter is encoded by a polynucleotide that hybridizes under low stringency conditions, medium stringency conditions, medium-high stringency conditions, high stringency conditions, or very high stringency conditions with (i) SEQ ID NO: 1 or 3, or the mature polypeptide coding sequence thereof, (ii) the cDNA sequence of SEQ ID NO: 1 or 3, or the mature polypeptide coding sequence thereof; or (iii) the full-length complementary strand of (i) or (ii).

[6] The recombinant host cell of any one of paragraphs [1]-[5], wherein the bicarbonate transporter is encoded by a polynucleotide having at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to (iv) SEQ ID NO: 1 or 3, or the mature polypeptide coding sequence thereof, (v) the cDNA sequence of SEQ ID NO: 1 or 3, or the mature polypeptide coding sequence thereof; or (vi) the full-length complementary strand of (iv) or (v).

[7] The recombinant host cell of any one of paragraphs [1]-[6], wherein the bicarbonate transporter comprises or consists of SEQ ID NO: 2 or 4, or the mature polypeptide sequence thereof.

[8] The recombinant host cell of any one of paragraphs [1]-[6], wherein the bicarbonate transporter comprises or consists of SEQ ID NO: 2 or 4.

[9] The recombinant host cell of any one of paragraphs [1]-[6], wherein the bicarbonate transporter comprises or consists of SEQ ID NO: 2.

[10] The recombinant host cell of any one of paragraphs [1]-[6], wherein the bicarbonate transporter comprises or consists of SEQ ID NO: 4.

[11] The recombinant host cell of any one of paragraphs [1]-[6], wherein the bicarbonate transporter comprises or consists of the mature polypeptide sequence of SEQ ID NO: 2 or 4.

[12] The recombinant host cell of any one of paragraphs [1]-[6], wherein the bicarbonate transporter comprises or consists of the mature polypeptide sequence of SEQ ID NO: 2.

[13] The recombinant host cell of any one of paragraphs [1]-[6], wherein the bicarbonate transporter comprises or consists of the mature polypeptide sequence of SEQ ID NO: 4.

[14] The recombinant host cell of any one of paragraphs [1]-[6], wherein the bicarbonate transporter is a variant comprising a substitution, deletion, and/or insertion of one or more (several) amino acids of SEQ ID NO: 2 or 4, or the mature polypeptide sequence thereof.

[15] The recombinant host cell of any one of paragraphs [1]-[6], wherein the bicarbonate transporter is a variant comprising a substitution, deletion, and/or insertion of one or more (several) amino acids of SEQ ID NO: 2 or 4.

[16] The recombinant host cell of any one of paragraphs [1]-[6], wherein the bicarbonate transporter is a variant comprising a substitution, deletion, and/or insertion of one or more (several) amino acids of SEQ ID NO: 2.

[17] The recombinant host cell of any one of paragraphs [1]-[6], wherein the bicarbonate transporter is a variant comprising a substitution, deletion, and/or insertion of one or more (several) amino acids of SEQ ID NO: 4.

[18] The recombinant host cell of any one of paragraphs [1]-[6], wherein the bicarbonate transporter is a variant comprising a substitution, deletion, and/or insertion of one or more (several) amino acids of the mature polypeptide sequence of SEQ ID NO: 2 or 4.

[19] The recombinant host cell of any one of paragraphs [1]-[6], wherein the bicarbonate transporter is a variant comprising a substitution, deletion, and/or insertion of one or more (several) amino acids of the mature polypeptide sequence of SEQ ID NO: 2.

[20] The recombinant host cell of any one of paragraphs [1]-[6], wherein the bicarbonate transporter is a variant comprising a substitution, deletion, and/or insertion of one or more (several) amino acids of the mature polypeptide sequence of SEQ ID NO: 4.

[21] The recombinant host cell of any one of paragraphs [1]-[6], wherein the bicarbonate transporter is a fragment of SEQ ID NO: 2 or 4, wherein the fragment has bicarbonate transporter activity.

[22] The recombinant host cell of any one of paragraphs [1]-[6], wherein the bicarbonate transporter is a fragment of SEQ ID NO: 2, wherein the fragment has bicarbonate transporter activity.

[23] The recombinant host cell of any one of paragraphs [1]-[6], wherein the bicarbonate transporter is a fragment of SEQ ID NO: 4, wherein the fragment has bicarbonate transporter activity.

[24] The recombinant host cell of any one of paragraphs [1]-[23], wherein the heterologous polynucleotide is operably linked to a promoter foreign to the polynucleotide.

[25] The recombinant host cell of any one of paragraphs [1]-[24], further comprising a heterologous second polynucleotide encoding a C4-dicarboxylic acid transporter (e.g., a heterologous polynucleotide encoding SEQ ID NO: 6, 27, 29, 32, 34, 36, 39, 41, or 43, or any related aspect thereof).

[26] The recombinant host cell of paragraph [25], wherein the heterologous second polynucleotide is operably linked to a promoter foreign to the polynucleotide.

[27] The recombinant host cell of any one of paragraphs [1]-[26], further comprising a heterologous third polynucleotide encoding a malate dehydrogenase (e.g., a heterologous polynucleotide encoding SEQ ID NO: 8 or 45, or any related aspect thereof).

[28] The recombinant host cell of paragraph [27], wherein the heterologous third polynucleotide is operably linked to a promoter foreign to the polynucleotide.

[29] The recombinant host cell of any one of paragraphs [1]-[28], further comprising a heterologous forth polynucleotide encoding a pyruvate carboxylase (e.g., a heterologous polynucleotide encoding SEQ ID NO: 10, or any related aspect thereof).

[30] The recombinant host cell of paragraphs [29], wherein the heterologous forth polynucleotide is operably linked to a promoter foreign to the polynucleotide.

[31] The recombinant host cell of any one of paragraphs [1]-[24], further comprising a heterologous second polynucleotide encoding a C4-dicarboxylic acid transporter, a heterologous third polynucleotide encoding a malate dehydrogenase, and a heterologous forth polynucleotide encoding a pyruvate carboxylase.

[32] The recombinant host cell of any one of paragraphs [1]-[31], wherein the host cell is a eukaryotic host cell.

[33] The recombinant host cell of paragraph [32], wherein the host cell is a filamentous fungal host cell.

[34] The recombinant host cell of paragraph [33], wherein the host cell is selected from the group consisting of an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Rhizopus, Schizophyllum, Talaromyces, Thermoascus, Thielavia, Tolypocladium, Trametes*, and *Trichoderma*.

[35] The recombinant host cell of paragraph [34], wherein the host cell is an *Aspergillus* host cell.

[36] The recombinant host cell of paragraph [35], wherein the host cell is an *Aspergillus oryzae* host cell.

[37] The recombinant host cell of paragraph [35], wherein the host cell is an *Aspergillus niger* host cell.

[38] The recombinant host cell of any one of paragraphs [1]-[37], wherein the C4-dicarboxylic acid is selected from malic acid, succinic acid, oxaloacetic acid, malonic acid, and fumaric acid.

[39] The recombinant host cell of paragraph [38], wherein the C4-dicarboxylic acid is malic acid.

[40] The recombinant host cell of any one of paragraphs [1]-[39], wherein the cell is capable of C4-dicarboxylic acid volumetric productivity greater than about 0.1 g/L per hour, e.g., greater than about 0.2 g/L per hour, 0.5 g/L per hour, 0.6 g/L per hour, 0.7 g/L per hour, 0.8 g/L per hour, 0.9 g/L per hour, 1.0 g/L per hour, 1.1 g/L per hour, 1.2 g/L per hour, 1.3 g/L per hour, 1.5 g/L per hour, 1.75 g/L per hour, 2.0 g/L per hour, 2.25 g/L per hour, 2.5 g/L per hour, or 3.0 g/L per hour; or between about 0.1 g/L per hour and about 2.0 g/L per hour, e.g., between about 0.3 g/L per hour and about 1.7 g/L per hour, about 0.5 g/L per hour and about 1.5 g/L per hour, about 0.7 g/L per hour and about 1.3 g/L per hour, about 0.8 g/L per hour and about 1.2 g/L per hour, or about 0.9 g/L per hour and about 1.1 g/L per hour.

[41] The recombinant host cell of any one of paragraphs [1]-[40], wherein the host cell is capable of producing a greater amount of the C4-dicarboxylic acid by at least 5%, e.g., at least 10%, at least 15%, at least 20%, at least 25%, at least 30%, at least 50%, or at least 100% compared to the host cell without the heterologous polynucleotide that encodes the bicarbonate transporter, when cultivated under the same conditions.

[42] A composition comprising the recombinant host cell of any one of paragraphs [1]-[41].

[43] The composition of paragraph [42], wherein the medium is a fermentable medium.

[44] The composition of paragraph [42] or [43], further comprising a C4-dicarboxylic acid.

[45] The composition of paragraph [44], wherein the C4-dicarboxylic acid is selected from malic acid, succinic acid, oxaloacetic acid, malonic acid, and fumaric acid.

[46] The composition of paragraph [45], wherein the C4-dicarboxylic acid is malic acid.

[47] The composition of any one of paragraphs [42]-[46], wherein the C4-dicarboxylic acid is at a titer greater than about 10 g/L, e.g., greater than about 25 g/L, 50 g/L, 75 g/L, 100 g/L, 125 g/L, 150 g/L, 160 g/L, 170 g/L, 180 g/L, 190 g/L, 200 g/L, 210 g/L, 225 g/L, 250 g/L, 275 g/L, 300 g/L, 325 g/L, 350 g/L, 400 g/L, or 500 g/L; or between about 10 g/L and about 500 g/L, e.g., between about 50 g/L and about 350 g/L, about 100 g/L and about 300 g/L, about 150 g/L and about 250 g/L, about 175 g/L and about 225 g/L, or about 190 g/L and about 210 g/L.

[48] A method of producing a C4-dicarboxylic acid, comprising:
(a) cultivating the recombinant host cell of any one of paragraphs [1]-[41] in a medium under suitable conditions to produce the C4-dicarboxylic acid; and
(b) recovering the C4-dicarboxylic acid.

[49] The method of paragraph [48], wherein the medium is a fermentable medium.

[50] The method of paragraph [48] or [49], wherein the C4-dicarboxylic acid is at a titer greater than about 10 g/L, e.g., greater than about 25 g/L, 50 g/L, 75 g/L, 100 g/L, 125 g/L, 150 g/L, 160 g/L, 170 g/L, 180 g/L, 190 g/L, 200 g/L, 210 g/L, 225 g/L, 250 g/L, 275 g/L, 300 g/L, 325 g/L, 350 g/L, 400 g/L, or 500 g/L; or between about 10 g/L and about 500 g/L, e.g., between about 50 g/L and about 350 g/L, about 100 g/L and about 300 g/L, about 150 g/L and about 250 g/L, about 175 g/L and about 225 g/L, or about 190 g/L and about 210 g/L.

[51] The method of any one of paragraphs [48]-[50], wherein the amount of the produced C4-dicarboxylic acid is at least 5%, e.g., at least 10%, at least 15%, at least 20%, at least 25%, at least 30%, at least 50%, or at least 100% greater compared to cultivating the host cell without the polynucleotide encoding that encodes the bicarbonate transporter under the same conditions.

[52] The method of any one of paragraphs [48]-[51], wherein the C4-dicarboxylic acid is selected from malic acid, succinic acid, oxaloacetic acid, malonic acid, and fumaric acid.

[53] The method of paragraph [52], wherein the C4-dicarboxylic acid is malic acid.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A recombinant fungal or prokaryotic host cell comprising a heterologous polynucleotide encoding a bicarbonate transporter, wherein the heterologous polynucleotide:
   (a) encodes a bicarbonate transporter having at least 90% sequence identity to SEQ ID NO: 4; or
   (b) has at least 90% sequence identity to SEQ ID NO: 3, or the cDNA sequence thereof;
   wherein the host cell is capable of producing a greater amount of a C4-dicarboxylic acid compared to the host cell without the heterologous polynucleotide when cultivated under the same conditions.

2. The recombinant host cell of claim 1, wherein the heterologous polynucleotide encodes a bicarbonate transporter having at least 90% sequence identity to SEQ ID NO: 4.

3. The recombinant host cell of claim 1, wherein the heterologous polynucleotide encodes a bicarbonate transporter having at least 95% sequence identity to SEQ ID NO: 4.

4. The recombinant host cell of claim 1, wherein the heterologous polynucleotide has at least 90% sequence identity to SEQ ID NO: 3, or the cDNA sequence thereof.

5. The recombinant host cell of claim 1, wherein the heterologous polynucleotide has at least 95% sequence identity to SEQ ID NO: 3, or the cDNA sequence thereof.

6. The recombinant host cell of claim 1, wherein the heterologous polynucleotide encodes a polypeptide that comprises or consists of SEQ ID NO: 4.

7. The recombinant host cell of claim 1, wherein the heterologous polynucleotide encoding the bicarbonate transporter is operably linked to a promoter foreign to the polynucleotide.

8. The recombinant host cell of claim 1, further comprising a heterologous polynucleotide encoding a C4-dicarboxylic acid transporter.

9. The recombinant host cell of claim 8, wherein the heterologous polynucleotide encoding a C4-dicarboxylic acid transporter is operably linked to a promoter foreign to the polynucleotide.

10. The recombinant host cell of claim 1, further comprising a heterologous polynucleotide encoding a malate dehydrogenase.

11. The recombinant host cell of claim 10, wherein the heterologous polynucleotide encoding a malate dehydrogenase is operably linked to a promoter foreign to the polynucleotide.

12. The recombinant host cell of claim 1, further comprising a heterologous polynucleotide encoding a pyruvate carboxylase.

13. The recombinant host cell of claim 12, wherein the heterologous polynucleotide encoding a pyruvate carboxylase is operably linked to a promoter foreign to the polynucleotide.

14. The recombinant host cell of claim 13, wherein the host cell is a filamentous fungal host cell.

15. The recombinant host cell of claim 14, wherein the host cell is selected from the group consisting of an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phiebia, Piromyces, Pleurotus, Rhizopus, Schizophyllum, Talaromyces, Thermoascus, Thielavia, Tolypocladium, Trametes*, and *Trichoderma*.

16. The recombinant host cell of claim 14, wherein the host cell is an *Aspergillus* host cell.

17. The recombinant host cell of claim 16, wherein the host cell is an *Aspergillus oryzae* host cell.

18. The recombinant host cell of claim 16, wherein the host cell is an *Aspergillus niger* host cell.

19. The recombinant host cell of claim 1, wherein the C4-dicarboxylic acid is malic acid.

20. The recombinant host cell of claim 1, wherein the host cell is capable of producing a greater amount of the C4-dicarboxylic acid by at least 25% compared to the host cell without the heterologous polynucleotide that encodes the bicarbonate transporter, when cultivated under the same conditions.

21. The recombinant host cell of claim 1, wherein the heterologous polynucleotide encodes a bicarbonate transporter having at least 97% sequence identity to SEQ ID NO: 4.

22. The recombinant host cell of claim 1, wherein the heterologous polynucleotide encodes a bicarbonate transporter having at least 98% sequence identity to SEQ ID NO: 4.

23. The recombinant host cell of claim 1, wherein the heterologous polynucleotide encodes a bicarbonate transporter having at least 99% sequence identity to SEQ ID NO: 4.

24. The recombinant host cell of claim 1, wherein the heterologous polynucleotide has at least 97% sequence identity to SEQ ID NO: 3, or the cDNA sequence thereof.

25. The recombinant host cell of claim 1, wherein the heterologous polynucleotide has at least 98% sequence identity to SEQ ID NO: 3, or the cDNA sequence thereof.

26. The recombinant host cell of claim 1, wherein the heterologous polynucleotide has at least 99% sequence identity to SEQ ID NO: 3, or the cDNA sequence thereof.

27. A recombinant *Aspergillus oryzae* host cell comprising a heterologous polynucleotide that encodes a bicarbonate transporter, wherein:
  the heterologous polynucleotide is operably linked to a promoter foreign to the polynucleotide;
  the heterologous polynucleotide encodes a bicarbonate transporter having at least 95% sequence identity to SEQ ID NO: 4; and
  the host cell is capable of producing a greater amount of malic acid compared to the host cell without the heterologous polynucleotide when cultivated under the same conditions.

28. The recombinant host cell of claim 27, wherein the heterologous polynucleotide encodes a bicarbonate transporter that comprises or consists of SEQ ID NO: 4.

29. A method of producing a C4-dicarboxylic acid, comprising:
  (a) cultivating the recombinant host cell of claim 1 in a medium under suitable conditions to produce the C4-dicarboxylic acid; and
  (b) recovering the C4-dicarboxylic acid.

30. The method of claim 29, wherein the C4-dicarboxylic acid is malic acid.

* * * * *